(12) United States Patent
Kondiboyina et al.

(10) Patent No.: US 11,691,879 B2
(45) Date of Patent: Jul. 4, 2023

(54) SYSTEMS AND METHODS FOR NITRIC OXIDE GENERATION WITH HUMIDITY CONTROL

(71) Applicant: Third Pole, Inc., Waltham, MA (US)

(72) Inventors: Vineel Kondiboyina, Somerville, MA (US); Christopher Miles, Acton, MA (US); Gregory W. Hall, Belmont, MA (US); Simon E. Kozin, Lexington, MA (US); Wolfgang Scholz, Beverly, MA (US); Frank Heirtzler, Londonderry, NH (US)

(73) Assignee: Third Pole, Inc., Waltham, MA (US)

( * ) Notice: Subject to any disclaimer, the term of this patent is extended or adjusted under 35 U.S.C. 154(b) by 0 days.

(21) Appl. No.: 17/146,468

(22) Filed: Jan. 11, 2021

(65) Prior Publication Data

US 2021/0214222 A1 Jul. 15, 2021

Related U.S. Application Data

(60) Provisional application No. 62/959,929, filed on Jan. 11, 2020.

(51) Int. Cl.
*C01B 21/32* (2006.01)
*B01J 19/08* (2006.01)

(52) U.S. Cl.
CPC ............ *C01B 21/32* (2013.01); *B01J 19/088* (2013.01); *B01J 2219/0801* (2013.01);
(Continued)

(58) Field of Classification Search
CPC . C01B 21/32; B01J 19/088; B01J 2219/0801; B01J 2219/0809;
(Continued)

(56) References Cited

U.S. PATENT DOCUMENTS 709,867 A 9/1902 Bradley et al.
2,485,478 A 10/1949 Cotton
(Continued)

FOREIGN PATENT DOCUMENTS

CA 2413834 A1 6/2004
CN 1099997 3/1995
(Continued)

OTHER PUBLICATIONS

U.S. Appl. No. 15/907,241 2018/0243527 U.S. Pat. No. 10,286,176, filed Feb. 27, 2018 Aug. 30, 2018 May 14, 2019, Systems and Methods for Generating Nitric Oxide, Woodward, Valerie Lynn.
(Continued)

*Primary Examiner* — Xiuyu Tai
(74) *Attorney, Agent, or Firm* — Greenberg Traurig, LLP; David J. Dykeman; Jaime Burke

(57) ABSTRACT

Systems, methods and devices for nitric oxide generation are provided for use with various ventilation and/or medical devices and having a humidity control system associated therewith. In some embodiments, a system for generating nitric oxide comprises at least one pair of electrodes configured to generate a product gas containing nitric oxide from a reactant gas, a scrubber configured to remove nitric dioxide $NO_2$ from the product gas, and a humidity control device configured to alter a water content of at least one of the reactant gas and the product gas to control humidity within the system.

21 Claims, 44 Drawing Sheets

(52) U.S. Cl.
CPC .................... *B01J 2219/0809* (2013.01); *B01J 2219/0875* (2013.01); *B01J 2219/0894* (2013.01)

(58) Field of Classification Search
CPC ...... B01J 2219/0875; B01J 2219/0894; A61K 33/00; A61M 16/024; A61M 16/12; A61M 16/0093; A61M 16/101; A61M 16/022; A61M 16/0057; A61M 16/202; A61M 16/04; A61M 16/0666; A61M 16/107; A61M 2205/8206; A61M 2209/088; A61M 2205/125; A61M 2205/80; A61M 2202/0283; A61M 2205/502; A61M 2205/3584; A61M 2202/0275; A61M 2205/054; A61M 2205/05; A61M 2202/0007; A61M 2202/0057
See application file for complete search history.

(56) References Cited

U.S. PATENT DOCUMENTS

| | | |
|---|---|---|
| 2,485,481 A | 10/1949 | Cotton |
| 2,525,938 A | 10/1950 | Peck |
| 2,684,448 A | 7/1954 | Nilles |
| 3,047,370 A | 7/1962 | Aviges et al. |
| 3,225,309 A | 12/1965 | Phelps |
| 4,287,040 A | 9/1981 | Alamaro |
| 4,500,563 A | 2/1985 | Ellenberger et al. |
| 4,505,795 A | 3/1985 | Alamaro |
| 4,680,694 A | 7/1987 | Huynh et al. |
| 4,695,358 A | 9/1987 | Mizuno et al. |
| 4,705,670 A | 11/1987 | O'Hare |
| 4,816,229 A | 3/1989 | Jensen et al. |
| 4,877,589 A | 10/1989 | Conrad |
| 5,285,372 A | 2/1994 | Huynh et al. |
| 5,378,436 A | 1/1995 | Endoh et al. |
| 5,396,882 A | 3/1995 | Zapol |
| 5,413,097 A | 5/1995 | Birenheide et al. |
| 5,471,977 A | 12/1995 | Olsson et al. |
| 5,485,827 A | 1/1996 | Zapol et al. |
| 5,531,218 A | 7/1996 | Krebs |
| 5,546,935 A | 8/1996 | Champeau |
| 5,558,083 A | 9/1996 | Bathe et al. |
| 5,573,733 A | 11/1996 | Salama |
| 5,674,381 A | 10/1997 | Dekker |
| 5,692,495 A | 12/1997 | Sheu |
| 5,732,693 A | 3/1998 | Bathe et al. |
| 5,749,937 A | 5/1998 | Detering et al. |
| 5,752,504 A | 5/1998 | Bathe |
| 5,827,420 A | 10/1998 | Shirazi et al. |
| 5,839,433 A | 11/1998 | Higenbottam |
| 5,845,633 A | 12/1998 | Psaros |
| 6,089,229 A | 7/2000 | Bathe et al. |
| 6,109,260 A | 8/2000 | Bathe |
| 6,125,846 A | 10/2000 | Bathe et al. |
| 6,164,276 A | 12/2000 | Bathe et al. |
| 6,186,140 B1 | 2/2001 | Hoague |
| 6,186,142 B1 | 2/2001 | Schmidt et al. |
| 6,197,091 B1 | 3/2001 | Ji et al. |
| 6,224,653 B1 | 5/2001 | Shvedchikov et al. |
| 6,250,302 B1 | 6/2001 | Rantala |
| 6,290,683 B1 | 9/2001 | Erez et al. |
| 6,296,827 B1 | 10/2001 | Castor et al. |
| 6,365,868 B1 | 4/2002 | Borowy et al. |
| 6,432,077 B1 | 8/2002 | Stenzler |
| 6,532,956 B2 | 3/2003 | Hill |
| 6,536,429 B1 | 3/2003 | Pavlov et al. |
| 6,581,599 B1 | 6/2003 | Stenzler |
| 6,668,828 B1 | 12/2003 | Figley et al. |
| 6,758,214 B2 | 7/2004 | Fine et al. |
| 6,920,876 B2 | 7/2005 | Miller et al. |
| 6,955,171 B1 | 10/2005 | Figley et al. |
| 6,955,790 B2 | 10/2005 | Castor et al. |
| 6,984,256 B2 | 1/2006 | Lamprecht et al. |
| 6,986,351 B2 | 1/2006 | Figley et al. |
| 7,025,869 B2 | 4/2006 | Fine et al. |
| 7,040,313 B2 | 5/2006 | Fine et al. |
| 7,122,018 B2 | 10/2006 | Stenzler et al. |
| 7,220,393 B2 | 5/2007 | Miller et al. |
| 7,255,105 B2 | 8/2007 | Figley et al. |
| 7,299,785 B1 | 11/2007 | Lee |
| 7,312,584 B2 | 12/2007 | Tamita et al. |
| 7,335,181 B2 | 2/2008 | Miller et al. |
| 7,485,324 B2 | 2/2009 | Miller et al. |
| 7,498,000 B2 | 3/2009 | Pekshev et al. |
| 7,516,742 B2 | 4/2009 | Stenzler et al. |
| 7,520,866 B2 | 4/2009 | Stenzler et al. |
| 7,523,752 B2 | 4/2009 | Montgomery et al. |
| 7,531,133 B2 | 5/2009 | Hole et al. |
| 7,560,076 B2 | 7/2009 | Rounbehler et al. |
| 7,589,473 B2 | 9/2009 | Suslov |
| 7,597,731 B2 | 10/2009 | Palmerton et al. |
| 7,618,594 B2 | 11/2009 | Rounbehler et al. |
| 7,744,812 B2 | 6/2010 | Witherspoon et al. |
| 7,861,516 B2 | 1/2011 | Allanson et al. |
| 7,861,717 B1 | 1/2011 | Krebs |
| 7,914,743 B2 | 3/2011 | Fine et al. |
| 7,947,227 B2 | 5/2011 | Fine et al. |
| 7,955,294 B2 | 6/2011 | Stenzler et al. |
| 8,030,849 B2 | 10/2011 | Suslov |
| 8,043,252 B2 | 10/2011 | Miller et al. |
| 8,057,742 B2 | 11/2011 | Rounbehler et al. |
| 8,066,904 B2 | 11/2011 | Fine et al. |
| 8,079,998 B2 | 12/2011 | Hole et al. |
| 8,083,997 B2 | 12/2011 | Rounbehler et al. |
| 8,091,549 B2 | 1/2012 | Montgomery et al. |
| 8,151,791 B2 | 4/2012 | Arlow et al. |
| 8,173,072 B2 | 5/2012 | Fine et al. |
| 8,187,544 B2 | 5/2012 | Fine et al. |
| 8,211,368 B2 | 7/2012 | Fine et al. |
| 8,221,800 B2 | 7/2012 | Fine et al. |
| 8,226,916 B2 | 7/2012 | Rounbehler et al. |
| 8,246,725 B2 | 8/2012 | Rounbehler et al. |
| 8,267,884 B1 | 9/2012 | Hicks |
| 8,268,252 B2 | 9/2012 | Fuller et al. |
| 8,277,399 B2 | 10/2012 | Hamilton et al. |
| 8,282,966 B2 | 10/2012 | Baldassarre et al. |
| 8,291,904 B2 | 10/2012 | Bathe et al. |
| 8,293,284 B2 | 10/2012 | Baldassarre et al. |
| 8,328,998 B2 | 12/2012 | Wada et al. |
| 8,344,627 B1 | 1/2013 | Hooke et al. |
| 8,371,296 B2 | 2/2013 | Fine et al. |
| 8,377,462 B2 | 2/2013 | DesNoyer et al. |
| 8,397,721 B2 | 3/2013 | Montgomery et al. |
| D679,366 S | 4/2013 | Fuller |
| 8,408,206 B2 | 4/2013 | Montgomery et al. |
| 8,431,163 B2 | 4/2013 | Baldassarre et al. |
| D688,352 S | 8/2013 | Montgomery et al. |
| 8,518,457 B2 | 8/2013 | Miller et al. |
| 8,573,209 B2 | 11/2013 | Bathe et al. |
| 8,573,210 B2 | 11/2013 | Bathe et al. |
| 8,574,531 B2 | 11/2013 | Miller et al. |
| 8,580,109 B2 | 11/2013 | Kruckenberg et al. |
| 8,607,785 B2 | 12/2013 | Fine et al. |
| 8,607,792 B2 | 12/2013 | Montgomery et al. |
| 8,609,026 B2 | 12/2013 | Fine et al. |
| 8,609,028 B2 | 12/2013 | Rounbehler et al. |
| 8,613,958 B2 | 12/2013 | Fine |
| 8,616,204 B2 | 12/2013 | Montgomery et al. |
| 8,646,445 B2 | 2/2014 | Fine et al. |
| D701,963 S | 4/2014 | Abarbanel et al. |
| 8,685,467 B2 | 4/2014 | Miller et al. |
| 8,701,657 B2 | 4/2014 | Fine et al. |
| 8,715,577 B2 | 5/2014 | Fine et al. |
| 8,717,733 B2 | 5/2014 | Gefter et al. |
| 8,720,440 B2 | 5/2014 | Montgomery et al. |
| 8,741,222 B2 | 6/2014 | Fine et al. |
| 8,757,148 B2 | 6/2014 | Montgomery et al. |
| 8,770,199 B2 | 7/2014 | Flanagan et al. |
| 8,776,794 B2 | 7/2014 | Bathe et al. |
| 8,776,795 B2 | 7/2014 | Bathe et al. |
| 8,790,715 B2 | 7/2014 | Montgomery et al. |
| 8,795,222 B2 | 8/2014 | Stenzler et al. |

(56) References Cited

U.S. PATENT DOCUMENTS

| | | |
|---|---|---|
| 8,795,741 B2 | 8/2014 | Baldassarre |
| 8,808,655 B2 | 8/2014 | Solovyov et al. |
| 8,821,801 B2 | 9/2014 | Rounbehler et al. |
| 8,821,828 B2 | 9/2014 | Hilbig et al. |
| 8,846,112 B2 | 9/2014 | Baldassarre |
| 8,887,720 B2 | 11/2014 | Fine et al. |
| 8,893,717 B2 | 11/2014 | Montgomery et al. |
| 8,944,049 B2 | 2/2015 | Fine et al. |
| 9,067,788 B1 | 6/2015 | Spielman et al. |
| 9,095,534 B2 | 8/2015 | Stenzler et al. |
| 9,108,016 B2 | 8/2015 | Acker et al. |
| 9,180,217 B2 | 11/2015 | Arnold et al. |
| 9,192,718 B2 | 11/2015 | Fine |
| 9,265,911 B2 | 2/2016 | Bathe et al. |
| 9,279,794 B2 | 3/2016 | Tolmie et al. |
| 9,295,802 B2 | 3/2016 | Bathe et al. |
| 9,351,994 B2 | 5/2016 | Montgomery et al. |
| 9,408,994 B2 | 5/2016 | Fine et al. |
| 9,408,993 B2 | 8/2016 | Bathe et al. |
| 9,522,249 B2 | 12/2016 | Rounbehler et al. |
| 9,550,039 B2 | 1/2017 | Flanagan et al. |
| 9,550,040 B2 | 1/2017 | Acker et al. |
| 9,573,110 B2 | 2/2017 | Montgomery et al. |
| 9,604,028 B2 | 3/2017 | Fine et al. |
| 9,701,538 B2 | 7/2017 | Fine et al. |
| 9,713,244 B2 | 7/2017 | Tabata et al. |
| 9,770,570 B2 | 9/2017 | Schnictman et al. |
| 9,795,756 B2 | 10/2017 | Flanagan et al. |
| 9,895,199 B2 | 2/2018 | Montgomery et al. |
| 9,896,337 B2 | 2/2018 | Montgomery et al. |
| 9,956,373 B2 | 5/2018 | Rounbehler et al. |
| 9,982,354 B2 | 5/2018 | Kim |
| 10,081,544 B2 | 9/2018 | Fine et al. |
| 10,086,352 B2 | 10/2018 | Fine et al. |
| 10,099,029 B2 | 10/2018 | Montgomery et al. |
| 10,124,142 B2 | 11/2018 | Rounbehler et al. |
| 10,179,222 B2 | 1/2019 | Fine et al. |
| 10,213,572 B2 | 2/2019 | Gellman et al. |
| 10,226,592 B2 | 3/2019 | Acker et al. |
| 10,232,138 B2 | 3/2019 | Acker et al. |
| 10,239,038 B2 | 3/2019 | Zapol et al. |
| 10,279,139 B2 | 5/2019 | Zapol et al. |
| 10,286,176 B2 | 5/2019 | Zapol et al. |
| 10,293,133 B2 | 5/2019 | Zapol et al. |
| 10,328,228 B2 | 6/2019 | Zapol et al. |
| 10,398,820 B2 | 9/2019 | Potenziano et al. |
| 10,426,913 B2 | 10/2019 | Tolmie et al. |
| 10,434,276 B2 | 10/2019 | Zapol et al. |
| 10,532,176 B2 | 1/2020 | Zapol et al. |
| 10,548,920 B2 | 2/2020 | Montgomery et al. |
| 10,556,082 B2 | 2/2020 | Flanagan et al. |
| 10,556,086 B2 | 2/2020 | Goldstein et al. |
| 10,576,239 B2 | 3/2020 | Zapol et al. |
| 10,646,682 B2 | 5/2020 | Zapol et al. |
| 10,682,486 B1 | 6/2020 | Moon et al. |
| 10,695,523 B2 | 6/2020 | Zapol et al. |
| 10,737,051 B2 | 8/2020 | Gellman et al. |
| 10,750,606 B1 | 8/2020 | Liu et al. |
| 10,758,703 B2 | 9/2020 | Kohlmann et al. |
| 10,773,046 B2 | 9/2020 | Schnitman et al. |
| 10,773,047 B2 | 9/2020 | Zapol et al. |
| 10,780,241 B2 | 9/2020 | Fine et al. |
| 10,814,092 B2 | 10/2020 | Rounbehler et al. |
| 10,946,163 B2 | 3/2021 | Gillerman et al. |
| 11,007,503 B2 | 5/2021 | Zapol et al. |
| 11,033,705 B2 | 6/2021 | Zapol et al. |
| 11,045,620 B2 | 6/2021 | Hall et al. |
| 11,376,390 B2 | 7/2022 | Gillerman et al. |
| 11,478,601 B2 | 10/2022 | Hall et al. |
| 11,479,464 B2 | 10/2022 | Hall et al. |
| 11,524,134 B2 | 12/2022 | Zapol et al. |
| 11,554,240 B2 | 1/2023 | Hall et al. |
| 2001/0031230 A1 | 10/2001 | Castor et al. |
| 2001/0035186 A1 | 11/2001 | Hill |
| 2002/0111748 A1 | 8/2002 | Kobayashi et al. |
| 2002/0185126 A1 | 12/2002 | Krebs |
| 2004/0019274 A1 | 1/2004 | Galloway, Jr. et al. |
| 2004/0028753 A1 | 2/2004 | Hedenstierna et al. |
| 2004/0031248 A1 | 2/2004 | Lindsay |
| 2004/0050387 A1 | 3/2004 | Younes |
| 2004/0149282 A1 | 8/2004 | Hickle |
| 2004/0168686 A1 | 9/2004 | Krebs |
| 2004/0181149 A1 | 9/2004 | Langlotz et al. |
| 2005/0172971 A1 | 8/2005 | Kolobow et al. |
| 2005/0218007 A1 | 10/2005 | Pekshev et al. |
| 2005/0263150 A1 | 12/2005 | Chathampally et al. |
| 2005/0274381 A1 | 12/2005 | Deane et al. |
| 2005/0281465 A1 | 12/2005 | Marquart et al. |
| 2006/0025700 A1 | 2/2006 | Fallik |
| 2006/0090759 A1 | 5/2006 | Howes et al. |
| 2006/0172018 A1 | 8/2006 | Fine et al. |
| 2006/0173396 A1 | 8/2006 | Hatamian |
| 2006/0207594 A1 | 9/2006 | Stenzler et al. |
| 2006/0276844 A1 | 12/2006 | Alon et al. |
| 2007/0051712 A1 | 3/2007 | Kooken et al. |
| 2007/0113851 A1 | 5/2007 | Delisle et al. |
| 2007/0151561 A1 | 7/2007 | Laurila |
| 2007/0181126 A1 | 8/2007 | Tolmie et al. |
| 2007/0190184 A1 | 8/2007 | Montgomery et al. |
| 2008/0017030 A1 | 1/2008 | Fleck |
| 2008/0078382 A1 | 4/2008 | LeMahieu et al. |
| 2008/0135044 A1 | 6/2008 | Freitag et al. |
| 2008/0176335 A1 | 7/2008 | Alberti et al. |
| 2008/0202509 A1 | 8/2008 | Dillon et al. |
| 2010/0030091 A1 | 2/2010 | Fine |
| 2010/0043789 A1 | 2/2010 | Fine et al. |
| 2010/0076325 A1 | 3/2010 | Cho et al. |
| 2010/0089392 A1 | 4/2010 | Fine et al. |
| 2010/0189808 A1 | 7/2010 | Gupta et al. |
| 2010/0275911 A1 | 11/2010 | Arlow et al. |
| 2010/0330193 A1 | 12/2010 | Baldassarre et al. |
| 2011/0140607 A1 | 6/2011 | Moore et al. |
| 2011/0240019 A1 | 10/2011 | Fine et al. |
| 2012/0093948 A1 | 4/2012 | Fine et al. |
| 2012/0279500 A1 | 11/2012 | Singvogel et al. |
| 2012/0285449 A1 | 11/2012 | Fine et al. |
| 2012/0296265 A1 | 11/2012 | Dobrynin et al. |
| 2013/0123801 A1 | 5/2013 | Umasuthan et al. |
| 2013/0150863 A1 | 6/2013 | Baumgartner |
| 2013/0239963 A1 | 9/2013 | Goldstein et al. |
| 2013/0309328 A1 | 11/2013 | Watts et al. |
| 2014/0020685 A1 | 1/2014 | Szabo |
| 2014/0031668 A1 | 1/2014 | Mobasser et al. |
| 2014/0127081 A1 | 5/2014 | Fine et al. |
| 2014/0127330 A1 | 5/2014 | Fine et al. |
| 2014/0144436 A1 | 5/2014 | Fine et al. |
| 2014/0144444 A1 | 5/2014 | Fine et al. |
| 2014/0158121 A1 | 6/2014 | Flanagan et al. |
| 2014/0166009 A1 | 6/2014 | Flanagan et al. |
| 2014/0216452 A1 | 8/2014 | Miller et al. |
| 2014/0251787 A1 | 9/2014 | Montgomery et al. |
| 2014/0363525 A1 | 12/2014 | Montgomery et al. |
| 2014/0377378 A1 | 12/2014 | Baldassarre |
| 2015/0000659 A1 | 1/2015 | Martin |
| 2015/0004248 A1 | 1/2015 | Morfill et al. |
| 2015/0034084 A1 | 2/2015 | Av-Gay et al. |
| 2015/0044305 A1 | 2/2015 | Av-Gay et al. |
| 2015/0072023 A1 | 3/2015 | Greenberg et al. |
| 2015/0075522 A1 | 3/2015 | Acker et al. |
| 2015/0090261 A1 | 4/2015 | Crosbie |
| 2015/0101604 A1 | 4/2015 | Crosbie |
| 2015/0174158 A1 | 6/2015 | Av-Gay et al. |
| 2015/0272988 A1 | 10/2015 | Av-Gay et al. |
| 2015/0328430 A1 | 11/2015 | Miller et al. |
| 2016/0022731 A1 | 1/2016 | Av-Gay et al. |
| 2016/0030699 A1 | 2/2016 | Zapol et al. |
| 2016/0038710 A1 | 2/2016 | Zapol et al. |
| 2016/0045685 A1 | 2/2016 | Hyde et al. |
| 2016/0106949 A1 | 4/2016 | Kohlmann et al. |
| 2016/0121071 A1 | 5/2016 | Moon et al. |
| 2016/0151598 A1 | 6/2016 | Fine |
| 2016/0183841 A1 | 6/2016 | Duindam et al. |
| 2016/0191887 A1 | 6/2016 | Casas |
| 2016/0228670 A1 | 8/2016 | Av-Gay et al. |

(56) References Cited

U.S. PATENT DOCUMENTS

| | | |
|---|---|---|
| 2016/0243328 A1 | 8/2016 | Tolmie et al. |
| 2016/0271169 A1 | 9/2016 | Potenziano et al. |
| 2016/0279165 A1 | 9/2016 | Av-Gay et al. |
| 2016/0324580 A1 | 11/2016 | Esterberg |
| 2016/0367775 A1 | 12/2016 | Tolmie et al. |
| 2017/0014571 A1 | 1/2017 | Deem et al. |
| 2017/0014591 A1 | 1/2017 | Tolmie et al. |
| 2017/0014592 A1 | 1/2017 | Tolmie et al. |
| 2017/0021124 A1 | 1/2017 | Tolmie et al. |
| 2017/0065631 A1 | 3/2017 | Av-Gay et al. |
| 2017/0112871 A1 | 4/2017 | Nelson et al. |
| 2017/0128694 A1 | 5/2017 | Acker et al. |
| 2017/0143758 A1 | 5/2017 | Greenberg et al. |
| 2017/0165294 A1 | 6/2017 | Dasse et al. |
| 2017/0182088 A1 | 6/2017 | Dasse et al. |
| 2017/0232166 A1 | 8/2017 | Potenziano et al. |
| 2017/0239289 A1 | 8/2017 | Av-Gay et al. |
| 2017/0259025 A1 | 9/2017 | Fine et al. |
| 2017/0296463 A1 | 10/2017 | Minton et al. |
| 2017/0348503 A1 | 12/2017 | Westermark |
| 2018/0049622 A1 | 2/2018 | Ryan et al. |
| 2018/0104432 A1 | 4/2018 | Flanagan et al. |
| 2018/0125883 A1 | 5/2018 | Av-Gay et al. |
| 2018/0126111 A1 | 5/2018 | Moon et al. |
| 2018/0133246 A1 | 5/2018 | Av-Gay et al. |
| 2018/0169370 A1 | 6/2018 | Montgomery et al. |
| 2018/0243527 A1 | 8/2018 | Zapol et al. |
| 2018/0243528 A1 | 8/2018 | Zapol et al. |
| 2018/0264032 A1 | 9/2018 | Jaffri et al. |
| 2018/0280920 A1 | 10/2018 | Zapol et al. |
| 2018/0296790 A1 | 10/2018 | Zapol et al. |
| 2018/0304038 A1 | 10/2018 | Jafri et al. |
| 2018/0311460 A1 | 11/2018 | Rounbehler et al. |
| 2018/0328842 A1 | 11/2018 | Kjaer |
| 2019/0038864 A1 | 2/2019 | Montgomery et al. |
| 2019/0092639 A1 | 3/2019 | Fine et al. |
| 2019/0127223 A1 | 5/2019 | Montgomery et al. |
| 2019/0135633 A1 | 5/2019 | Montgomery et al. |
| 2019/0143068 A1 | 5/2019 | Rounbehler et al. |
| 2019/0184116 A1* | 6/2019 | Acker .............. A61M 16/201 |
| 2019/0209993 A1 | 7/2019 | Fine et al. |
| 2019/0217042 A1 | 7/2019 | Zapol et al. |
| 2019/0217043 A1 | 7/2019 | Fine et al. |
| 2019/0233288 A1 | 8/2019 | Montgomery et al. |
| 2019/0233289 A1 | 8/2019 | Montgomery et al. |
| 2019/0276313 A1 | 9/2019 | Montgomery et al. |
| 2019/0314596 A1 | 10/2019 | Zapol et al. |
| 2019/0374739 A1 | 12/2019 | Tolmie et al. |
| 2020/0030553 A1 | 1/2020 | Keip et al. |
| 2020/0094011 A1 | 3/2020 | Zapol et al. |
| 2020/0139071 A1 | 5/2020 | Fine et al. |
| 2020/0139072 A1 | 5/2020 | Zapol et al. |
| 2020/0139073 A1 | 5/2020 | Tector et al. |
| 2020/0163989 A1 | 5/2020 | Montgomery et al. |
| 2020/0171259 A1 | 6/2020 | Flanagan et al. |
| 2020/0171264 A1 | 6/2020 | Goldstein et al. |
| 2020/0180958 A1 | 6/2020 | Fine et al. |
| 2020/0254199 A1 | 8/2020 | Bassin |
| 2020/0282375 A1 | 9/2020 | Fine et al. |
| 2020/0360649 A1 | 11/2020 | Hall et al. |
| 2020/0360690 A1 | 11/2020 | Evans et al. |
| 2020/0361772 A1 | 11/2020 | Hall et al. |
| 2020/0361773 A1 | 11/2020 | Gillerman et al. |
| 2020/0390994 A1 | 12/2020 | Gillerman et al. |
| 2021/0220586 A1 | 7/2021 | Shah et al. |
| 2021/0268221 A1 | 9/2021 | Gillerman et al. |
| 2021/0330957 A1 | 10/2021 | Potenziano et al. |
| 2021/0353898 A1 | 11/2021 | Hall et al. |
| 2021/0386954 A1 | 12/2021 | Tamiya et al. |
| 2021/0395905 A1 | 12/2021 | Silkoff et al. |
| 2022/0047837 A1 | 2/2022 | Zapol et al. |
| 2022/0135406 A1 | 5/2022 | Apollonio et al. |
| 2022/0162070 A1 | 5/2022 | Silkoff et al. |
| 2022/0211967 A1 | 7/2022 | Hall et al. |
| 2022/0296845 A1 | 9/2022 | Jackson et al. |
| 2022/0298653 A1 | 9/2022 | Silkoff et al. |
| 2022/0339391 A1 | 10/2022 | Gillerman et al. |
| 2023/0001119 A1 | 1/2023 | Richardson et al. |

FOREIGN PATENT DOCUMENTS

| | | |
|---|---|---|
| CN | 1730115 | 2/2006 |
| CN | 201037113 | 3/2008 |
| CN | 100404083 | 7/2008 |
| CN | 101036482 | 12/2010 |
| CN | 110872714 | 3/2020 |
| DE | 101 51 270 | 10/2006 |
| EP | 621051 | 10/1994 |
| EP | 0763500 | 3/1997 |
| EP | 0878208 A2 | 11/1998 |
| EP | 1036758 | 9/2000 |
| EP | 2151554 | 2/2010 |
| EP | 1854494 | 6/2012 |
| EP | 2565157 B1 | 10/2017 |
| EP | 3372267 A1 | 12/2018 |
| JP | H04132560 | 5/1992 |
| JP | 2000102616 | 4/2000 |
| JP | 2004065636 | 3/2004 |
| JP | 2006273677 | 10/2006 |
| KR | 100841741 B1 | 6/2008 |
| KR | 20100087977 | 8/2010 |
| RU | 2199167 | 2/2003 |
| WO | WO199507610 | 3/1995 |
| WO | WO2004032719 | 4/2004 |
| WO | 2005094138 A1 | 6/2004 |
| WO | WO7/146 | 11/2005 |
| WO | 2008019102 A2 | 2/2008 |
| WO | 2008112143 A1 | 9/2008 |
| WO | WO2009018837 | 2/2009 |
| WO | WO2010021944 | 2/2010 |
| WO | WO2011/002606 | 1/2011 |
| WO | 2012014805 A1 | 2/2012 |
| WO | WO2012/034089 | 3/2012 |
| WO | WO2012/094008 | 7/2012 |
| WO | 2012155213 A1 | 11/2012 |
| WO | WO2013/052548 | 4/2013 |
| WO | WO2013/070712 | 5/2013 |
| WO | WO2013/181179 | 12/2013 |
| WO | WO2014/085719 | 6/2014 |
| WO | WO2014/143842 | 9/2014 |
| WO | WO2014/144151 | 9/2014 |
| WO | 2015049783 A1 | 4/2015 |
| WO | WO2015/066278 | 5/2015 |
| WO | WO2015/127085 | 8/2015 |
| WO | WO2016/064863 | 4/2016 |
| WO | WO2018/157172 | 8/2018 |
| WO | WO2018/157175 | 8/2018 |
| WO | WO2019/046413 | 3/2019 |
| WO | WO2019/046415 | 3/2019 |
| WO | WO2019/133776 | 7/2019 |
| WO | WO2019/133777 | 7/2019 |
| WO | WO2019/222640 | 11/2019 |
| WO | WO2020/033768 | 2/2020 |
| WO | 2020115473 A1 | 6/2020 |
| WO | 2020148155 A1 | 7/2020 |
| WO | WO2020/142658 | 7/2020 |
| WO | WO2020/150195 | 7/2020 |
| WO | WO2020/232414 | 11/2020 |
| WO | WO2020/232419 | 11/2020 |
| WO | 2021087382 A1 | 5/2021 |
| WO | 2021142472 A1 | 7/2021 |
| WO | 2021245667 A1 | 12/2021 |
| WO | 2021258025 A1 | 12/2021 |
| WO | 2022123567 A1 | 6/2022 |
| WO | 2022123574 A1 | 6/2022 |
| WO | 2022123580 A1 | 6/2022 |

OTHER PUBLICATIONS

U.S. Appl. No. 15/907,258 2018/0243528 U.S. Pat. No. 10,328,228, filed Feb. 27, 2018 Aug. 30, 2018 Jun. 25, 2019, Systems and Methods for Ambulatory Generation of Nitric Oxide, Woodward, Valerie Lynn.

(56) References Cited

OTHER PUBLICATIONS

U.S. Appl. No. 16/363,505 2019/0217042 U.S. Pat. No. 10,576,329, filed Mar. 25, 2019 Jul. 18, 2019 Mar. 3, 2020, Systems and Methods for Ambulatory Generation of Nitric Oxide, Woodward, Valerie Lynn.
U.S. Appl. No. 16/388,464 2019/0314596 U.S. Pat. No. 10,532,176, filed Apr. 18, 2019 Oct. 17, 2019 Jan. 14, 2020, Systems and Methods for Generating Nitric Oxide, Woodward, Valerie Lynn.
U.S. Appl. No. 16/697,498 2020/0094011 U.S. Pat. No. 10,695,523, filed Nov. 27, 2019 Mar. 26, 2020 Jun. 30, 2020, Systems and Methods for Generating Nitric Oxide, Woodward, Valerie Lynn.
U.S. Appl. No. 16/724,233 2020/0139072, filed Dec. 21, 2019 May 7, 2020, Systems and Methods for Ambulatory Generation of Nitric Oxide, Woodward, Valerie Lynn.
U.S. Appl. No. 16/875,971 2020/0361772, filed May 15, 2020 Nov. 19, 2020, Systems and Methods for Generating Nitric Oxide, Tai, Xiuyu.
U.S. Appl. No. 16/875,687 2020/0360649, filed May 15, 2020 Nov. 19, 2020, Electrodes for Nitric Oxide Generation, Tai, Xiuyu.
U.S. Appl. No. 16/875,914 2020/0361773, filed May 15, 2020 Nov. 19, 2020, Architectures for Production of Nitric Oxide, Not Yet Assigned.
U.S. Appl. No. 16/909,722 2020/0390994 U.S. Pat. No. 10,946,163, filed Jun. 23, 2020 Dec. 17, 2020 Mar. 16, 2021, Systems and Methods for Generating Nitric Oxide, Woodward, Valerie Lynn.
U.S. Appl. No. 17/197,911, filed Mar. 10, 2021, Systems and Methods for Generating Nitric Oxide, Not Yet Assigned.
Atjunan Thesis—Plasma Produced Reactive Oxygen and Nitrogen Species in Angiogenesis—May 2011—Krishna Priya Arjunan.
Arora et al., Nitric Oxide Regulation of Bacterial Biofilms, Biochemistry, vol. 54, pp. 3717-3728, May 21, 2015.
Barraud et al., Involvement of Nitric Oxide n Biofilm Dispersal of Pseudomonas Aeruginosa, Journal of Bacteriology, vol. 188, No. 21, pp. 7344-7353, Nov. 2006.
Bellerophon, "A Dose Escalation Study to Assess the Safety and Efficacy of Pulsed iNO in Subjects With Pulmonary Fibrosis", Aug. 30, 2017, https://clinicaltrials.gov/ct2/show/NCT03267108.
Bentur et al., Pilot Study to Test Inhaled Nitric Oxide in Cystic Fibrosis Patients with Refractory *Mycobacterium abscessus* Lung Infection, Journal of Cystic Fibrosis, vol. 19, pp. 225-231, May 23, 2019.
Birkeland, K., "On the Oxidation of Atmospheric Nitrogen in Electric Arcs", A Paper read before the Faraday Society on Monday, Jul. 2, 1906, Published on Jan. 1, 1906.
Bogdonovski et al., Anti-Mycobacterial Activity of High-Dose Nitric Oxide Against *Mycobacterium abscessus* in Vitro, National Institutes of Health Poster, Jul. 8, 2018.
Charles, et al., "SiO2 Deposition from Oxygen/Silane Pulsed Helicon Diffusion Plasmas" Applied Physics Letters, vol. 67, No. 1, pp. 40-42, Jul. 3, 1995.
Deppisch et al., Gaseous Nitric Oxide to Treat Antibiotic Resistant Bacterial and Fungal Lung Infections in Patients with Cystic Fibrosis: A Phase I Clinical Study, Infection, vol. 44, pp. 513-520, Feb. 9, 2016.
Dobrynin et al. "Direct and Controllable Nitric Oxide Delivery into Biological Media and Living Cells by a Pin-to-Hole Spark Discharge (PHD) Plasma" Journal of Physics D: Applied Physics, vol. 44, pp. 1-10, Jan. 28, 2011.
Feigerle, C., et al., "Multiphoton Ionization of Vibrationally Hot Nitric Oxide Produced in a Pulsed Supersonic Glow Discharge", Journal of Chemical Physics, vol. 90, Issue 6, pp. 2900-2908, Mar. 15, 1989.
Fowler, "Exercise Intolerance in Pulmonary Arterial Hypertension", Pulmonary Medicine, vol. 2012, Article ID 39204, 11 pages, (2012).
HELI, Study on the Removal of Byproduct Nitrogen Dioxide from the Mixture of Inhaled Nitric Oxide Produced by Pulsed Arc Discharge, Thesis for Degree of Master of Engineering, Huazhong University of Science & Technology, China, Apr. 2006, 78 pages (Includes English Language Translation of Title Page and Abstract).
Howlin et al., Low-Dose Nitric Oxide as Targeted Anti-Biofilm Adjunctive Therapy to Treat Chronic Pseudomonas Aeruginosa Infection in Cystic Fibrosis, Molecular Therapy, vol. 25, No. 9, pp. 2104-2116, Sep. 2017.
Hu, Hui et al., "Study on Production of Nitric Monoxide for Respiratory Distress by Pulsed Discharge", Proceedings of the CSEE, vol. 23, No. 2, Jan. 2005.
Hu, Hui et al., "Study on Pulsed Arc Discharge Conditions on Production of Nitric Oxide for Medical Application", High Voltage Apparatus, Issue 3, Mar. 2005.
Hu et al., "Study on Production of Inhaled Nitric Oxide for Medical Applications by Pulsed Discharge" IEEE Transactions on Plasma Science, vol. 35, No. 3, pp. 619-625, Jun. 2007.
Hu, Hui et al., "The Effect of Flow Distribution on the Concentration of NO Produced by Pulsed Arc Discharge", Plasma Science and Technology, vol. 9, No. 6, pp. 766-769, Dec. 2007.
Hui, Research on the Production of Nitric Oxide by Pulsed Arc Discharge and the Curing of Respiratory Distress Instrument, Dissertation for Degree of Doctor of Philosophy in Engineering, Huazhong University of Science and Technology, China, Apr. 2005, 138 pages (Includes English Language Translation of Title Page and Abstract).
Johns Hopkins University—"American Chemical Journal vol. XXXV"—No. 4, Reports Chapter, pp. 358-368, Apr. 1906.
Keshav, Saurabh. "Using Plasmas for High-speed Flow Control and Combustion Control" Diss. The Ohio State University, 2008.
Kornev, J., et al., "Generation of Active Oxidant Species by Pulsed Dielectric Barrier Discharge in Water-Air Mixtures", Ozone: Science & Engineering, vol. 28, Issue 4, pp. 207-215, Jul. 2006.
Kuo, Spencer P. "Air Plasma for Medical Applications" J. Biomedical Science and Engineering, vol. 5, pp. 481-495, Sep. 2012.
Li, Z. et al., "Development of Miniature Pulsed Power Generator," 2005 IEEE Pulsed Power Conference, Monterey, CA, pp. 1053-1056, Jul. 2005.
Li et al., Production of Medically Useful Nitric Monoxide Using AC Arc Discharge, Nitric Oxide, vol. 73, pp. 89-95, Feb. 28, 2018.
Matsuo, K. et al., "Nitric Oxide Generated by Atmospheric Pressure Air Microplasma," 2009 IEEE Pulsed Power Conference, Washington, DC, Jun. 28-Jul. 2, 2009, pp. 999-1003, Jan. 19, 2010.
McMullin et al., The Antimicrobial Effect of Nitric Oxide on the Bacteria That Cause Nosocomial Pneumonia in Mechanically Ventilated Patients in the Intensive Care Unit, Respiratory Care, vol. 50, No. 11, pp. 1451-1456, Nov. 2005.
Miller et al., Gaseous Nitric Oxide Bactericidal Activity Retained During Intermittent High-Dose Short Duration Exposure, Nitric Oxide, vol. 20, Issue 1, pp. 16-23, Feb. 2009.
Miller et al Inhaled Nitric Oxide Decreases the Bacterial Load in a Rat Model of Pseudomonas Aeruginosa Pneumonia, Journal of Cystic Fibrosis, vol. 12, pp. 817-820, Mar. 6, 2013.
Miller et al., Nitric Oxide is a Potential Antimicrobial Against Slow and Fast Growing Mycobacteria, Online Abstracts Issue, American Journal Respiratory Care Medicine, vol. 193, A7498, May 18, 2016.
Miller et al., A Phase I Clinical Study of Inhaled Nitric Oxide in Healthy Adults, Journal of Cystic Fibrosis, vol. 11, pp. 324-331, Apr. 18, 2012.
Mok et al. "Application of Positive Pulsed Corona Discharge to Removal of SO2 and NOx," Proceedings, ICESP VII, Sep. 20-25, 1998, Kyongiu, Korea.
Namihira et al., Production of Nitric Monoxide Using Pulsed Discharges for a Medical Application, IEEE Transactions on Plasma Science, vol. 29, No. 1, pp. 109-114, Feb. 2000.
Namihara et al., "Production of NO Using Pulsed Arc Discharges and Its Medical Applications", Journal of Plasma and Fusion Research, vol. 79, No. 1 pp. 35-38, Jun. 25, 2002.
Namihira et al., "Production of Nitric Monoxide in Dry Air Using Pulsed Ddischarge," Digest of Technical Papers. 12th IEEE International Pulsed Power Conference. (Cat. No. 99CH36358), Monterey, CA, pp. 1313-1316 vol. 2, Aug. 6, 2002.
Namihira et al., Production of Nitric Oxide Using a Pulsed Arc Discharge, IEEE Transactions on Plasma Science, vol. 30, No. 5, pp. 1993-1998, Oct. 2002.

(56) References Cited

OTHER PUBLICATIONS

Namihira et al., "Temperature and Nitric Oxide Generation in a Pulsed Arc Discharge Plasma" Plasma Science and Technology, vol. 9, No. 6, pp. 747-751, Dec. 2007.
Navarro-Gonzalez et al., "The Physical Mechanism of Nitric Oxide Formation in Simulated Lightning" Geophysical Research Letters, vol. 28, No. 20, pp. 3867-3870, Oct. 15, 2001.
Olivier et al., Treatment of Refractory *Mycobacterium abscessus* Lung Infection with Inhaled Intermittent Nitric Oxide, Poster, Jul. 8, 2018.
Overzet, et al. "Why and How to Pulse a Plasma"—slide show presentation, Oct. 1997.
Patil et al., Plasma Assisted Nitrogen Oxide Production from Air, AiChE Journal, vol. 64, Issue 2, Aug. 14, 2017.
Pawlat et al., Evaluation of Oxidative Species in Gaseous, Plasma Chemistry and Plasma Processing, vol. 39, pp. 627-642, Mar. 28, 2019.
Pontiga, F., et al., "Nitrogen Oxides Generation Induced by Negative Corona Discharge in N2 + O2 Mixtures," 2006 IEEE Conference on Electrical Insulation and Dielectric Phenomena, Kansas City, MO, pp. 264-267, Oct. 2006.
Sakai, et al., "A Compact Nitric Oxide Supply for Medical Application," 2007 16th IEEE International Pulsed Power Conference, Albuquerque, NM, pp. 752-755, Oct. 14, 2008.
Sakai et al., "Nitric Oxide Generator Based on Pulsed Arc Discharge" Acta Physica Polonica A, vol. 115, No. 6, pp. 1104-1106, Jun. 2009.
Schilz, "Treatment of Pulmonary Hypertension Related to Disorders of Hypoxia" Advances in Pulmonary Hypertension, vol. 4, No. 2, pp. 14-22, May 2005.
Tal et al., Nitric Oxide Inhalations in Bronchiolitis: A Pilot, Randomized, Double-Blinded, Controlled Trial, Pediatric Pulmonology, vol. 53, Issue 1, pp. 95-102, Jan. 2018.
Wang et al., Gliding Arc Plasma for CO2 Conversion, Chemical Engineering Journal, vol. 330, pp. 11-25, 2017.
Yaacoby-Bianu et al., Compassionate Nitric Oxide Adjuvant Treatment of Persistent *Mycobacterium* Infection in Cystic Fibrosis Patients, The Pediatric Infectious Disease Journal, vol. 37, No. 4, Apr. 2018.
International Search Report in PCT/US2021/013008 dated Apr. 15, 2021.
Peterson, John. "The Relationship Between Moisture & Temperature" sciencing.com, https://sciencing.com/relationship-between-moisture-temperature-4007.html. Apr. 25, 2017.
Donohoe et al., "Production of O3, NO, and N2O in a Pulsed Discharge at 1 Atm", Ind. Eng. Chem., Fundam., vol. 16, No. 2, pp. 208-215, May 1977.
Encyclopaedia Britannica, "Soda Lime" published Nov. 12, 2018, https://www.britannica.com/science/soda-lime.
Habib, Bassam Hanna, "A Simple Model of Spark Gap Discharge Phase", Eng. & Tech. Journal, vol. 31, Part (A), No. 9, pp. 1692-1704, 2013.
Hanning et al., "Pulse Oximetry: A Practical Review", British Medical Journal, vol. 311, pp. 367-370, Aug. 5, 1995.
Higenbottam et al., "The Direct and Indirect Action of Inhaled Agents on the Lung and Its Circulation: Lessons from Clinical Science," Environmental Health Perspectives, vol. 109, Supplement 4, pp. 559-562, Aug. 2001.
Intersurgical Complete Respiratory Systems, Carbon Dioxide Absorbents Catalogue, www.intersurgical.com/distributors, Issue 5, Oct. 17, 2021.
Lorente L., "Respiratory Filters and Ventilator-Associated Pneumonia: Composition, Efficacy Tests and Advantages and Disadvantages", Humidification in the Intensive Care Unit, pp. 171-177, Springer, Berlin, Heidelberg 2012.
Takaki, et al., "Resistance of Pulsed Arc Discharge in Air and SF/sub 6", Pulsed Power Plasma Science, vol. 2, pp. 1758-1761, Jun. 2001.
Tsukahara et al., "Gas-Phase Oxidation of Nitric Oxide: Chemical Kinetics and Rate Constant," Nitric Oxide: Biology and Chemistry, vol. 3, No. 3, pp. 191-198, Jun. 1999.
Yu, et al., "Detection and Removal of Impurities in Nitric Oxide Generated from Air by Pulsed Electrical Discharge", Nitric Oxide, vol. 60, pp. 16-23, Nov. 30, 2016.
Yu, et al. "Development of a Portable Mini-Generator to Safely Produce Nitric Oxide for the Treatment of Infants with Pulmonary Hypertension", Nitric Oxide, vol. 75, pp. 7-76, May 1, 2018.
Lovich et al., "Generation of Purified Nitric Oxide from Liquid N2O4 for the Treatment of Pulmonary Hypertension in Hypoxemic Swine", Nitric Oxide vol. 37, pp. 66-77, Feb. 15, 2014.

\* cited by examiner

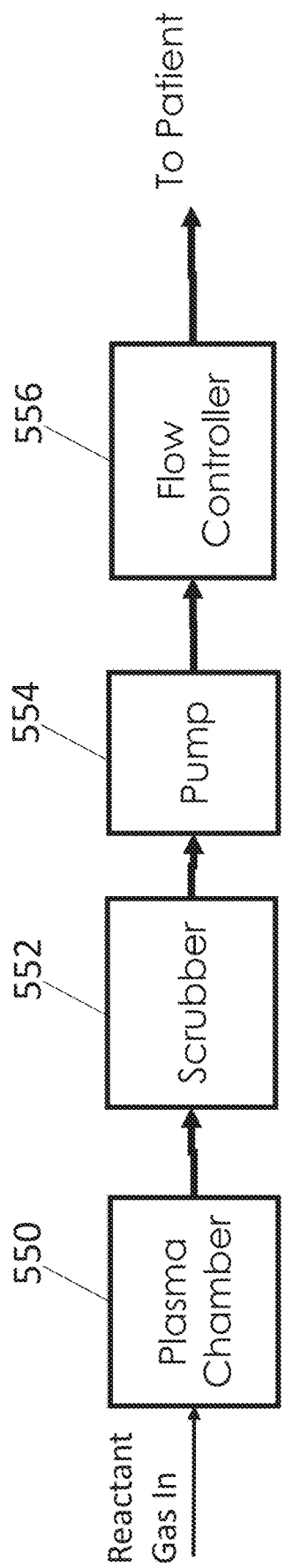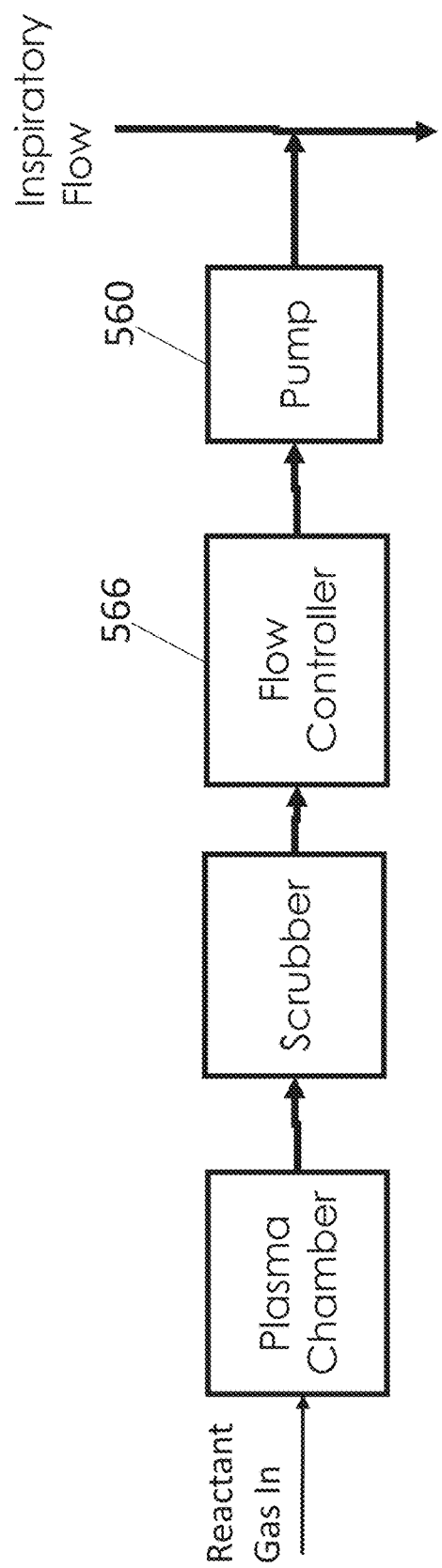
FIG. 32A
FIG. 32B

SYSTEMS AND METHODS FOR NITRIC OXIDE GENERATION WITH HUMIDITY CONTROL

RELATED APPLICATIONS

This application claims the benefit of and priority to U.S. Provisional Application Ser. No. 62/959,929, filed on Jan. 11, 2020, which is incorporated herein by reference in its entirety.

FEDERALLY SPONSORED RESEARCH OR DEVELOPMENT

This invention was made with government support under Grant No. R44 HL134429 and Grant No. R44 TR001704, awarded by the National Institutes of Health (NIH). The government has certain rights in the invention.

FIELD

The present disclosure relates to systems and methods for generating nitric oxide and controlling humidity levels within the system during nitric oxide (NO) generation.

SUMMARY

The present disclosure is directed to systems, methods and devices for nitric oxide generation for use with various ventilation and/or medical devices and having a humidity control system associated therewith.

In some embodiments, a system for generating nitric oxide comprises at least one pair of electrodes configured to generate a product gas containing nitric oxide from a reactant gas, a scrubber configured to remove $NO_2$ from the product gas, and a humidity control device configured to alter a water content of at least one of the reactant gas and the product gas to control humidity within the system.

In some embodiments, the system can further comprises at least one controller configured to regulate the amount of nitric oxide in the product gas generated by the at least one pair of electrodes using one or more parameters as an input to the controller, the one or more parameters relating to at least one of the reactant gas, the product gas, and an inspiratory gas into which at least a portion of the product gas flows. The humidity control device can be configured to communicate with the controller such that humidity information is a parameter to the controller. In some embodiments, one or more humidity sensors can be configured to communicate with at least one of the controller and the humidity control device. The one or more humidity sensors can be configured to communicate with the humidity control device to adjust the humidity in the system.

In some embodiments, the humidity control device is in the form of a water trap. In some embodiments, the humidity control device is in the form of a humidity exchange material. In some embodiments, the humidity control device is in the form of a humidity management material. In some embodiments, the humidity management material is a desiccant. In some embodiments, the humidity control device is in the form of a molecular sieve. In some embodiments, the humidity control device is configured to titrate humid and dry gas to achieve a target gas humidity level. In some embodiments, the humidity control device is in the form of at least one of an active heater and a passive heater. In some embodiments, the humidity control device is configured to prevent drying out of the scrubber.

In some embodiments, the system can include one or more sensors configured to sense information relating to at least one of the reactant gas, product gas, and inspiratory gas to be used as the parameters to the controller, and wherein the humidity control device is configured to prevent drying out of the one or more sensors.

In some embodiments, a system for generating nitric oxide comprises at least one pair of electrodes configured to generate a product gas containing nitric oxide from a reactant gas, at least one controller configured to regulate the amount of nitric oxide in the product gas generated by the at least one pair of electrodes using one or more parameters as an input to the controller, the one or more parameters relating to at least one of the reactant gas, the product gas, and an inspiratory gas into which at least a portion of the product gas flows. At least one of a temperature and pressure of at least one of the reactant gas and product gas is configured to be altered to adjust humidity within the system.

In some embodiments, the system can utilize feedback to the ability to the alter humidity as needed. In some embodiments, the system can include a scrubber configured to remove $NO_2$ from the product gas, and wherein the humidity control device is configured to prevent drying out of the scrubber. In some embodiments, the system can include one or more sensors configured to sense information relating to at least one of the reactant gas, product gas, and inspiratory gas to be used as the parameters to the controller, and wherein the humidity control device is configured to prevent drying out of the one or more sensors. In some embodiments, the humidity control device can be configured to communicate with the controller such that humidity information is a parameter to the controller.

In some embodiments, a system for generating nitric oxide comprises at least one pair of electrodes configured to generate a product gas containing nitric oxide from a reactant gas and at least one controller configured to regulate the amount of nitric oxide in the product gas generated by the at least one pair of electrodes using one or more parameters as an input to the controller, the one or more parameters relating to at least one of the reactant gas, the product gas, and an inspiratory gas into which at least a portion of the product gas flows. At least one parameter is humidity information in at least one of the reactant gas and the product gas to achieve a target NO production level. In some embodiments, one or more parameters include at least one of geographic location, elevation, and atmospheric pressure information to control NO production

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 32A and FIG. 32B depict embodiments that operate at low pressure;

Figure 1:
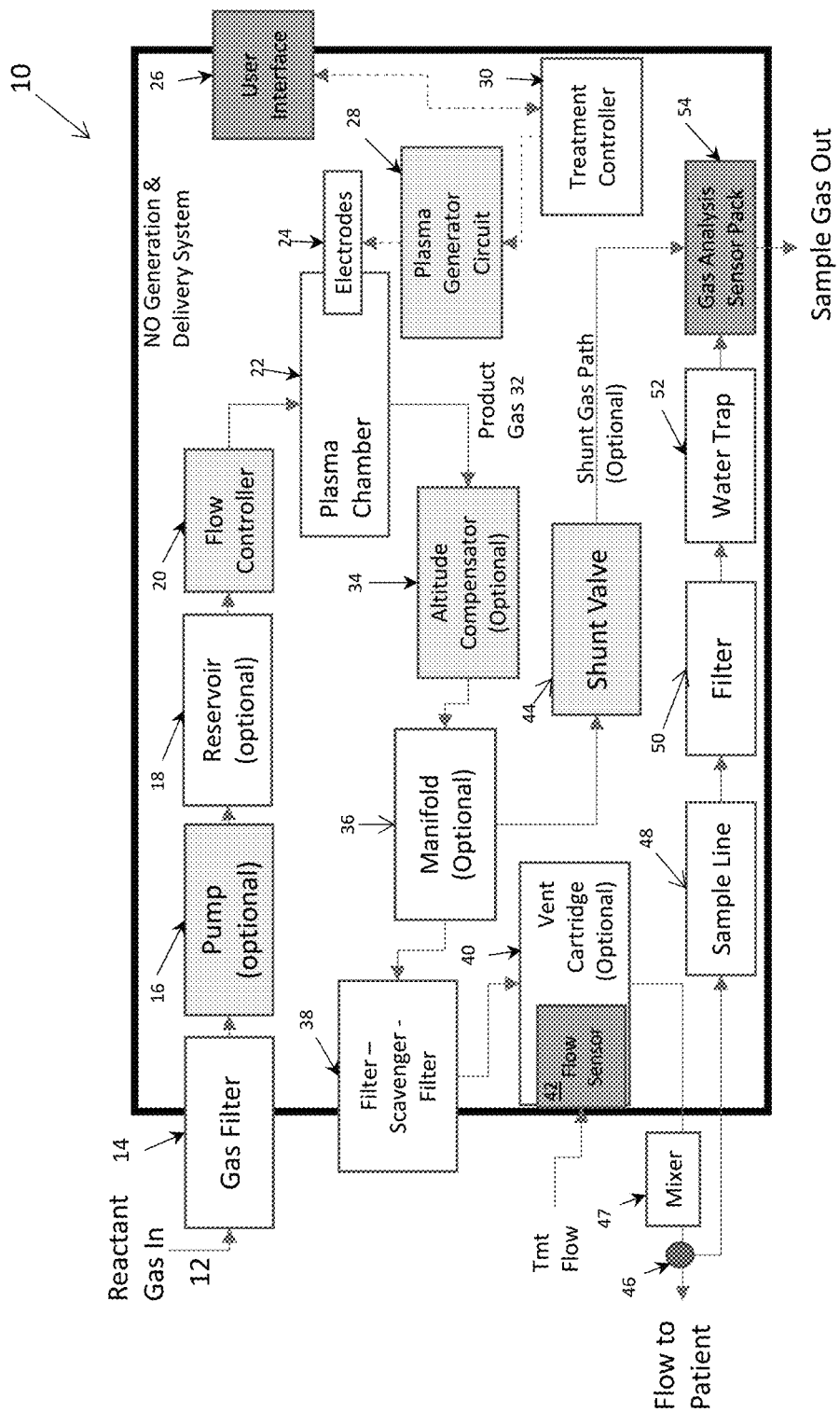
FIG. 1 is an exemplary embodiment of a system for generating an NO-enriched product gas.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments Specific details are given in the following description to provide a thorough understanding of the embodiments. However, it will be understood by one of ordinary skill in the art that the embodiments may be practiced without these specific details. For example, systems, processes, and other elements in the presently disclosed embodiments may be shown as components in block diagram form in order not to obscure the embodiments in unnecessary detail. In other instances, well-known processes, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Subject matter will now be described more fully with reference to the accompanying drawings, which form a part hereof, and which show, by way of illustration, specific example aspects and embodiments of the present disclosure. Subject matter may, however, be embodied in a variety of different forms and, therefore, covered or claimed subject matter is intended to be construed as not being limited to any example embodiments set forth herein; example embodiments are provided merely to be illustrative. The following detailed description is, therefore, not intended to be taken in a limiting sense.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure relates to systems and methods of nitric oxide (NO) delivery for use in various applications, for example, inside a hospital room, in an emergency room, in a doctor's office, in a clinic, and outside a hospital setting as a portable or ambulatory device. An NO generation and/or delivery system can take many forms, including but not limited to a device configured to work with an existing medical device that utilizes a product gas, a stand-alone (ambulatory) device, a module that can be integrated with an existing medical device, one or more types of cartridges that can perform various functions of the NO system, and an electronic NO tank. The NO generation system uses a reactant gas, including but not limited to ambient air, to produce a product gas that is enriched with NO.

An NO generation device can be used with any device that can utilize NO, including but not limited to a ventilator, an anesthesia device, house air, a defibrillator, a ventricular assist device (VAD), a Continuous Positive Airway Pressure (CPAP) machine, a Bilevel Positive Airway Pressure (Bi-PAP) machine, a non-invasive positive pressure ventilator (NIPPV), a nasal cannula application, a nebulizer, an extra-corporeal membrane oxygenation (ECMO), a bypass system, an automated CPR system, an oxygen delivery system, an oxygen concentrator, an oxygen generation system, and an automated external defibrillator AED, MRI, and a patient monitor. In addition, the destination for nitric oxide produced can be any type of delivery device associated with any medical device, including but not limited to a nasal cannula, a manual ventilation device, a face mask, or any other delivery circuit. The NO generation capabilities can be integrated into any of these devices, or the devices can be used with an NO generation device as described herein.

Electric NO can be generated from reactant gas containing nitrogen and oxygen. NO generation from dry or mostly dry reactant gas, as found from medical compressed gas cylinders or air compressor systems, has little to no variation in NO production stemming from water content variation. For a nitric oxide generation system to operate outside of a controlled environment or tethered to a house reactant gas supply requires knowledge of and/or management of humidity levels within the reactant gas. For example, electric NO generation at a given frequency and duration can vary as much as 50% solely based on the water content of the reactant gas. Water content is often measured in relative humidity (RH), the percentage of water content that gas has versus the maximum amount of water content possible before condensing at a given temperature. Humidity and water content are used interchangeably at times throughout this document, but it should be understood that they can be different.

Figure 33:
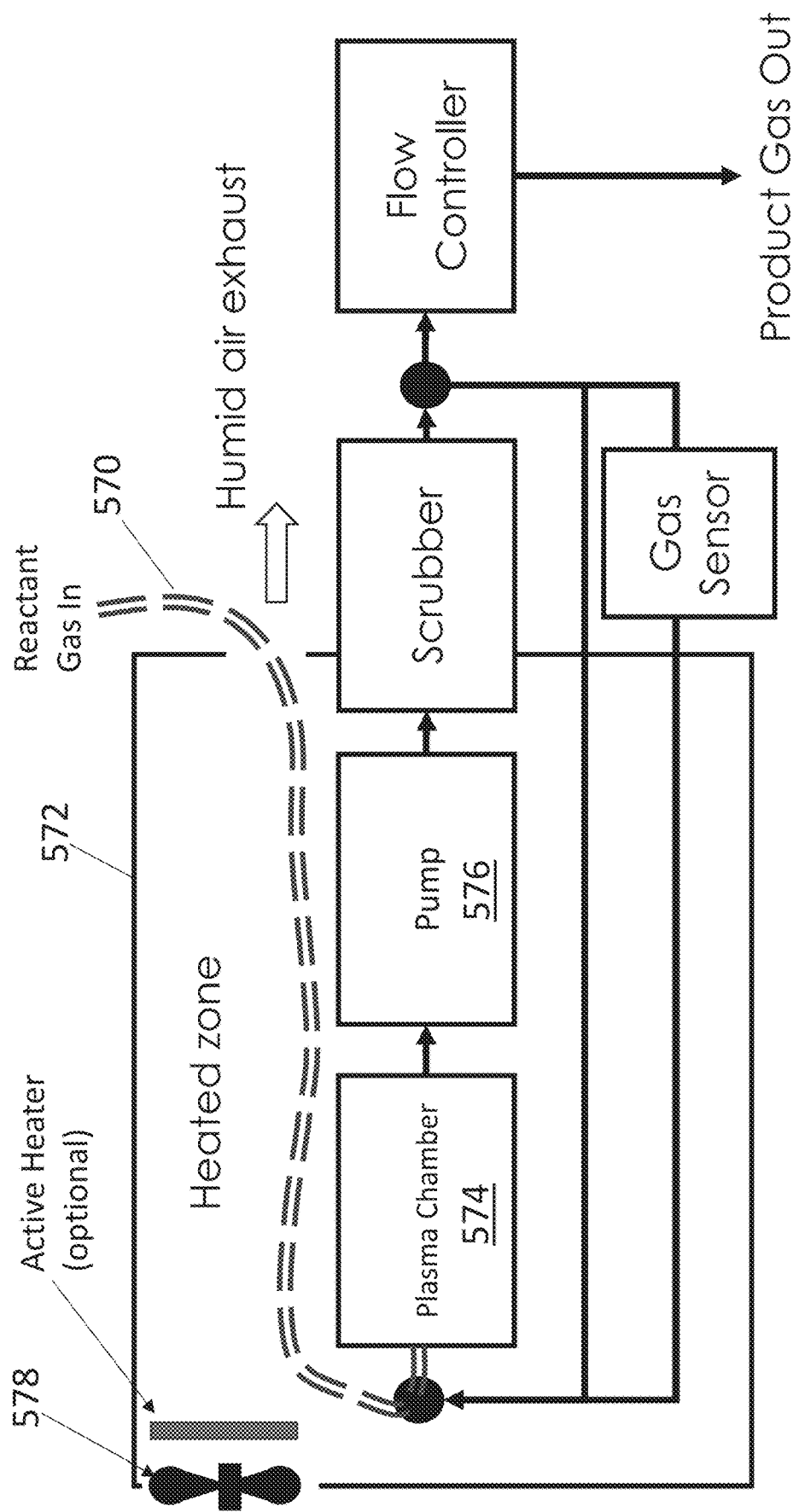
FIG. 33 depicts a NO generation system with recirculation loop architecture that utilizes passive and active heat to prevent condensation within the system.

There are two approaches to humidity control, that can be used alone or in tandem: 1) humidity compensation and 2) humidity management. Humidity compensation involves measurement of the humidity of ambient conditions, reactant gas, and/or product gas and adjusting conditions within the NO system to result in production of a target amount of nitric oxide. Conditions within the NO system that can be adjusted can include one or more of but not limited to the following: plasma energy, plasma voltage, plasma frequency, plasma duration, plasma duty cycle, reactant gas flow rate, plasma chamber temperature, reactant gas temperature, and reactant gas pressure. FIG. 33 depicts an exemplary humidity compensation table and will be discussed in more detail below.

Humidity management enables a nitric oxide generation system to accomplish one or more of the following: prevent water condensation within the system, manage condensed water within the system, protect system components from condensed water which becomes acidic in the presence of $NO_2$, maintain gas humidity within the range required for various sensors including but not limited to NO, $NO_2$ and $O_2$ sensors, and maintain reactant gas humidity in a particular range for accurate and repeatable NO generation. These approaches can involve adding/removing water from the gas to adjust water content and/or adjusting temperature and pressure to alter the dew point for a given water content level. Maintaining humidity within a target range can involve either water removal or water addition to gas, depending on ambient conditions and system component requirements. In some embodiments, for example, a gas sensor requires a gas humidity between 20% RH and 70% RH. Thus, in very dry conditions, water is added to the gas to protect the sensor and water is removed from gas in very humid conditions.

Humidity management can be done at various points within a NO generation system. In some embodiments, water is removed from reactant gas soon after entering the NO system. In other embodiments, water is removed in other regions deeper within the system, such is after a pump or within a recirculation loop, or just prior to a humidity sensitive component.

Water can be condensed and removed in liquid form or removed as a vapor. In some embodiments, water is condensed to liquid form soon after entering the system. This approach can amount to tens of ml of water or more per day to drain, evaporate or otherwise manage. In other embodiments, water is kept in vapor form and driven from incoming gases by means of gradients in pressure, humidity, and/or temperature. In other embodiments, the system operating temperature is maintained at sufficiently high levels to prevent water condensation. Some embodiments are selected for their low operating pressure that minimizes the potential of water condensation within the system.

Humidity management within a NO generator can be accomplished using various techniques, including with passive control, active control or a combination of the two.

Passive control involves controlling humidity automatically by a physical means. It will be understood that any of the embodiments described below can be used to passively control the humidity in the system. For example, reactant gas can be preconditioned by passing it over a desiccant to drive humidity levels towards a specific humidity. Efficacy of this approach depends on the quantity of desiccant (surface area) and the exposure time (flow rate, gas path length, desiccant chamber volume, etc.). Water content is exchanged between gas and desiccant without additional controls. In another example, one or more zones within a NO generator pneumatic pathway can be heated to keep gases that are at higher pressure than ambient warm enough that the relative humidity is less than 100%. In a passive control design, a heat level is utilized that can work for all operating conditions and is used all of the time.

Active humidity control enables a NO generation system to alter water content within reactant and/or product gas on an as needed basis. It will be understood that any of the embodiments described below can be used to actively control the humidity in the system.

An example of active control includes reactant gas passing through humidity exchange tubing with variable convective flow on the exterior of the tube. In some embodiments, a controller measures humidity content of the incoming reactant gas and selects a convective flow rate (e.g. fan speed) that can provide sufficient water removal from the reactant gas to prevent condensation at later, higher pressure regions within the system. With this open-loop control approach, the controller may determine a fan speed based on a look-up table or mathematical equation using one or more of the reactant gas humidity, target gas humidity, operating temperature, peak pressure within the system, convective gas temperature, convective gas humidity, convective gas pressure, and other parameters related to moisture exchange across the humidity exchange tubing.

In another example of active humidity control, a controller measures humidity of gas downstream of a humidity removal zone of the system with a sensor. The sensor is used as an input to a closed-loop control system (e.g. PID) that varies the conditions within the humidity removal zone to achieve a target gas humidity at the gas sensor. For example, if the humidity of the gas is in an acceptable range, the controller deactivates the humidity removal zone (e.g. heater, fan, or vacuum pump). When the measured humidity downstream of the humidity removal device is increasing towards an unacceptable level, the active control scheme increases water removal in the humidity removal device. In another example, as a NO generation system transitions to a higher rate of NO production, reactant gas flow rates and pressures may increase, increasing the potential for condensation. The humidity controller can receive notice of this increase in NO production from the NO generation controller and increase water removal to prevent condensation at the higher pressures and/or flow rates associated with this higher rate of production. In this way, the humidity controller modulates that rate of water removal based on the conditions of reactant gas and the NO generation system.

In another example of active control of a humidity removal device, a heater is used to increase the temperature of convective gas that flows across humidity exchange tubing containing reactant gas. As humidity of reactant gas increases, as measured by a humidity sensor, an active humidity controller increases the heater temperature to remove additional water from the reactant gas. In an open loop solution, the temperature of the heater has been predetermined by device characterization and is obtained by looking up the reactant gas humidity in a look-up-table or mathematical formula. In a closed-loop solution, the temperature of the heater is modulated based on the gas humidity measured downstream of the humidity exchange device in order to drive the humidity towards a target level. In both active control scenarios, if the humidity of the incoming gas is initially at or near the target level, humidity management is not utilized, thereby saving energy and prolonging battery life.

In one example, a NO generation device is required to operate in an operating environment from 5 to 40 deg C. and 15-95% relative humidity. The NO generation device includes a NO gas sensor that requires gas humidity to be between 20% RH and 70% RH. At the low end of the humidity spectrum, no humidity management is required due to compression of the reactant gas raising the relative humidity and water content added to the gas from a soda lime scrubber. At the high end of the humidity spectrum, however, water must be removed to prevent condensation within the NO generation system and operating the NO gas sensor out of humidity range. By actively operating humidity management on an as-needed basis, a NO generation device can reduce energy expenditure and prolong battery life.

Various methods are presented here-in to add, remove and maintain water content within a gas. It should be understood that each of these solutions can be deployed at various locations with a NO generation system, including but not limited to the device inlet, a recirculation loop, a location between plasma chamber and scrubber, a high pressure region of a NO generator, a location prior to a humidity-sensitive component and other locations as required.

Humidity of gas within a NO generation system is controlled to prevent condensation and/or decrease dehumidification by deploying the mechanisms stated above through a control algorithm which can enable the operation of the device within specifications for varying environmental conditions.

Management of humidity in a NO generation device provides the following benefits: 1) Condensation of water can be prevented, eliminating the risk of damage to sensors and other system elements from liquid moisture and/or corrosive nitric acid that forms when liquid water is exposed to nitrogen dioxide. 2) The effect of humidity variation on NO production accuracy is decreased due to the lower range of reactant gas humidity that will be exposed to plasma.

FIG. 1 illustrates an exemplary embodiment of an NO generation system 10 that includes components for reactant gas intake 12 and delivery to a plasma chamber 22. The plasma chamber 22 includes one or more electrodes 24 therein that are configured to produce, with the use of a high voltage circuit (plasma generator) 28, a product gas 32 containing a desired amount of NO from the reactant gas. The system includes a controller 30 in electrical communication with the plasma generator 28 and the electrode(s) 24 that is configured to control the concentration of NO in the product gas 32 using one or more control parameters relating to conditions within the system and/or conditions relating to a separate device for delivering the product gas to a patient and/or conditions relating to the patient receiving the product gas. In addition, the controller 30 can also be in communication with any of the various humidity control devices or mechanisms described herein to alter humidity in the system and can use various information such as measurements from one or more sensors such as humidity, temperature and/or pressure sensors. In some embodiments, the plasma generator circuit is a high voltage circuit that generates a potential difference across an electrode gap. In some embodiments, the AC and/or DC high voltage ranges from 3000 to 30,000 volts. In some embodiments, the plasma generator circuit is a radio frequency (RF) power generator delivering RF power to one or more RF electrodes. In some embodiments, the RF power operates around 13-14 MHz with power in the 50-100 W range, however other power ranges can be effective depending on electrode design, production targets and reactant gas conditions. In some embodiments, RF power operates around 2.45 GHz for improved coupling and excitation of $N_2$ molecules. The controller 30 is also in communication with a user interface 26 that enables a user to interact with the system, view information about the system and NO production, and control parameters related to NO production.

In some embodiments, the NO system pneumatic path includes a pump pushing air through a manifold 36. The manifold is configured with binary valves, three-way valves and proportional orifices. The high voltage control circuit 28 controls the flow of the pump, the plasma activity (power, duty cycle, frequency, current, voltage), and the direction of the gas flow post-electrical discharge. By configuring valves, the high voltage control circuit can direct gas to the manual respiration pathway, the ventilator pathway or the gas sensor chamber for direct measurement of NO, $NO_2$ and $O_2$ levels in the product gas.

The output from the NO generation system in the form of the product gas 32 enriched with the NO produced in the plasma chamber 22 can either be directed to a respiratory or other device for delivery to a patient or can be directed to a plurality of components provided for self-test or calibration of the NO generation system. In some embodiments, the system collects gases to sample in two ways: 1) gases are collected from a patient inspiratory circuit near the patient and pass through a sample line 48, a filter 50, and a water trap 52, or 2) gases are shunted directly from the pneumatic circuit, sourced from a location between the plasma chamber and injector. In some embodiments, product gases are shunted with a shunt valve 44 to the gas sensors after being scrubbed but before dilution into a patient airstream. In some embodiments, product gases are collected from an inspiratory air stream near the device and/or within the device post-dilution. In some embodiments, product gas and inspiratory gas pass through a mixer 47 to blend the gases prior to sampling. Within the gas analysis portion of the device, the product gas passes through one or more sensors to measure concentrations, pressure, and flow rate of various gasses therein.

Figure 2:
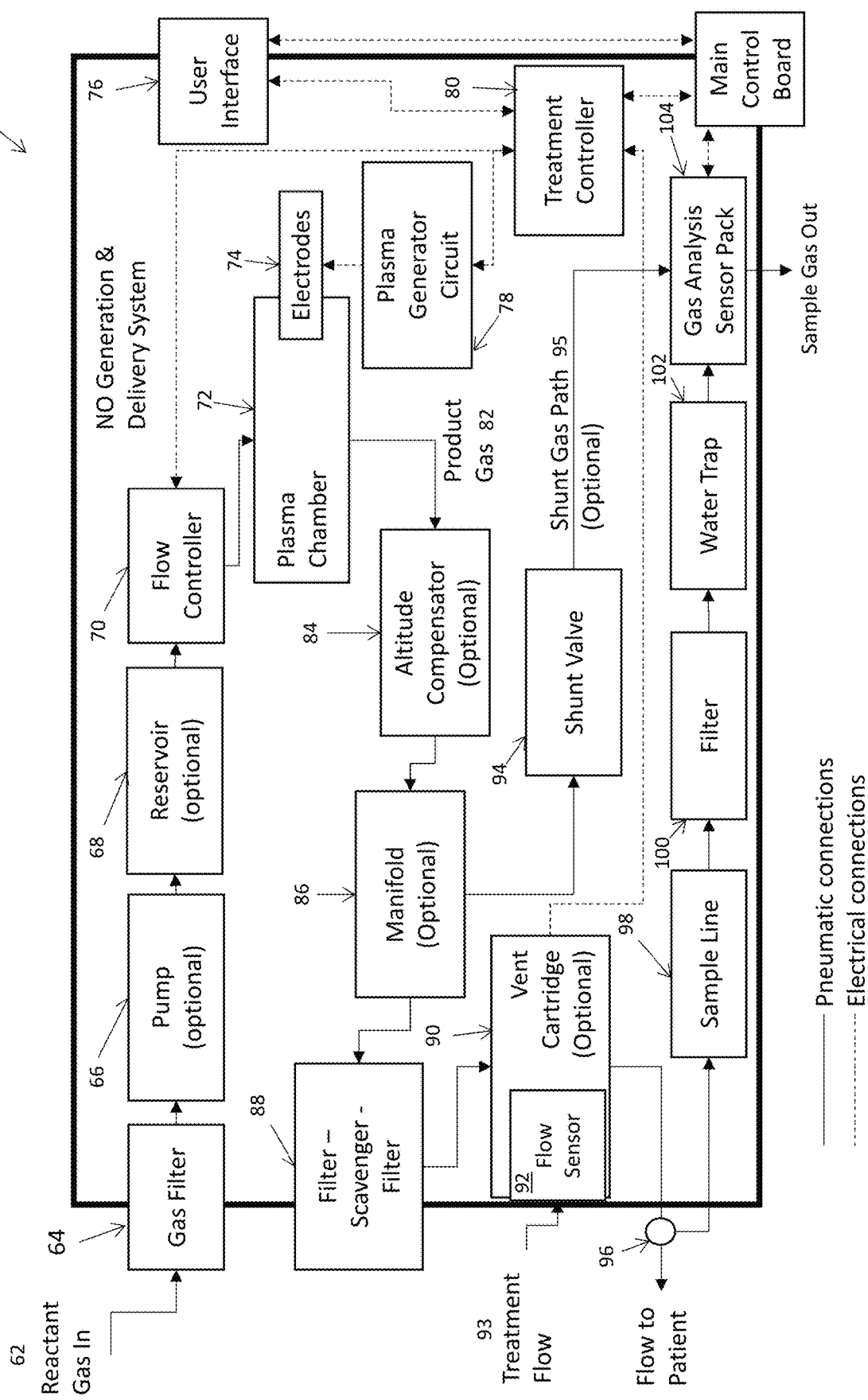
FIG. 2 is another exemplary embodiment of a system for generating an NO-enriched product gas.

FIG. 2 depicts an embodiment of a NO generation and delivery system 60. Reactant gas 62 enters the system through a gas filter 64 (for example, an activated charcoal filter). A pump 66 is used to propel gas through the system. Whether or not a system includes a pump can depend on the pressure of the reactant gas supply. If reactant gas is pressurized, a pump may not be required. If reactant gas is near or at atmospheric pressure, a pump or other means to move reactant gas through the system is required. An optional reservoir 68 after the pump attenuates rapid changes in pressure and/or flow from a pump. It should be noted that the term "reservoir" refers to a volume, the pressure of which can be controlled specific pressures above and/or below atmospheric pressure. The volume of pneumatic pathway between two components can serve as a reservoir. In some embodiments, a reservoir consists solely of tubing, manifolds and the like. In other embodiments, a reservoir consists of a discrete reservoir component consisting of chamber in addition to pneumatic pathways in fluid communication with said chamber. In some embodiments, a reservoir consists of volume within an enclosure not occupied by other system components (i.e. pump, valves, circuit boards, etc.). Coupled with a flow controller 70, the reservoir, when pressurized, can enable a system to provide flow rates to the plasma chamber 72 that are greater than the pump 66 flow rate. Electrodes 74 within the plasma chamber 72 are energized by a plasma generation circuit 78 that produces high voltage inputs based on desired treatment conditions received from a treatment controller 80. A user interface 76 receives desired treatment conditions (dose, treatment mode, etc.) from the user and communicates them to the treatment controller 80. In addition, the treatment controller 80 can also be in communication with any of the various humidity control devices or mechanisms described herein to alter humidity in the system and can use various information such as measurements from one or more sensors such as humidity, temperature and/or pressure sensors. Reactant gas 62 is converted into product gas 82 when it passes through the plasma chamber 72 and is partially converted into nitric oxide and nitrogen dioxide. An optional altitude compensator 84, typically consisting of one or more valves, is optionally used to provide a back-pressure within the plasma chamber 72 for additional controls in nitric oxide production. Product gases pass through a manifold 86, as needed, to reach a filter-scavenger-filter 88 assembly that removes nitrogen dioxide from the product gas. From the filter-scavenger-filter 88, product gas is introduced to a patient treatment flow directly, or indirectly through an injector cartridge 90. In some embodiments, the injector cartridge 90 includes a flow sensor 92 that measures the treatment flow 93. The treatment flow measurements from the flow sensor 92 serve as an input into the reactant gas flow controller 70 via the treatment controller 80. After product gas 82 is introduced to the treatment flow, it passes through inspiratory tubing. Near the patient, a fitting 96 is used to pull a fraction of inspired gas from the inspiratory flow, through a sample line 98, filter 100, water trap 102 and selective humidity exchange membrane tubing (e.g. Nafion) to prepare the gas sample and convey it to gas sensors 104. Sample gas exits the gas analysis sensor pack 104 to ambient air. In some embodiments, the system 60 can optionally direct gas through a shunt valve 94 and shunt gas path 95 directly to the gas sensor pack and out of the system. In some embodiments involving the shunt valve 94, the manifold 86 includes a valve (not shown) to block flow to the filter-scavenger-filter when the shunt valve 94 is open.

Figure 3:
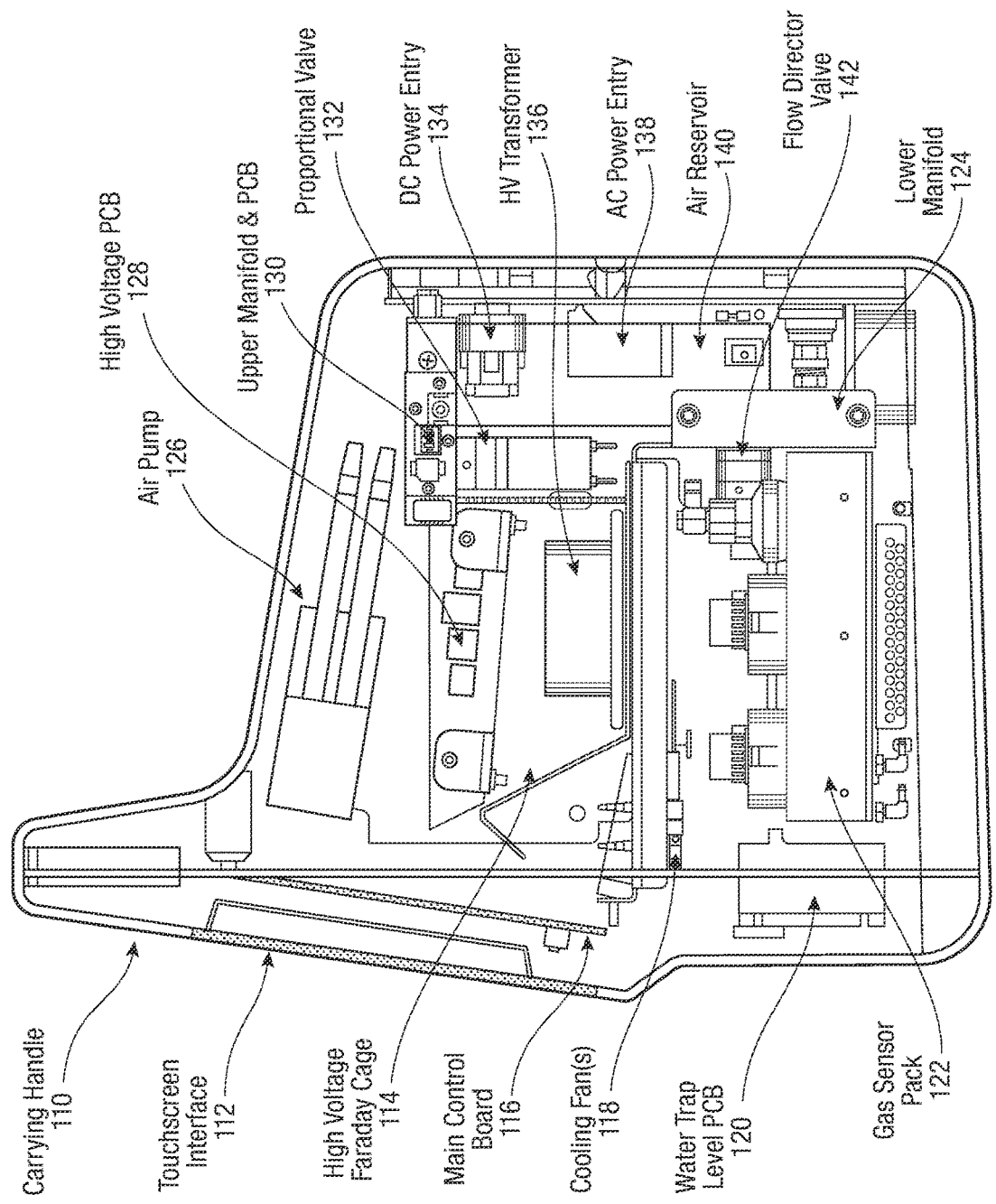
FIG. 3 is an exemplary embodiment of an NO generation system.

Another exemplary embodiment of a NO generation system is shown in FIG. 3, which includes a carrying handle 110, a user interface 112, a high voltage Faraday cage 114, a control board 116, one or more cooling fans 118, and a water trap PCB 120. The system also includes a gas sensor pack 122, a lower manifold 124, an air pump 126, a high voltage PCB 128, an upper manifold 130, a proportional valve 132, a DC power entry 134, an HV transformer 136, an AC power entry 138, a reservoir 140, and a flow director valve 142.

Figure 4:
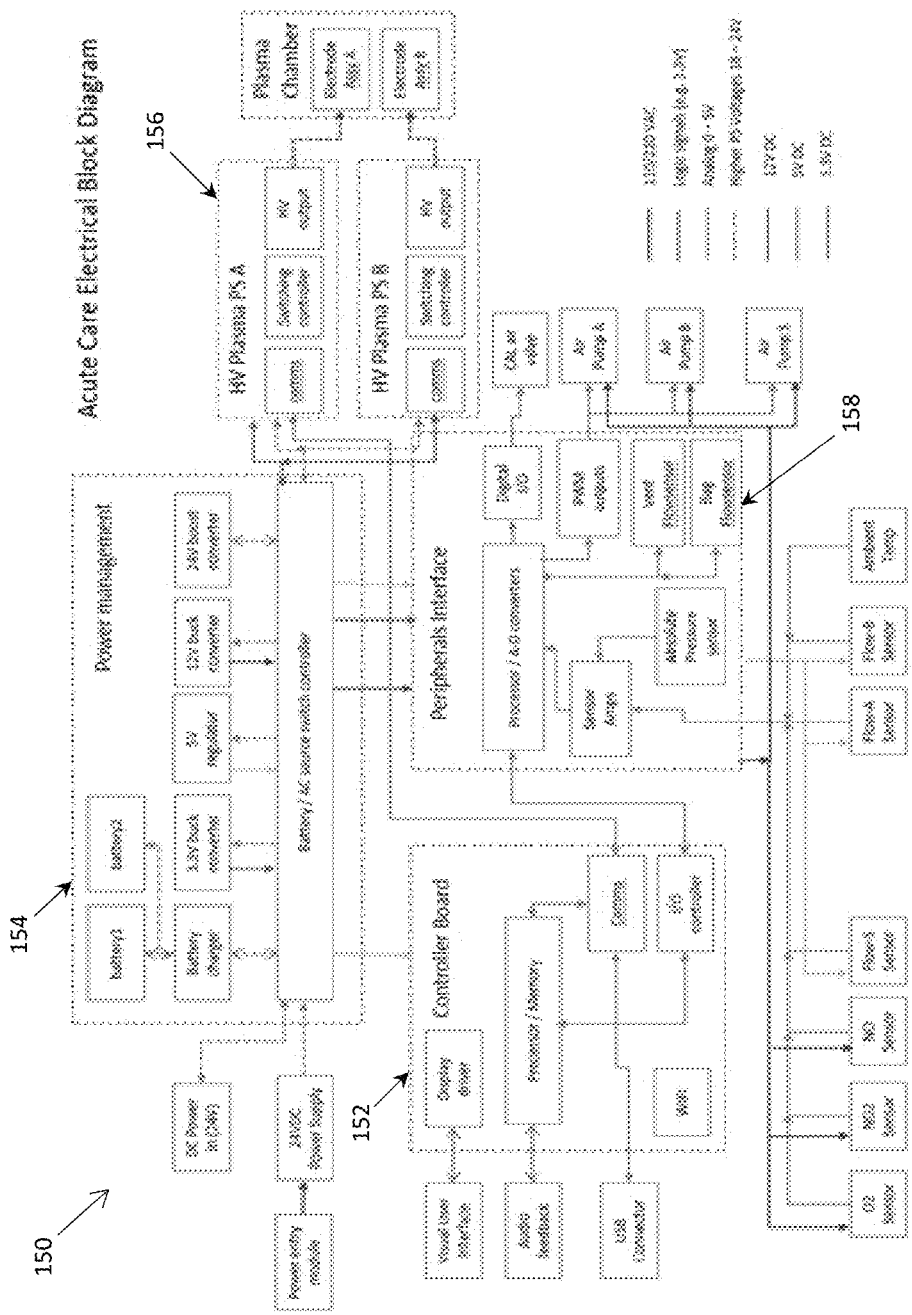
FIG. 4 illustrates an embodiment of a schematic of a controller of an NO generation system.

FIG. 4 depicts a schematic showing all the components of an embodiment of an NO device 150, including a control board 152, a power management circuit 154, one or more electrode assemblies 156, and a peripherals interface 158. A plasma chamber can be part of the controller or part of the cartridge.

Figure 5:
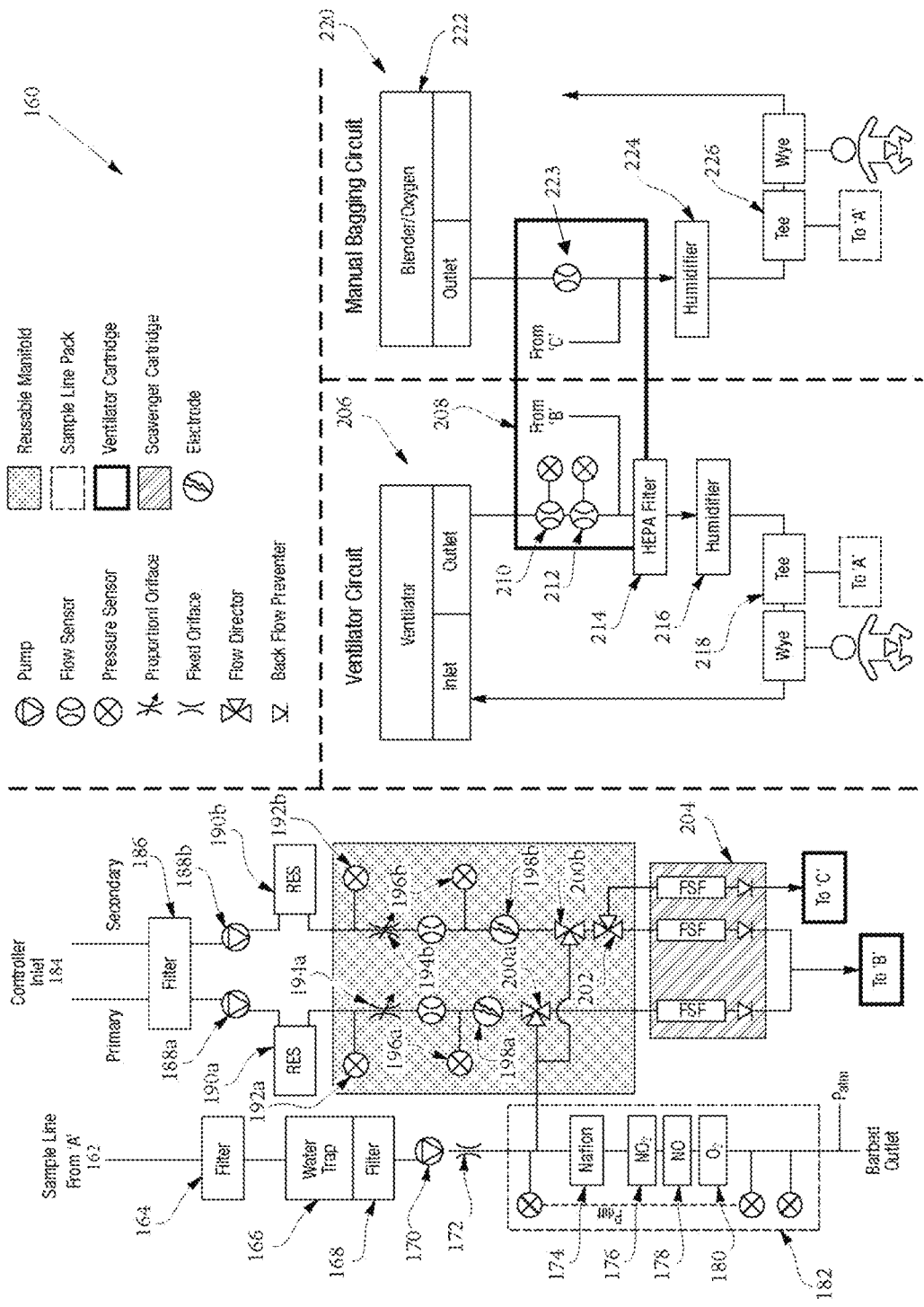
FIG. 5 is an embodiment of a pneumatic circuit.
Figure 6:
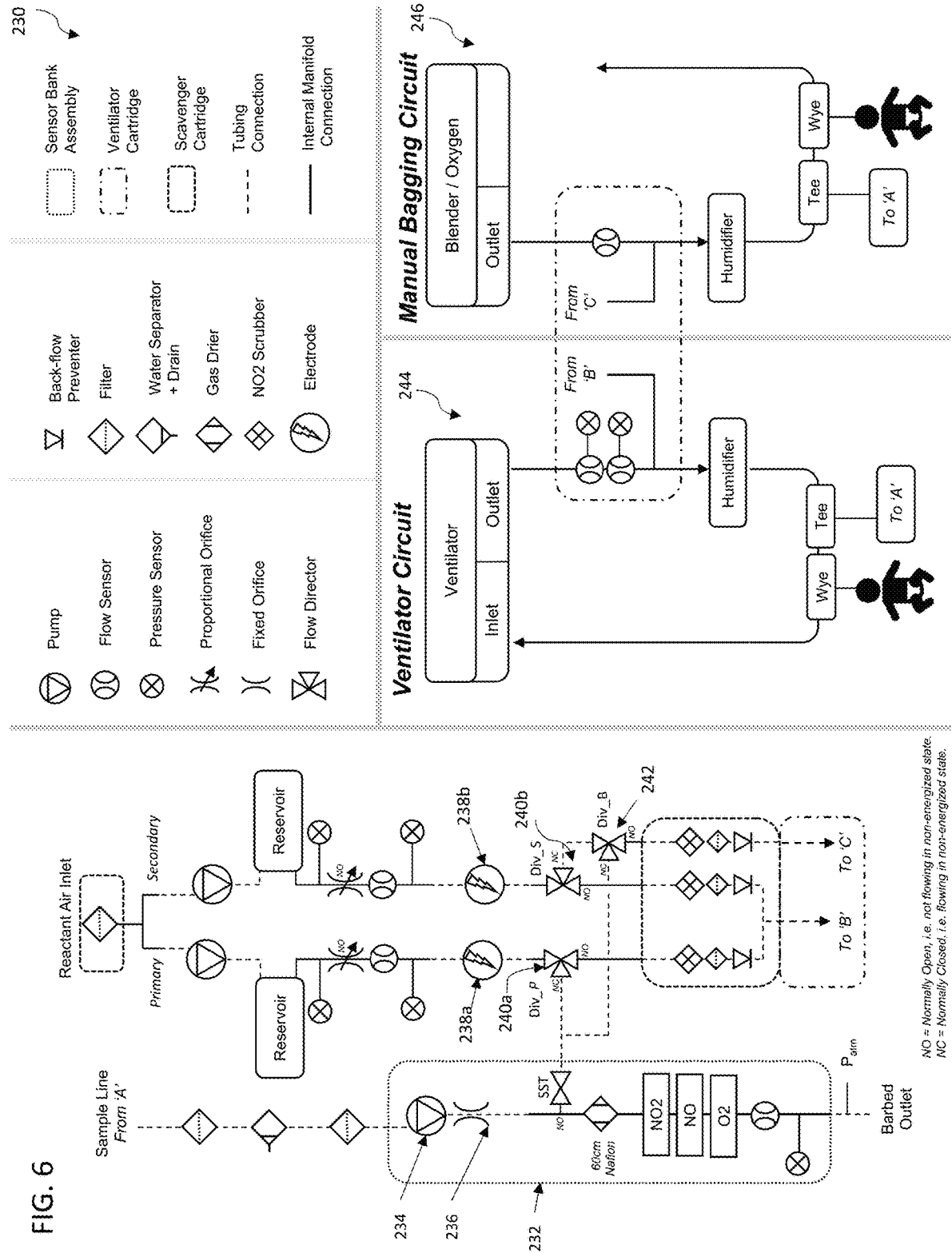
FIG. 6 is another embodiment of a pneumatic circuit.

FIG. 5 and FIG. 6 depict embodiments of NO generation and delivery systems with redundant NO generators. FIG. 5 depicts an exemplary pneumatic design 160 for an NO generation and delivery system. In the upper left of the diagram, sample gases 162 originating in the treatment circuit (lower right of FIG. 5 labeled 'A') enter the system through a filter 164 and travel through a water trap 166. In some embodiments, this filter 164 is disposable so that user can replace it as needed when it clogs. An additional filter 168 after the water trap 166 protects the gas analysis sensors for contaminants. Sample gases then flow through a pump 170 and then through a fixed orifice 172 that limits the gas flow rate through the sensors and diminishes pulsatility in the sample gas flow. Gas then flows through selective humidity exchange tubing 174 (e.g. Nafion) to add humidity to the sample from the atmosphere in the event that sample gases are very dry. Next, the sample gas flows through one or more gas analysis sensors. Sensor 176 measures $NO_2$, sensor 178 measures NO, sensor 180 measures $O_2$. $NO_2$ is measured first because it is the most important safety measurement and concentrations change over time. A differential pressure sensor, or other device such as a heated wire, shown on the left side of the sensor manifold block is used to measure the flow rate through the gas sensor manifold 182. This flow rate can be used to ensure that the sample pump is functioning. An absolute pressure sensor near the end (bottom) of the sensor manifold is used to measure atmospheric pressure. Gases exit the sensor manifold and flow through a T-fitting, where one leg is connected to atmospheric pressure and the other leg is connected to an external port in the device. The first leg is connected to atmosphere to prevent hospital vacuum from affecting the flow rate through the gas sensor manifold and potentially affecting patient treatment. The external port can be connected to hospital vacuum or just vented to atmosphere.

In further reference to FIG. 5, an inlet 184 is configured to receive reactant gas into the system. In some embodiments, this is a 22mm medical air connection. Incoming reactant gas flows through a filter 186 to remove particulate then bifurcates into two parallel NO generation paths. In some embodiments, each NO generation path has an independent reactant gas pathway and filter. Each path consists of a pump 188a, 188b, a reservoir 190a, 190b, a reservoir pressure sensor 192a, 192b, a proportional flow valve 194a, 194b, a fixed orifice, a plasma chamber pressure sensor 196a, 196b, and a plasma chamber 198a, 198b. After the plasma chamber 198a, 198b, each flow path has a flow director 200a, 200b that can direct gases to either the gas sensor manifold 182 or towards the patient inspiratory air. These side paths to the gas sensor manifold 182 enable a system to evaluate the gas produced and/or redirect gases within the plasma chamber away from the patient. After the gas analysis side paths, one of the gas paths utilizes a flow director 202 to select whether product gases will flow to a ventilator circuit (B in the figure) or to a manual bag outlet (C in the figure). Gases then flow through three parallel scrubber passages in a disposable cartridge 204. The scrubber passages consist of a filter, scrubber material, a second filter and a one-way valve. The one-way valve ensures that pressures and materials outside of the system do not enter the cartridge and controller.

FIG. 5 also includes a depiction of a treatment setup. In a ventilator circuit 206, inspiratory gases exit the ventilator and enter a ventilator cartridge 208. The gases flow through two flow sensors 210, 212. In some embodiments, a plurality of sensors can be used. In some embodiments, the flow sensors measure one or more of pressure, humidity and temperature in addition to flow. NO-containing product gas is merged with the inspiratory flow after the flow sensors. Inspiratory flow continues through a HEPA filter 214, a humidifier 216 and on to a "T" fitting 218, where sample gases are pulled, then on to the patient. FIG. 5 also includes a manual bagging circuit 220. Inspiratory gases are sourced from a blender/wall outlet/cylinder 222 and enter the ventilator cartridge 208. Flow is measured within the ventilator cartridge 208 prior to adding NO-containing gas. Gases flow through an optional humidifier 224 and on to a "T" fitting 226 where sample gases are pulled and then on to the patient.

FIG. 6 illustrates a similar system to the embodiment of the system shown in FIG. 5. As explained above, FIG. 5 depicts how the filter-scrubber-filter assemblies can be grouped into a cartridge 204, and FIG. 5 also depicts how gas sensors (176, 178, 180), selective humidity exchange tubing 174 (e.g. Nafion), a manifold, and pressure/flow sensors can be grouped into a gas sensor assembly 182. In FIG. 6, a gas sensor assembly 232 includes a pump 234 and a flow sensor 236. FIG. 5 depicts how vent flow sensors 210, 212, a bag flow sensor 223, pressure sensors, and NO injectors can be grouped into the vent cartridge 208. An optional HEPA filter 214 connects to the vent cartridge 208 to keep the vent cartridge clean. FIG. 5 and FIG. 6 further differ in pneumatic design post-plasma chamber. In FIG. 5, in both NO generation channels, a first flow-director (200a, 200b) directs product gases to either the gas sensor pack 182 or the gas scrubber cartridge 204. In the secondary channel, a second flow director directs product gases to either a vent circuit (path B) or a bag circuit (path C). In FIG. 6, the pneumatic pathway differs in that a first flow director selects between vent circuit and the sensors while a second flow director selects between shunting to the sensors and bag circuit. The pneumatic design in FIG. 6 has an advantage over the flow design of FIG. 5 due to having equal flow restriction in both channels between the plasma chamber and the vent flow injector. This relates to minimizing the flow path length and having the flow restriction of the two paths be substantially identical so that they can have similar if not identical calibration settings and NO production.

In some embodiments, a scrubber cartridge can be used for demonstration purposes. The demo device can be identified by RFID, memory device, 2-d bar code, mechanical interface, optical interface or other means by a controller to enable a demonstration mode for training purposes. In some embodiments, the demonstration scrubber cartridge is non-functional for clinical purposes.

An NO generation device, including a portable NO generation device, is expected to operate in a myriad of environmental conditions. High humidity ambient air has the potential to condense within the system when it is compressed by the pump. Condensation presents the risk of damaging sensors within the system and possibly accumulating to a point where the pneumatic behavior of a system is affected. For example, a reactant gas reservoir can fill with condensed water, effectively reducing the volume of the reservoir for compressed gas. Of further concern is the water-solubility of nitrogen dioxide which creates nitric acid in condensed water and can contribute to corrosion and degradation of internal components. This is not an issue when a system is provided with dry air from an external source.

Figure 7A:
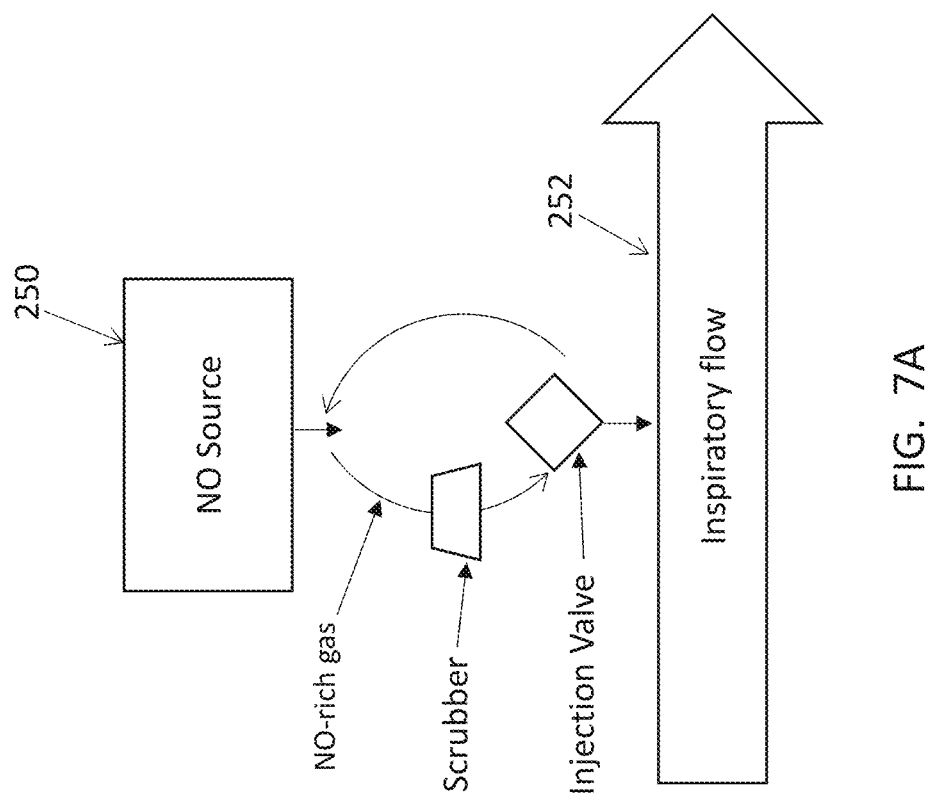
FIG. 7A, FIG. 7B, and FIG. 7C illustrate embodiments of NO generation systems having recirculation architectures.
Figure 7B:
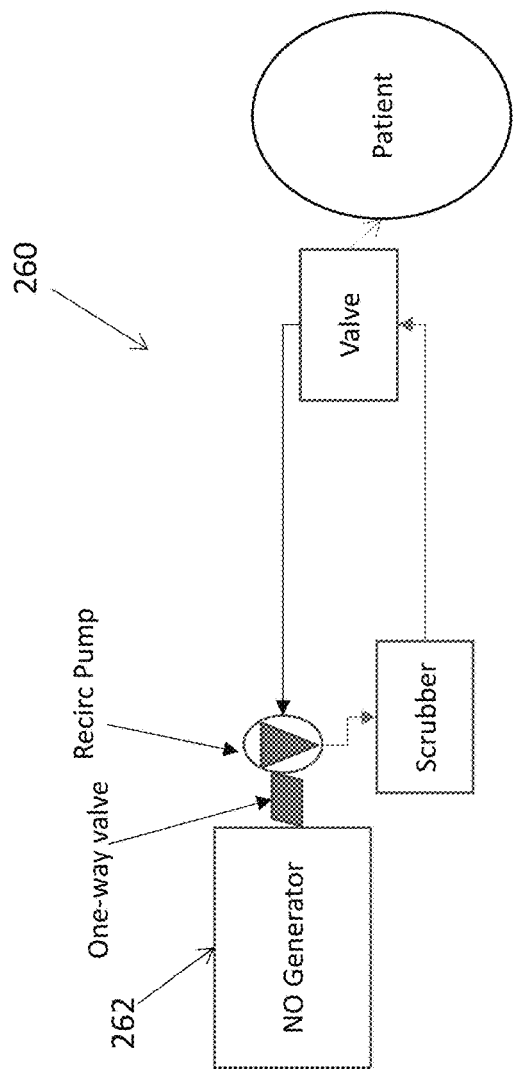
Figure 7C:
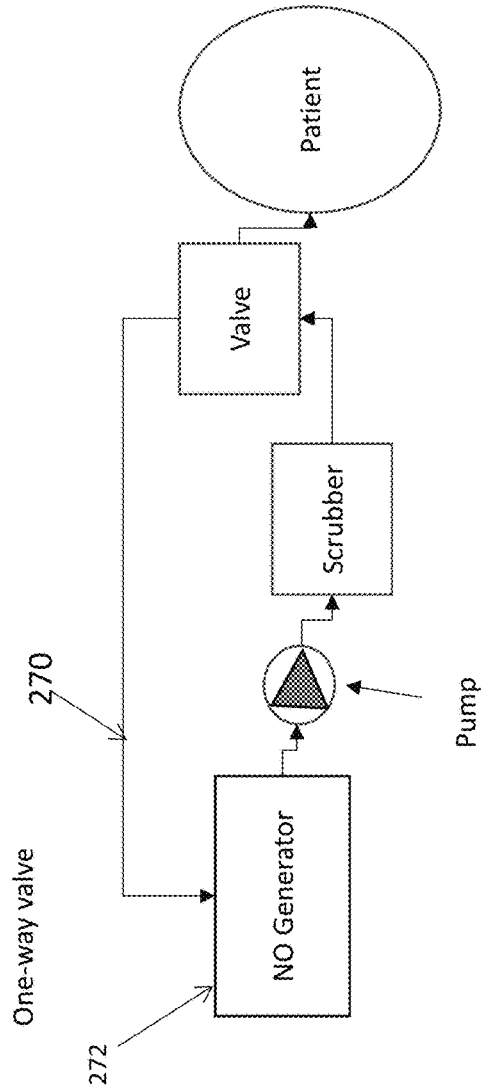

In some embodiments, a NO system can include a recirculating loop of NO-rich gas. The gas can be constantly circulating, and only a portion is diverted to the inspiratory limb. Recirculation limits residence time, so $NO_2$ formation can be limited. Moreover, gas that returns to the NO source can be "re-scrubbed" to limit $NO_2$ accumulation. As shown in FIG. 7A, in some embodiments, recirculation of gas between the NO source 250 and the point of injection 252 can be achieved. This can be used with all types of NO generation systems described herein, for example, with a remote NO-injector. FIG. 7B illustrates an embodiment of a recirculating loop 260 that continuously removes $NO_2$ from stores NO-containing gas. A valve opens to inject NO containing gases as directed by the NO generator 262. In some embodiments, the valve opens for patient inspiration. FIG. 7C illustrates an embodiment of a system where recirculated gas 270 flows back through the NO generator 272. This is acceptable because only a fraction of $N_2$ and $O_2$ is converted to NO in the plasma chamber. Thus, additional NO can be generated from the same air. The flow of NO-rich gas can be directed to the inspiratory limb by closing the injection valve on the return leg, otherwise NO-rich gas is continuously recirculating in the loop.

Humidity Management

Humidity Removal

In some embodiments, humidity management can be achieved by collecting and controlling condensed water so that it can be safely removed from the reactant gas pathway without impacting treatment. This can be achieved using a variety of techniques. For example, the NO generation system can include a humidity condensation reservoir that is configured to collect condensed water in the system. In some embodiments, a reactant gas humidity condensation reservoir can be removable so that condensed water can be drained. The humidity condensation reservoir can be located in or associated with various components of the system. For example, in some embodiments, the reactant gas reservoir can be part of the scrubber cartridge component.

Figure 8:
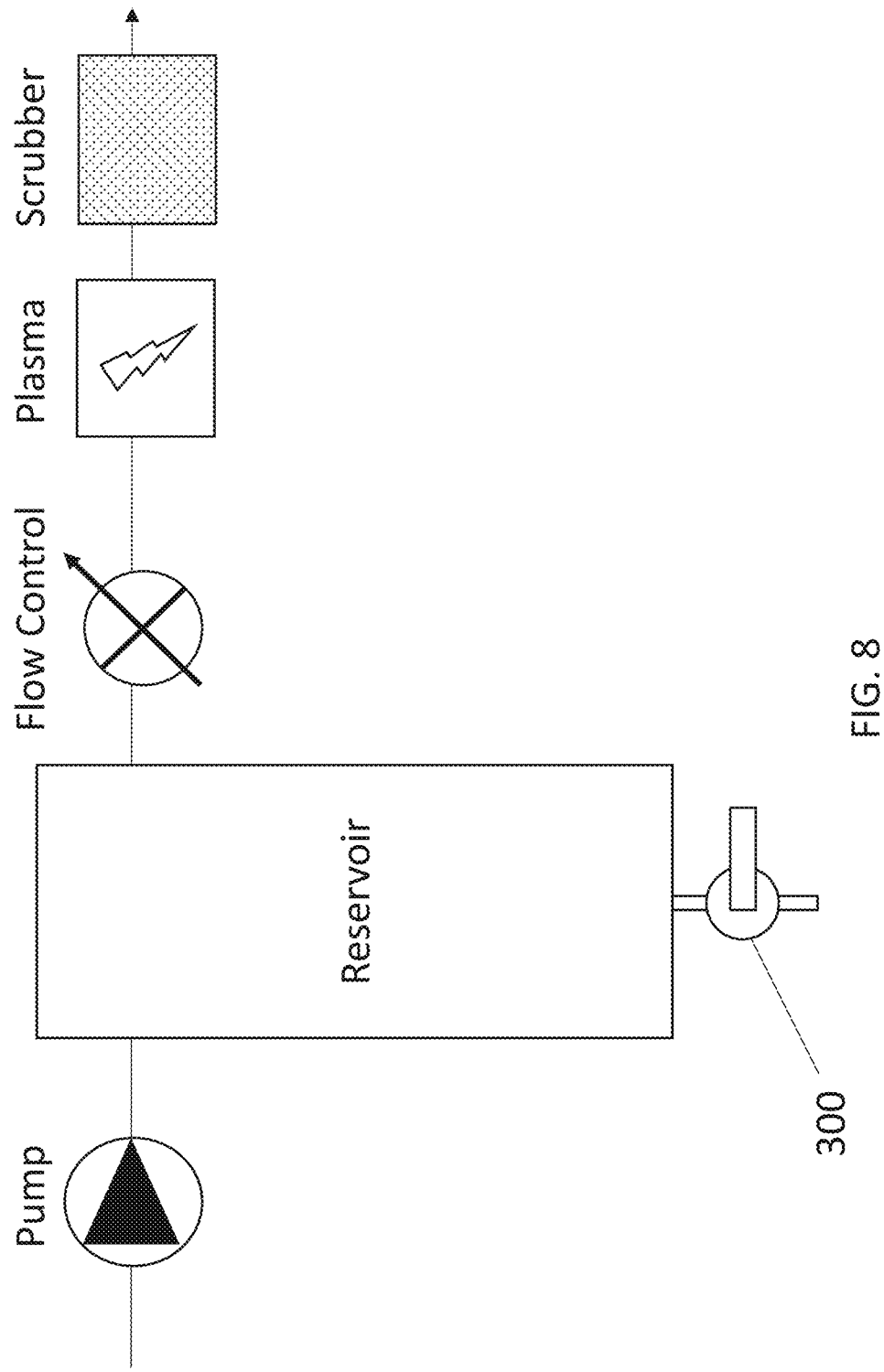
FIG. 8 shows an embodiment of a manual method of removing condensed water from an NO generation system.

In some embodiments, a drain can be located in the reactant gas pathway for removing condensed water. The drain can be manually activated (for example, a stop cock) or automatically activated (for example, a power-activated binary valve). FIG. 8 shows an embodiment of a manual method of removing condensed water from a NO generation system using a drain valve 300. In some embodiments, the drain valve is electrically controlled. In some embodiments, the valve is opened periodically. In some embodiments, the valve is opened when condensed water is sensed within the system. In some embodiments, the valve is opened only when ambient conditions and/or treatment indications present a potential for condensation within the system.

Figure 9:
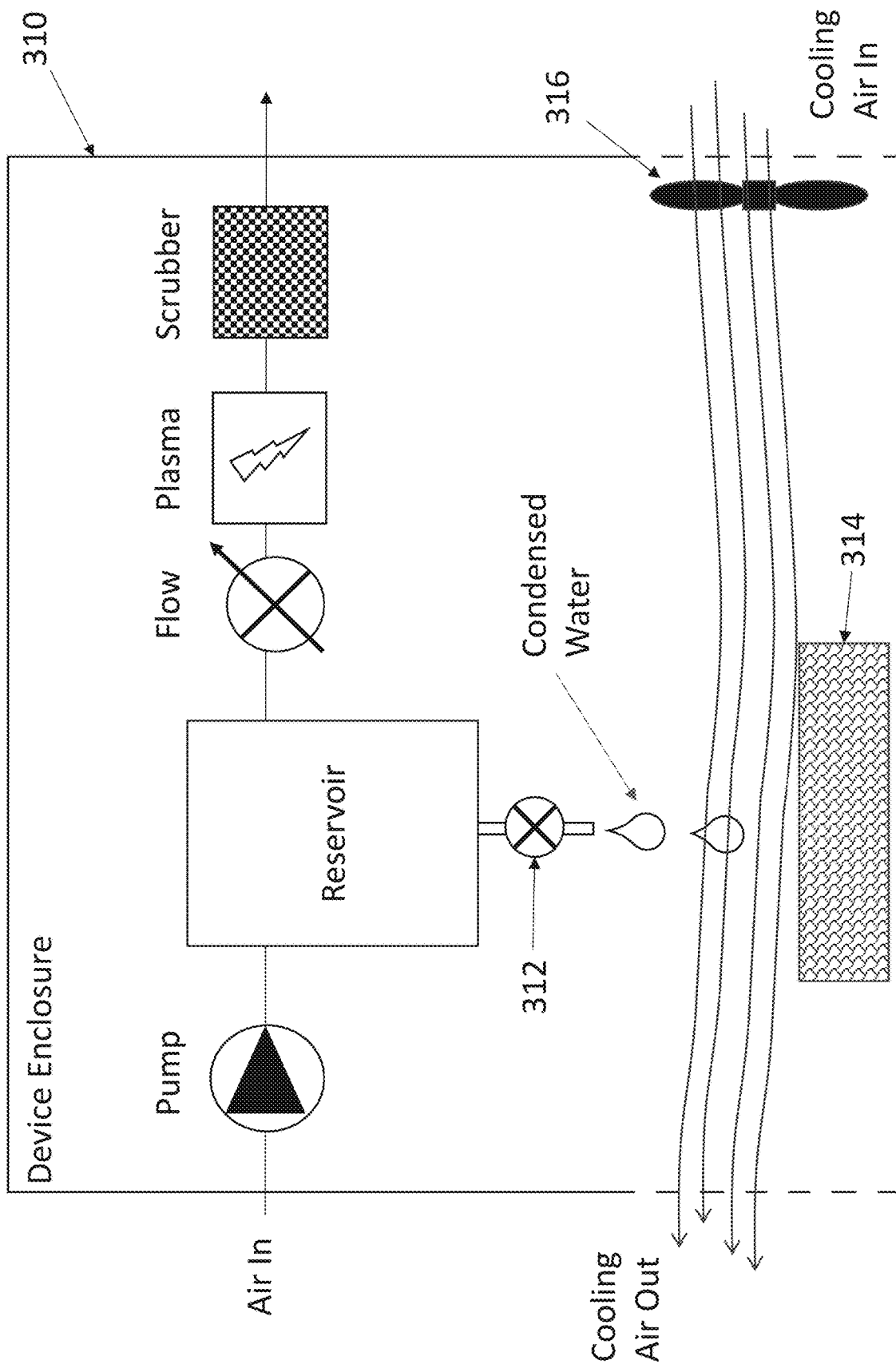
FIG. 9 shows an embodiment of a system where a drain valve releases condensed water from a pneumatic system onto a sponge.

In some embodiments, condensed water can be drained into an absorption device, such as a sponge, that can be located in the exhaust gas flow of the device cooling system. For example, warm gas flow from the box cooling system picks up water before it leaves the device enclosure. FIG. 9 depicts an embodiment of a system 310 where a drain valve 312 releases condensed water from a pneumatic system onto a sponge 314. Release can be drops of water, as shown, or managed within a tube to reach the sponge 314. A fan 316 moves ambient air through the device enclosure to cool the device. The ambient air warms within the system, increasing its water-carrying capacity. The water passes over the sponge, picking up collected water via evaporation and carries the water out of the device through vents in the enclosure.

In some embodiments, the system can include a valve at the bottom of the reservoir that provides an exit for accumulated water to exit. Pressure in the reservoir pushes the water out. The water could be directed to a device, such as a hot plate, or a warm air flow, that is configured to evaporate the water. In some embodiments, a valve is located in the reservoir, typically at the lowest location. The valve can be opened manually, automatically based on time, automatically based on moisture detection, and/or automatically based on ambient or reactant gas humidity conditions that are known to cause condensation.

It can also be possible for condensed moisture to be collected within a container for the user to drain. In some embodiments, the container can be a disposable component that is discarded once full. In some embodiments, the container is part of an existing disposable component, such as a sample gas water trap, scrubber cartridge or ventilator cartridge.

In some embodiments, condensed moisture can be directed to a pan or sponge located in a warmer and/or drier location within the system so that the water can evaporate. In some embodiments, a sponge can be placed in the flow of exhaust gases from the device cooling system.

Figure 10:
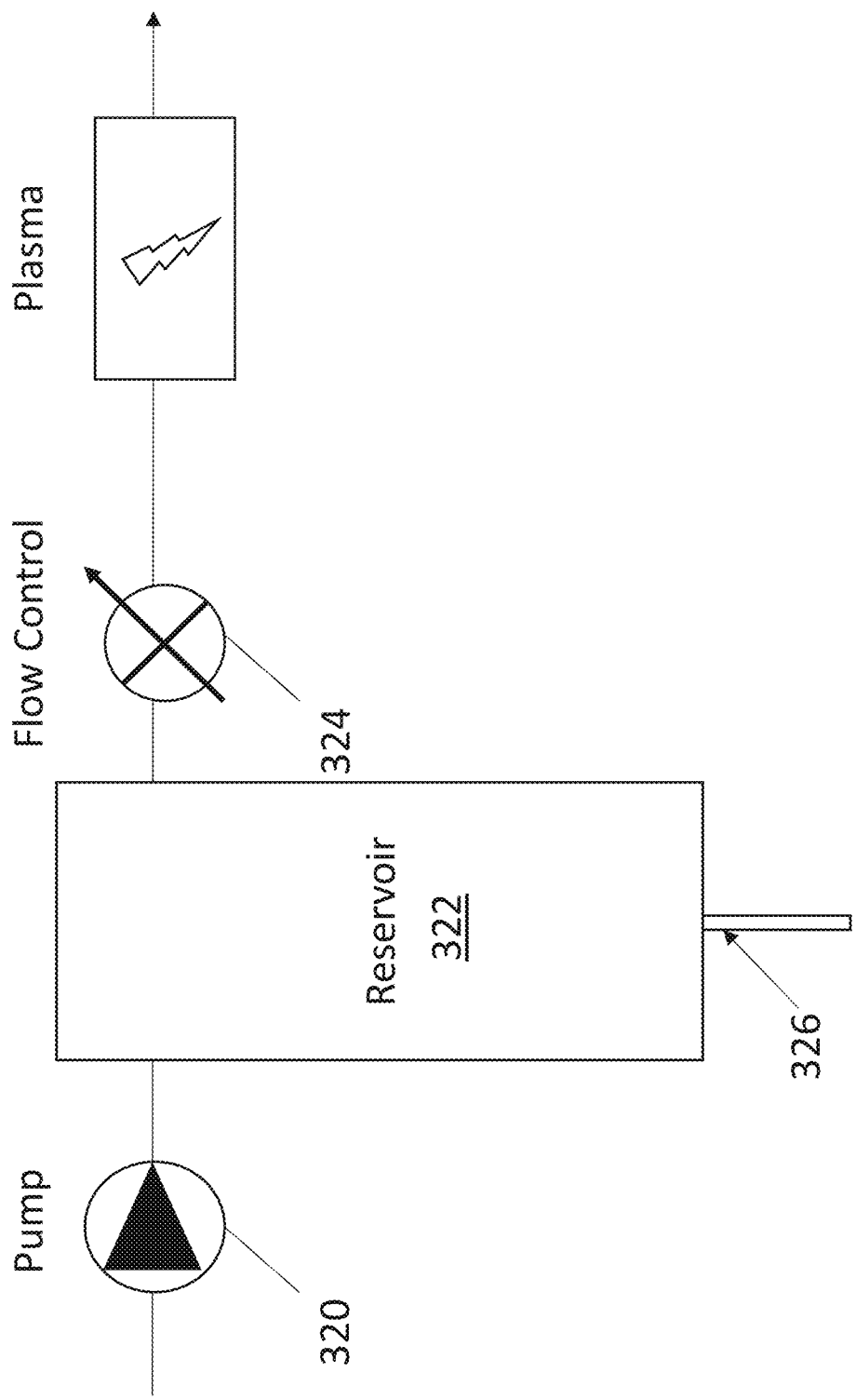
FIG. 10 shows an embodiment of a pneumatic design including a pump and pressurized reservoir.

In some embodiments, a reservoir can include an orifice that provides a constant bleed of pressure. By locating this orifice on the bottom of the reservoir, condensed water can be pushed out of the reservoir as it is created. In some embodiments, the bleed air flows at a much slower rate than the reactant gas flow towards the patient and is accounted for in either the flow controller calibration or operating program. FIG. 10 depicts an embodiment of a pneumatic design including a pump 320 and pressurized reservoir 322. An orifice 326 at the bottom of the reservoir continuously leaks air and any condensed water. Flow out of the orifice is typically a fraction of the flow through the flow controller 324. In some embodiments, the flow controller uses closed-loop flow control with the reactant gas flow rate through the plasma chamber as the control input, thereby independent of flow loses through the orifice.

Figure 11:
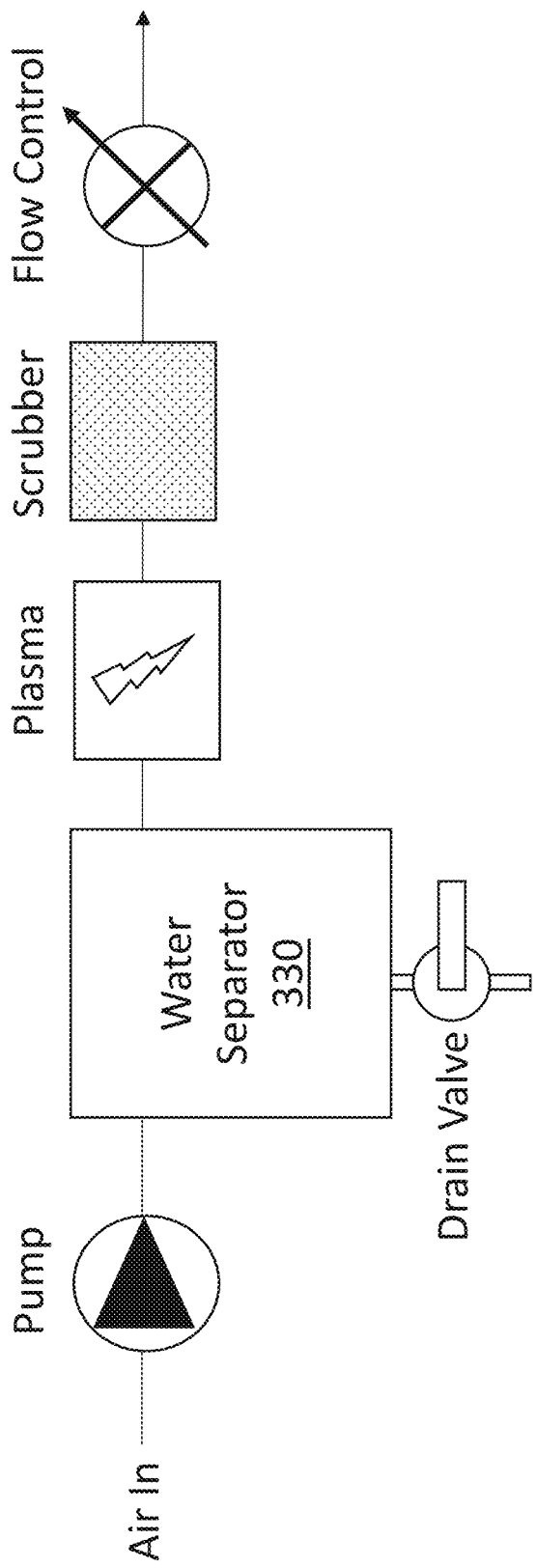
FIG. 11 depicts an embodiment that utilizes a water separator post-pump to remove condensation from the reactant gas.

FIG. 11 depicts a NO generation design with a water separator 330 that removes water from reactant gas as it enters the system. A water separator can be effective in locations prone to condensation within the system, such as post-pump due to the increase in pressure. Water separators can also be used after a pressure drop where condensation is possible due a decrease in temperature. Significant pressure drops in a NO generation system can occur within a scrubber or across valves and critical orifices. The water separator can be many types including a stationary vane separator, a cyclone separator, multi-cyclone separator, hydrophobic membrane, an inertial centrifugal separator or a combination thereof.

Humidity Prevention

In some embodiments, humidity management can be achieved by preventing water content within the reactant gas from condensing. When humid ambient air is compressed, the relative humidity increases. One method of preventing humid gas from condensing within a NO generation system is to heat the incoming reactant gas, thereby lowering the relative humidity. So long as the reactant and product gas is maintained at sufficiently high temperature, condensation will not occur.

Figure 12:
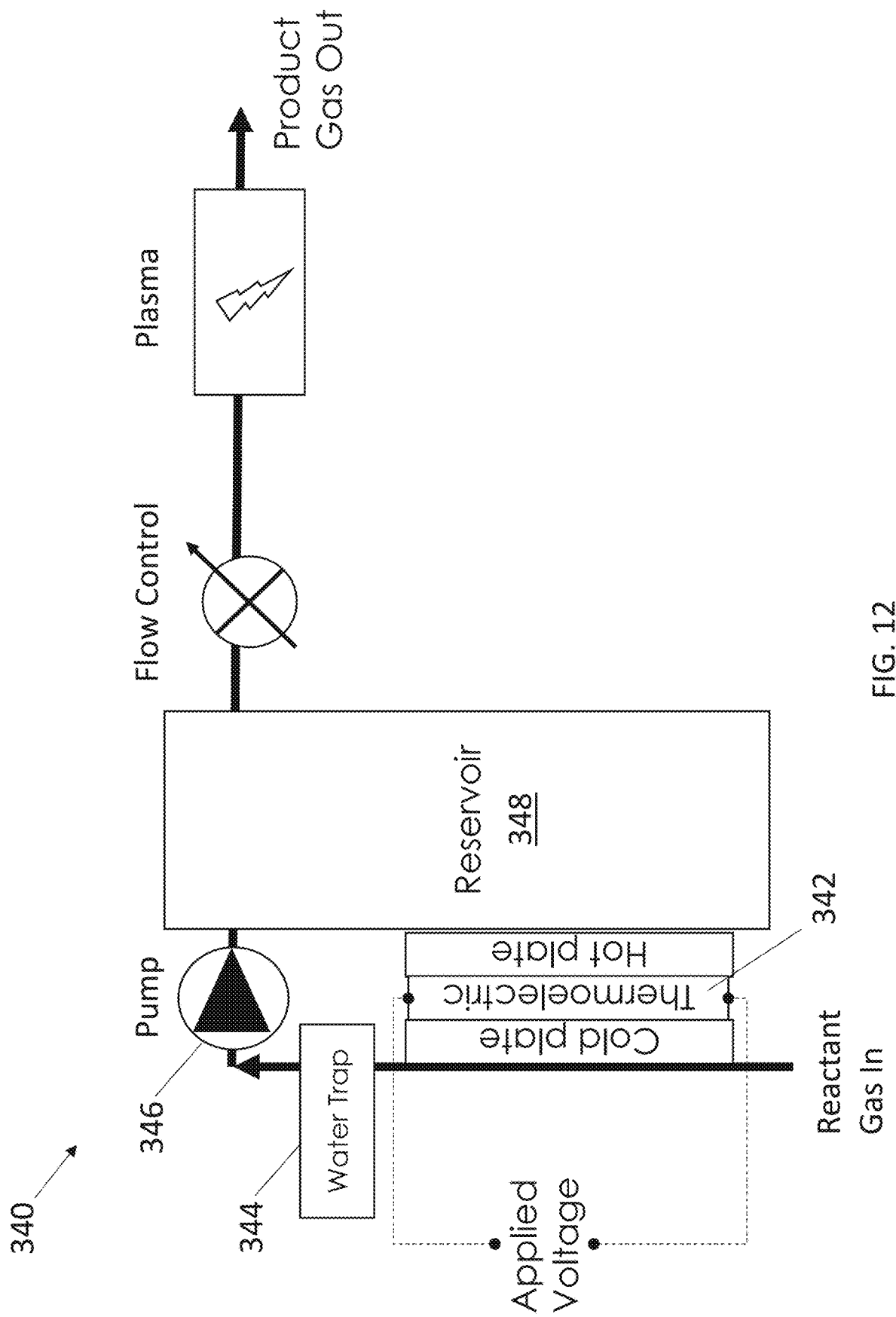
FIG. 12 shows an embodiment of an electric NO generation device that uses a thermoelectric device to simultaneously cool incoming reactant gas and heat reservoir gas.

Another approach to humidity management is to remove excess moisture from incoming reactant gas as it enters the system. In some embodiments, a thermoelectric device (a Peltier device) can be used to cool the incoming air into the system to generate condensation and dry out the incoming gas. In some embodiments, the warm side of a thermoelectric device is used to warm high pressure portion of the gas flow path (for example, post-pump) to prevent condensation. The thermoelectric device can be modulated based on ambient humidity. In some embodiments, the thermoelectric device is only powered when reactant gas humidity and system operating temperature present a potential for condensation within the system. FIG. 12 depicts an embodiment of an electric NO generation device 340 that uses a thermoelectric device 342 to cool incoming reactant gas prior to a pump 346 and heat reactant gas after the pump. Humidity within the reactant gas condenses as it is cooled and collects in a water trap 344. Gas continues through the pump and enters a reservoir 348. The thermoelectric hot plate can be in thermal communication with the pump, the conduit to the reservoir, the reservoir or a combination thereof. The potential for additional condensation is mitigated by keeping the reactant gas warm when it is under pressure. Collection of condensed water can be managed by any number of methods as described above.

In some embodiments, a heating element can be used to keep gas within the high-pressure portion of a NO generation system warm to prevent condensation. Examples of a heating element include but are not limited to a resistive heater constructed from one or more Nichrome wires, a resistive flex circuit, an exothermic chemical reaction (e.g. oxidation of iron powder), and/or a thermo-electric circuit. It will be understood that any of the heaters relative to any components of the system described herein can be used with either active control, passive control, or both to alter the humidity in at least a portion of the system. For example, any of the heaters can be functioning continuously, can be modulated either manually or automatically using sensor or other control information.

Figure 13:
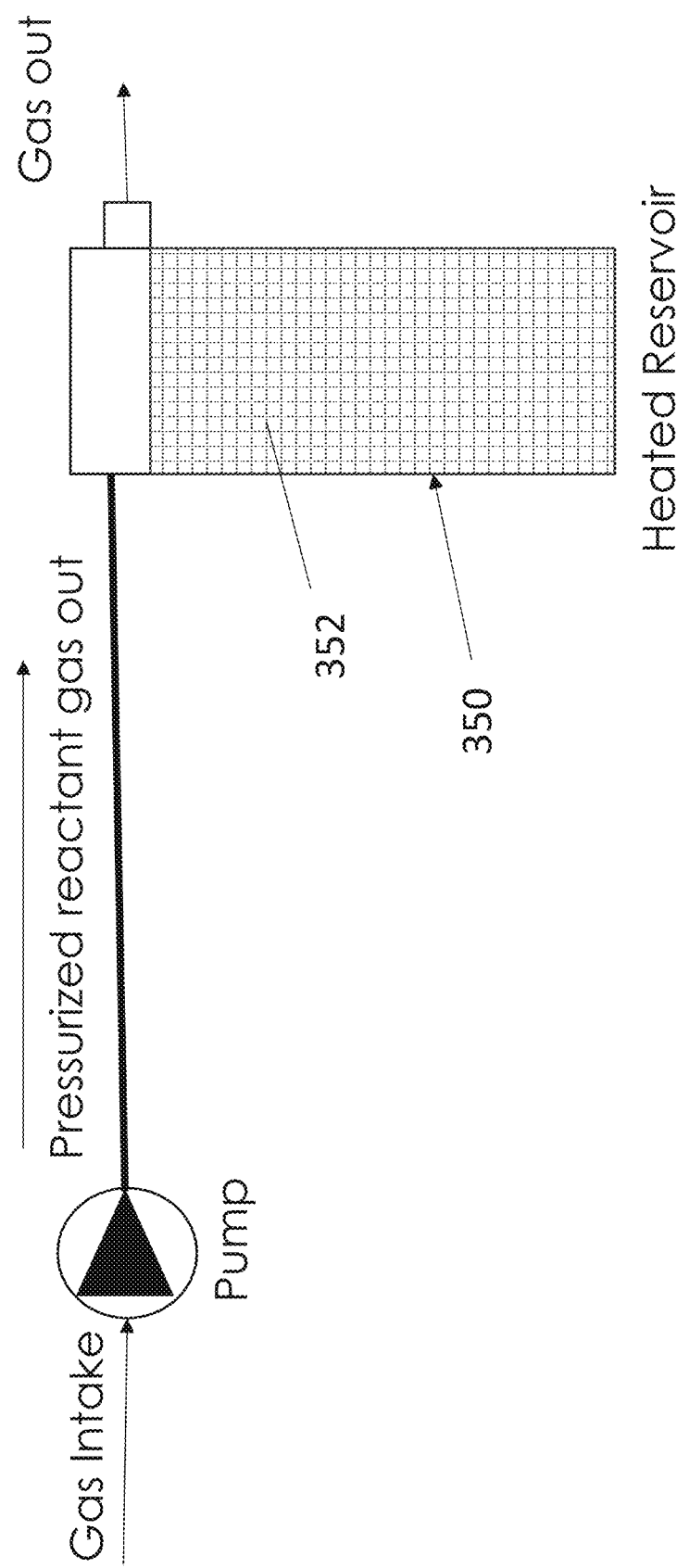
FIG. 13 shows an embodiment of a heater being applied to a reservoir.

In some embodiments, gas within the system can be pressurized by a pump and kept warm with a heater. By keeping the temperature high, the capacity of the gas to hold water remains high and water does not condense within the system. A heater 352 can be applied outside of a reservoir 350, as illustrated in FIG. 13, and/or tubing. Insulation around the tubing and/or reservoir can reduce thermal losses in turn reducing heater energy expenditure. The level of heating can be modulated based on the relative humidity, and pressure of the gas, and temperature of the gas. In some embodiments, the heater is a flex-circuit with thermal contact to the reservoir. In some embodiments, the heater is located within the reservoir and or pneumatic passageways. Various heat sources can be used, including resistive heaters and/or heat exchangers. In some embodiments, warmed fluid passes through heat exchanger located within the reservoir to warm gas within the reservoir. In some embodiments, the heat exchanger resembles a radiator with fins for large surface area and thermal contact.

In some embodiments, the internal cooling system of a nitric oxide generator can be modulated to maintain an internal enclosure temperature above a threshold to prevent humidity condensation within the reactant gas pathway. In some embodiments, the system cooling fan speed is modulated to maintain an internal box temperature that is greater than 10 degrees Celsius above an ambient temperature. In some embodiments, a higher temperature difference is maintained due to higher pressure within the gas pathway. In some embodiments, the temperature of the reactant gas can be increased without increasing the pressure as the flow controller will actively compensate for the increase in pressure to maintain a target mass flow rate.

In some embodiments, the gas pathway is actively heated to prevent condensation of water content within the system. In some embodiments, the gas heater is energized based on one or more of the following parameters: gas relative humidity, gas temperature, gas pressure, ambient air temperature, and/or ambient air relative humidity. Depending on the NO generator architecture, these techniques apply to the reactant gas, product gas or both.

Figure 14:
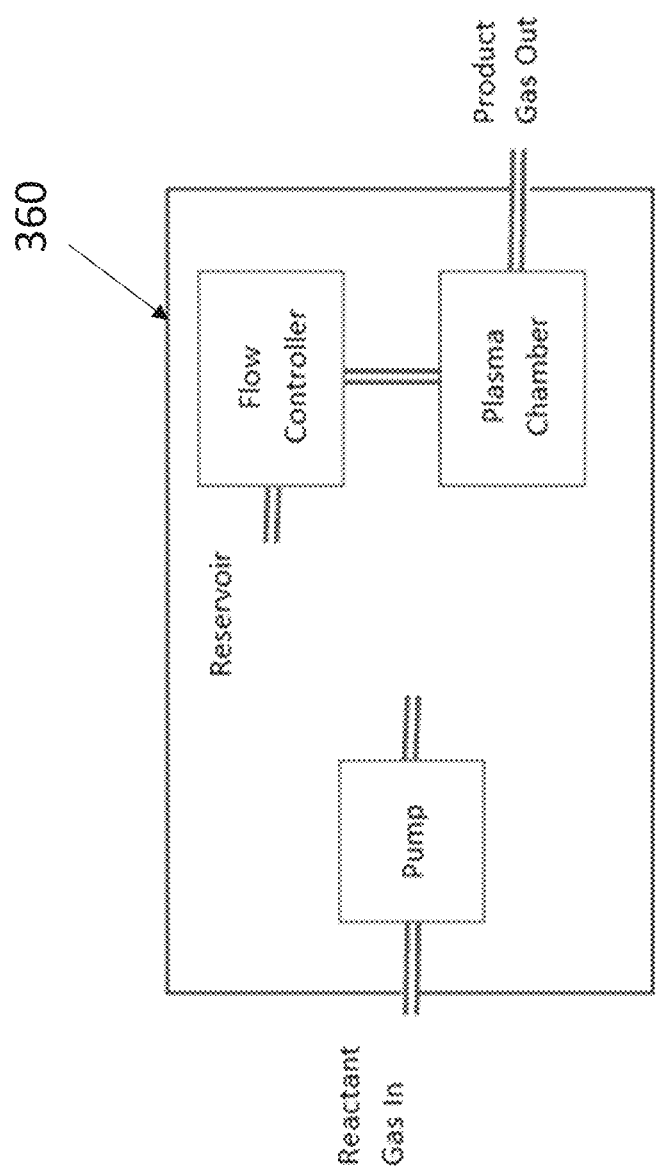
FIG. 14 shows an exemplary embodiment of a gas reservoir having heat generating components within the reservoir.
Figure 15:
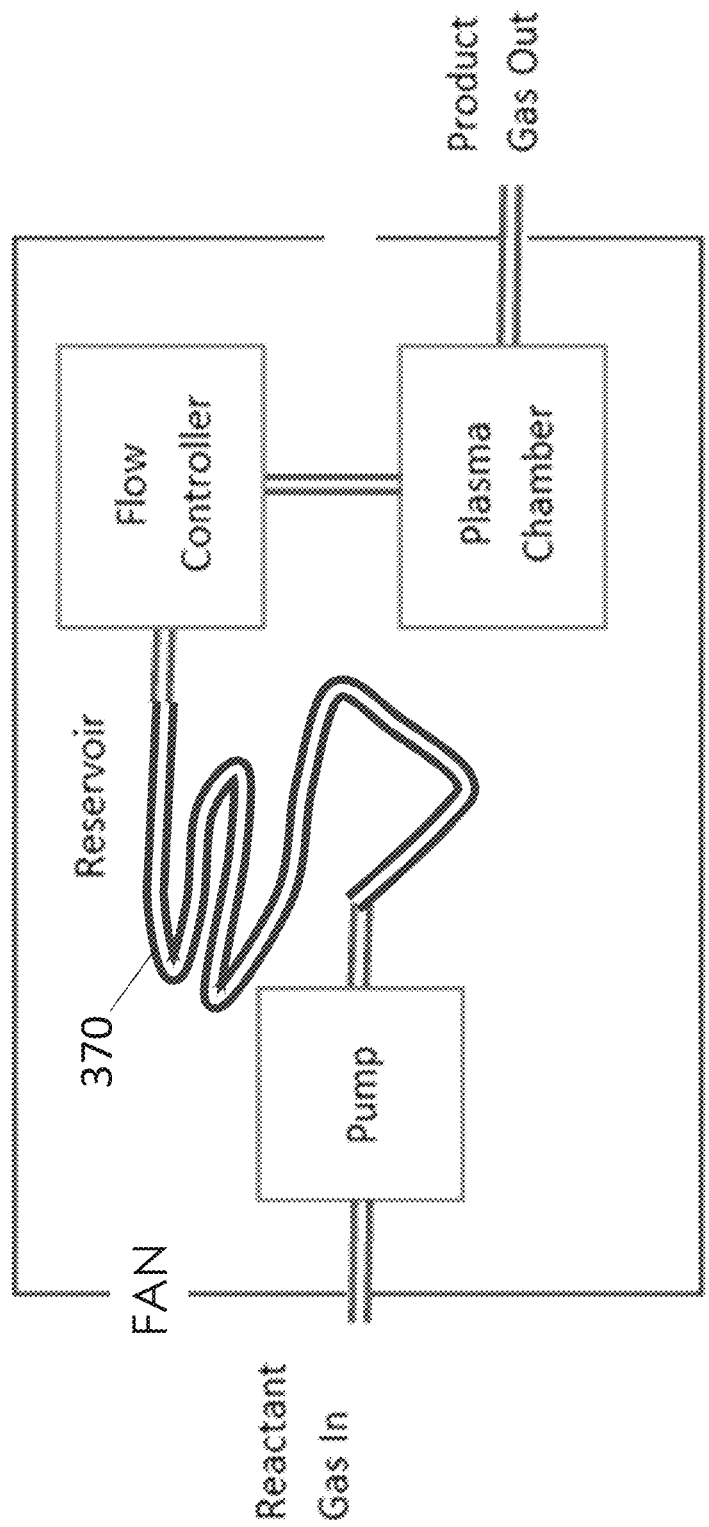
FIG. 15 shows an exemplary embodiment of a gas reservoir having heat generating components within the reservoir.
Figure 16:
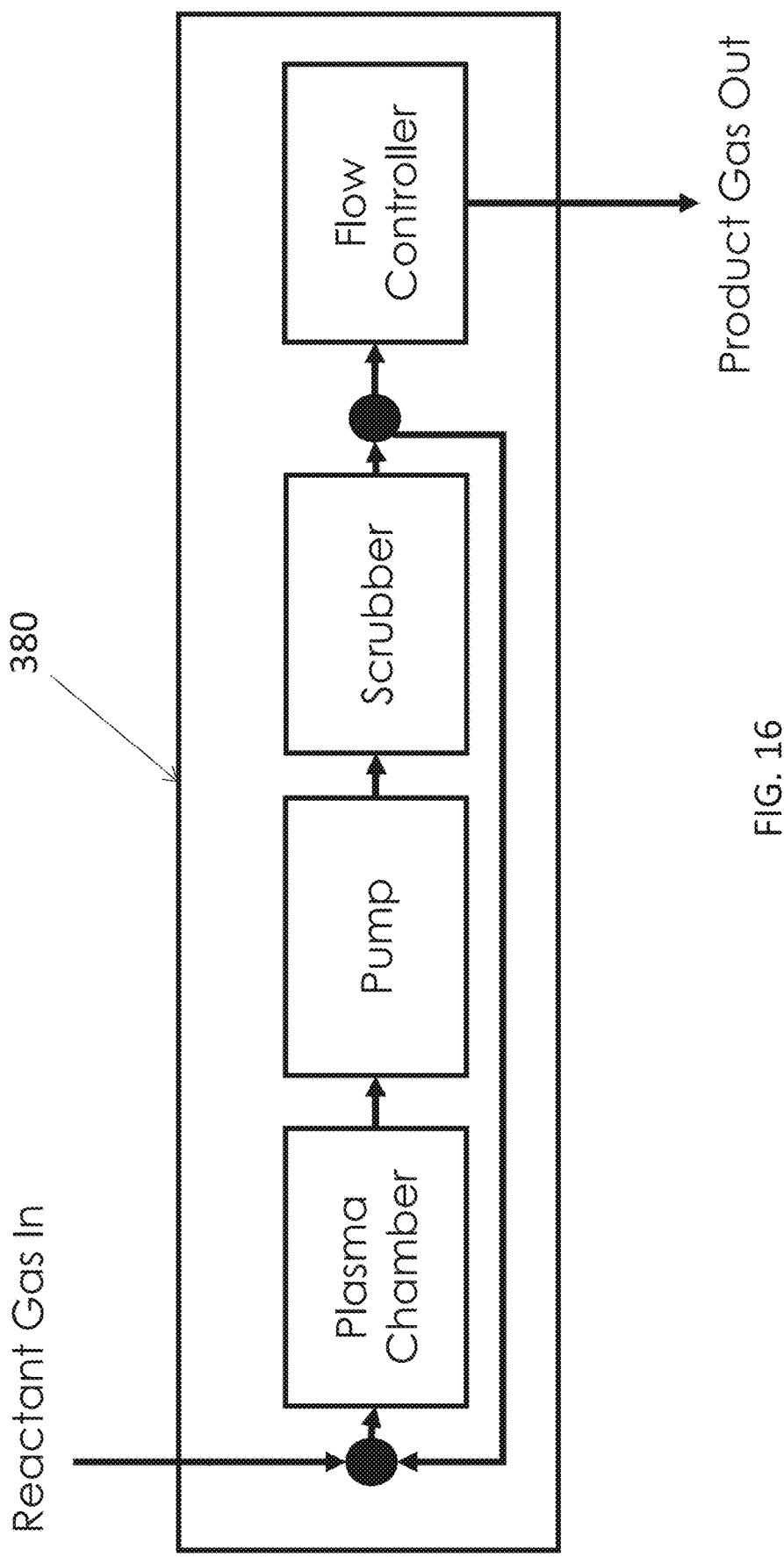
FIG. 16 depicts a NO generation device with recirculation architecture with an enclosure surrounding heat generating components.

In some embodiments, the temperature of a gas pathway is elevated by waste heat from other components of the system to inhibit water condensation within the pneumatic pathway. Components that generate waste heat include but are not limited to pumps, plasma chambers, valves, heaters, and flow controllers. In some embodiments, the reservoir is in thermal contact with the pump and/or plasma chamber to heat the reservoir. In some embodiments, as shown in FIG. 14, the reservoir and pump and/or plasma chamber are thermally isolated from other parts of the device to retain heat. In some embodiments, the pump, flow controller and plasma chamber reside within a chamber that serves as a reservoir 360. In some embodiments, insulation is wrapped around all or part of the reservoir and plasma chamber and/or pump to maintain heat within the reservoir. In some embodiments, as shown in FIG. 15, gas flows through a tube or heat exchanger 370 within a chamber or zone that is heated at least in part by waste heat of device components. In some embodiments, the gas tube passing through the heated zone is comprised of a humidity exchange membrane material that transports water from the gas to the exterior of the tube. FIG. 16 depicts a NO generation device with recirculation architecture with a thermal enclosure 380 surrounding heat generating components to elevate the temperature of gas within the system and prevent condensation.

Figure 17:
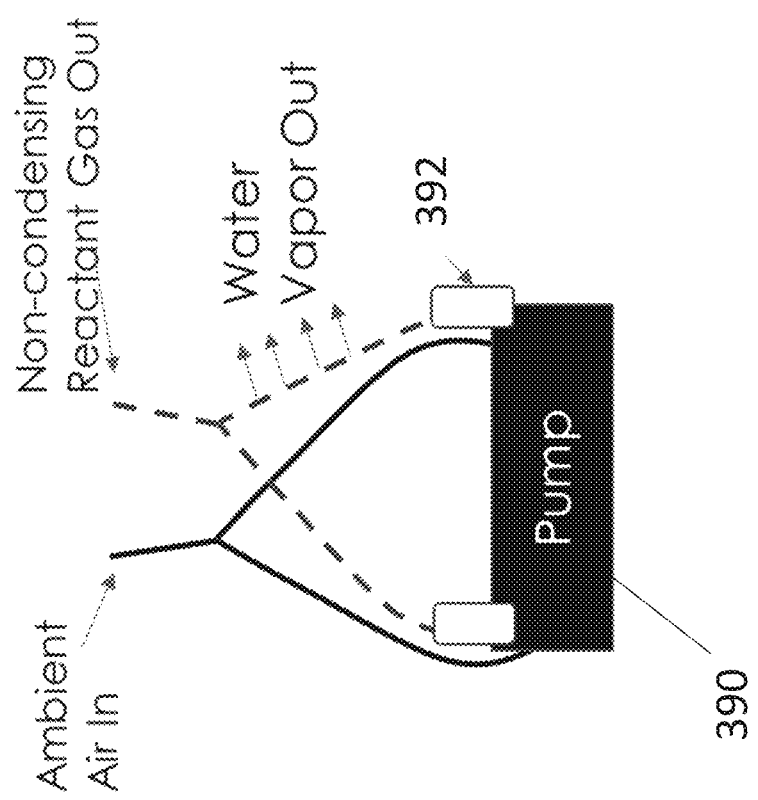
FIG. 17 shows an embodiment of a dual chamber, reciprocating pump.

FIG. 17 illustrates ambient air as it enters both ends of a dual chamber, reciprocating pump 390. It will be understood that any type of pump can be used and that, owing to the ideal gas law, gas temperature increases when gas pressure increases. Compressed gas exits each end of the pump. Insulation 392 is located on the outlets of the pump to keep heat within the gas to prevent condensation. After exiting the pump through the outlets, compressed gas passes through humidity exchange membrane tubing in which water vapor exits the tubing due to the elevated vapor content within the tube with respect to outside the tube. Non-condensing gas exits the tubing and can be stored in a reservoir or transferred directly to other parts of the system, such as the flow controller or plasma chamber.

In some embodiments, a selective humidity exchange membrane tubing (e.g. Nafion) can be used to transport gas from the pump to a reservoir to humidify or dehumidify the gas depending on the relative humidity of the intake air. It will be noted that the reservoir in many of the following embodiments can be an optional component. Humidity exchange membrane tubing functions by transporting water from one surface (e.g. inner surface) to another surface (e.g. outer surface) to equalize the partial pressure of water on each side. In some embodiments, insulated fittings are placed at connective fittings to keep heat generated by the pump and gas compression within the gas to further prevent condensation. Various factors relating to the selective humidity exchange membrane and the reactant gas affect the use of the tubing. For example, the length of the humidity exchange membrane tubing governs the surface area for moisture exchange. Water transfer out of the gas increases with elevated temperature of gas inside the membrane.

Figure 18:
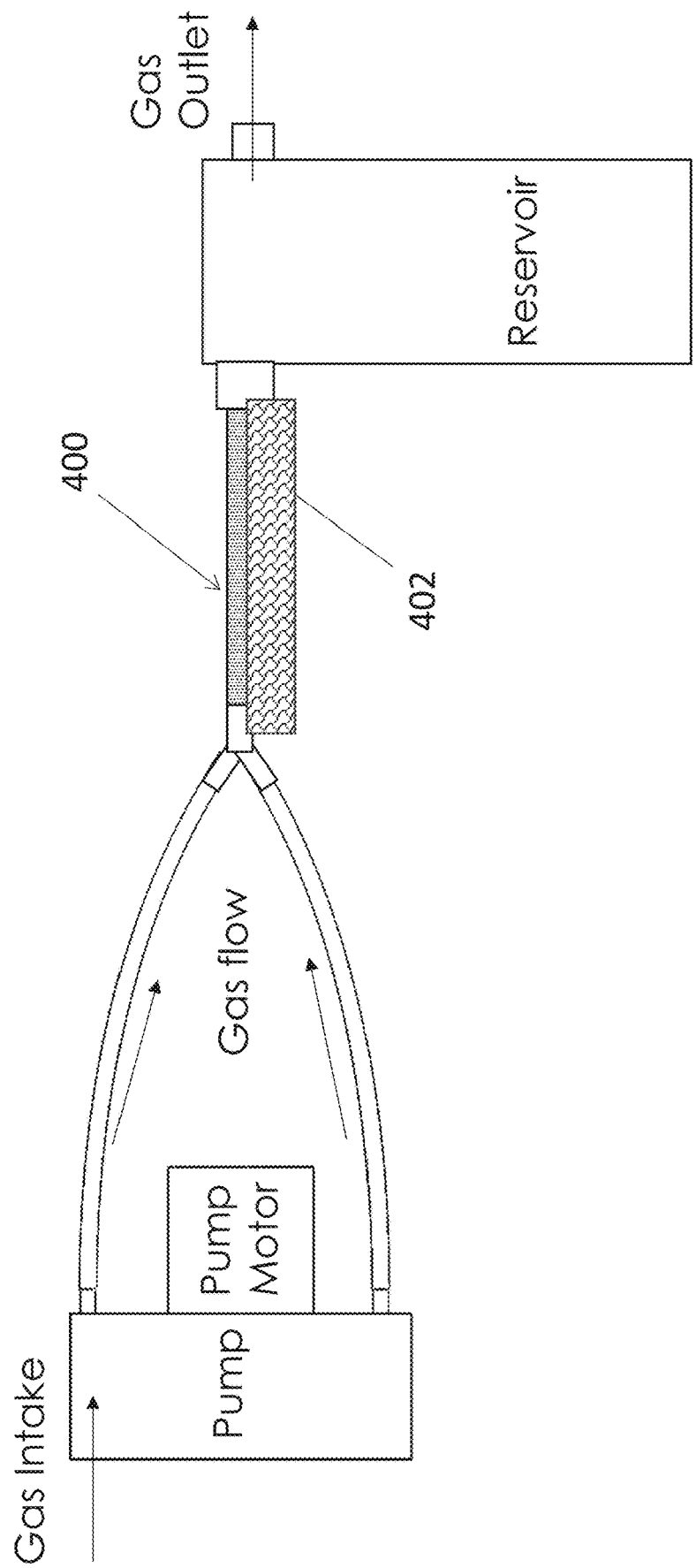
FIG. 18 shows an exemplary embodiment of a system that includes a selective humidity exchange membrane material in proximity with desiccant.

Water transfer out of gas increases with ventilation of external surface of the humidity exchange membrane. Water transfer out of gas increases with decreased pressure outside of the membrane. Water transfer out of the gas increases with increased pressure inside the membrane so long as condensation does not occur. Water transfer out of gas can be increased by embedding the membrane tubing in desiccant. In some embodiments, selective humidity exchange membrane 400 (SHEM) material can be in proximity with desiccant 402, as shown in FIG. 18, or air that has been dried by desiccant. The dry gas collects water from the surfaces of the SHEM thereby drying the gas within the SHEM.

Figure 19:
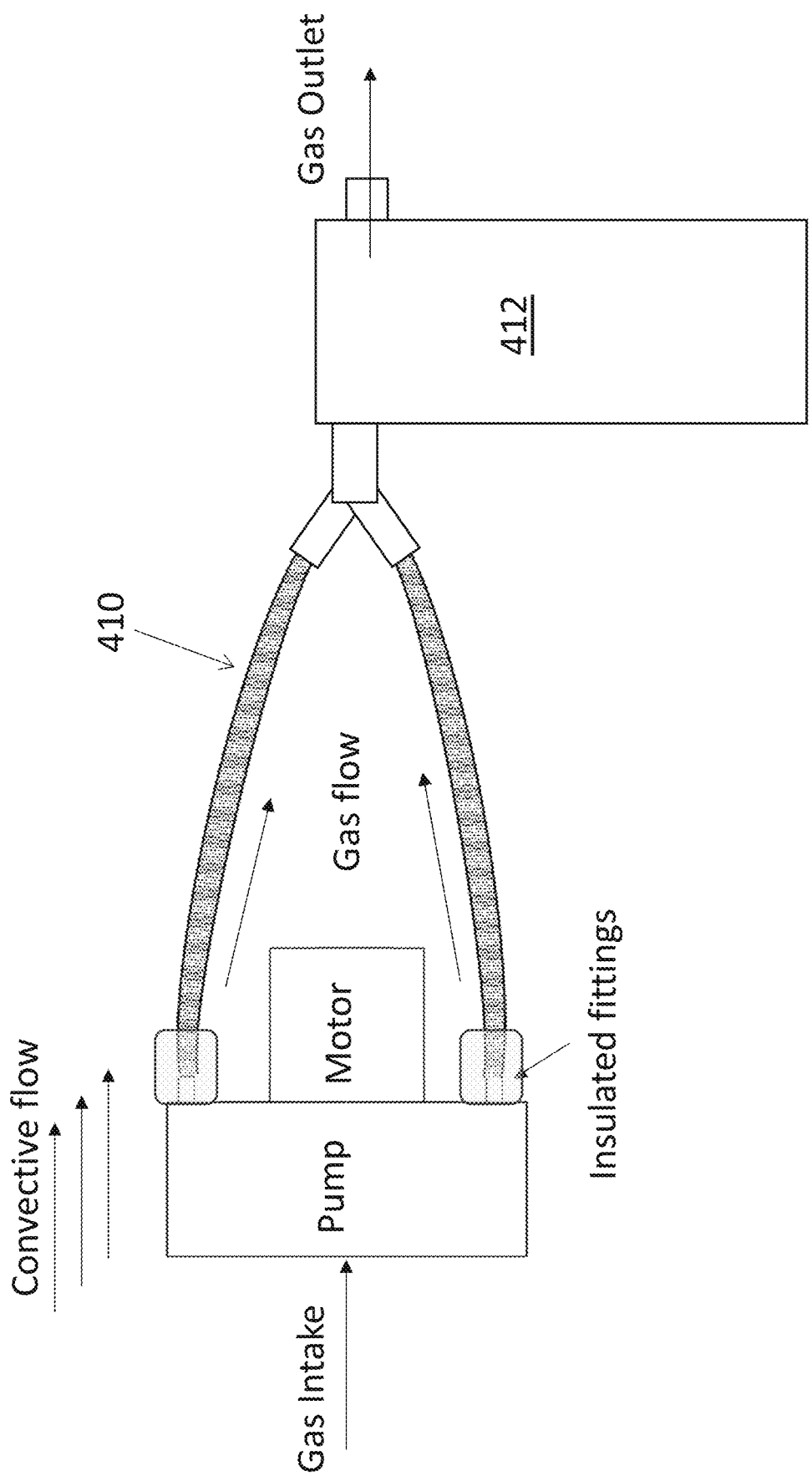
FIG. 19 shows an exemplary embodiment of a system that keeps compressed gas warm and permits humidity exchange with air circulating outside the system.

FIG. 19 illustrates an exemplary system that keeps compressed gas warm with insulated fittings followed by selective humidity exchange membrane to transfer water from the compressed gas to a ventilation flow. As shown in FIG. 19, non-condensing gas exits the SHEM tubes 410 and can be stored in a reservoir 412 at pressure or sent directly to other parts of the system. In some embodiments, the SHEM tubes are located in a high ventilation flow region of the device enclosure, such as the location where box cooling air exits the enclosure.

Figure 20:
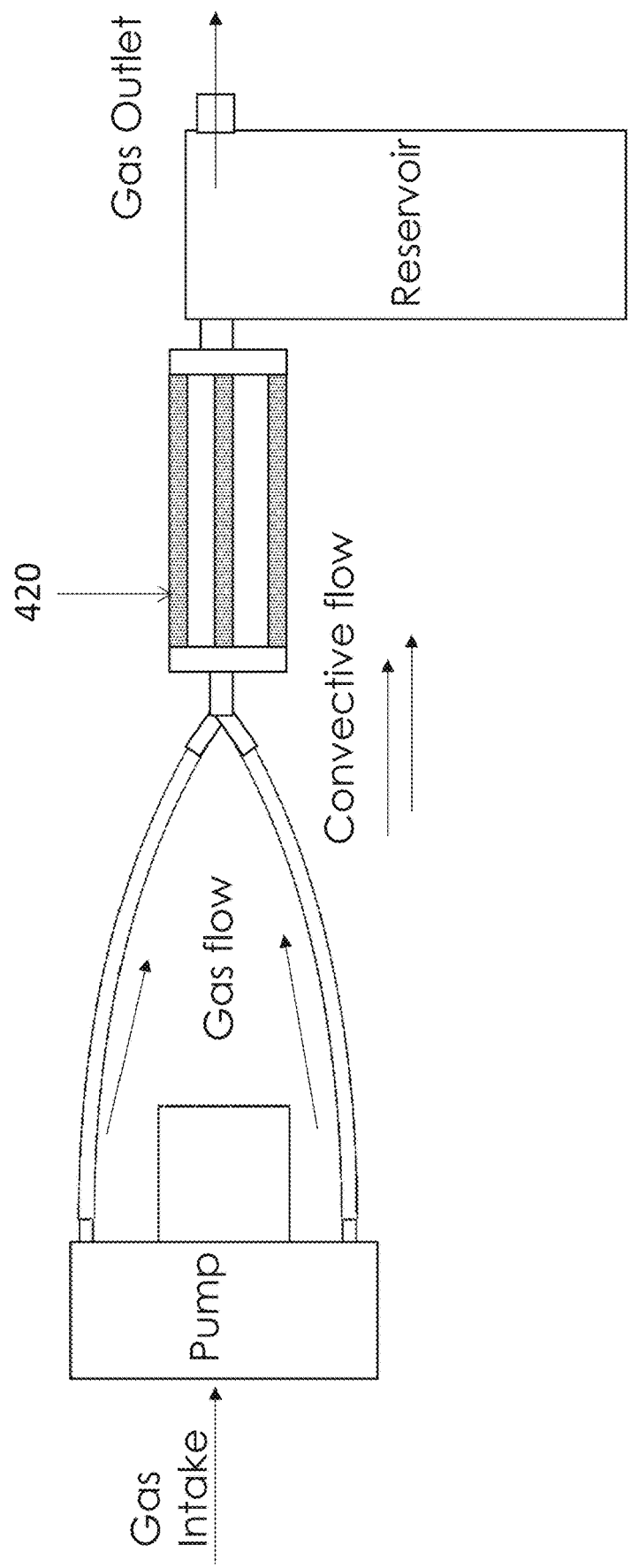
FIG. 20 shows an exemplary embodiment of a system that includes multiple lengths of selective humidity exchange membrane being utilized in parallel.

In some embodiments, multiple lengths of selective humidity exchange membrane 420 are utilized in parallel, as shown in FIG. 20, to increase surface area and decrease flow restriction. A convective flow collects water vapor from the SHEM surfaces and carries it out of the device enclosure. The internals of a NO generation device are typically warmer than ambient due to the electrical components that produce heat. The increase in temperature over ambient enables the ventilation gas to carry additional water.

Figure 21:
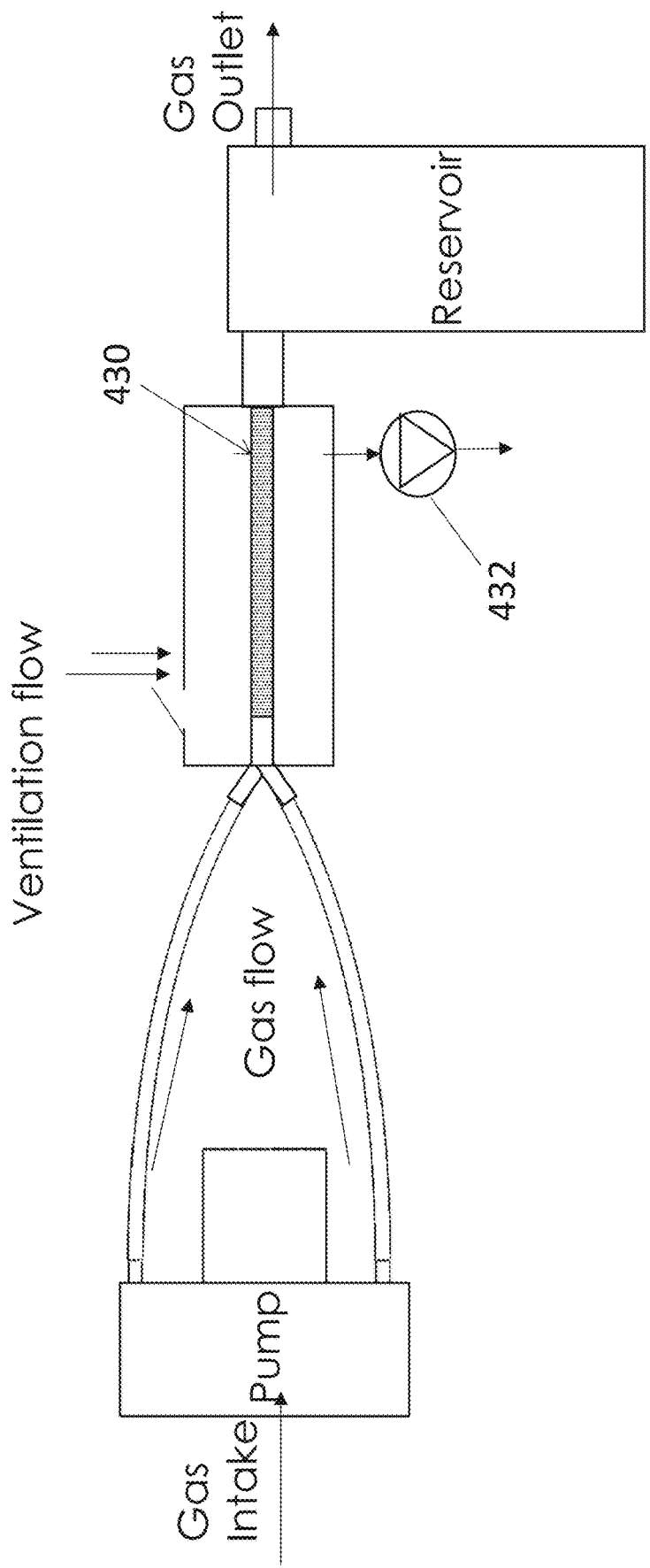
FIG. 21 shows an exemplary embodiment of a system that lowers the pressure around humidity exchange tubing to increase water transfer out of the gas flow by pulling gas through an enclosure around SHEM tubing.

In some embodiments, as illustrated in FIG. 21, a vacuum pump 432 can be used to draw gas through an enclosure around the SHEM 430 tubing. An orifice on the inlet of the enclosure limits gas flow, thereby reducing the pressure within the enclosure to below ambient. This effect increases the pressure gradient across the membrane, increasing water transport from the pressurized reactant gas to the ventilation flow. The level of vacuum within the enclosure can be modulated by pump effort and/or the size of one or more orifices. When ambient air is sufficiently dry to begin with, the vacuum pump can be turned off to decrease water removal from the reactant gas. In some embodiments, the orifice is closed in addition to turning off the vacuum pump when water removal from reactant gas is not needed. In some embodiments, the vacuum pump is modulated to provide varying degrees of water removal.

Figure 22A:
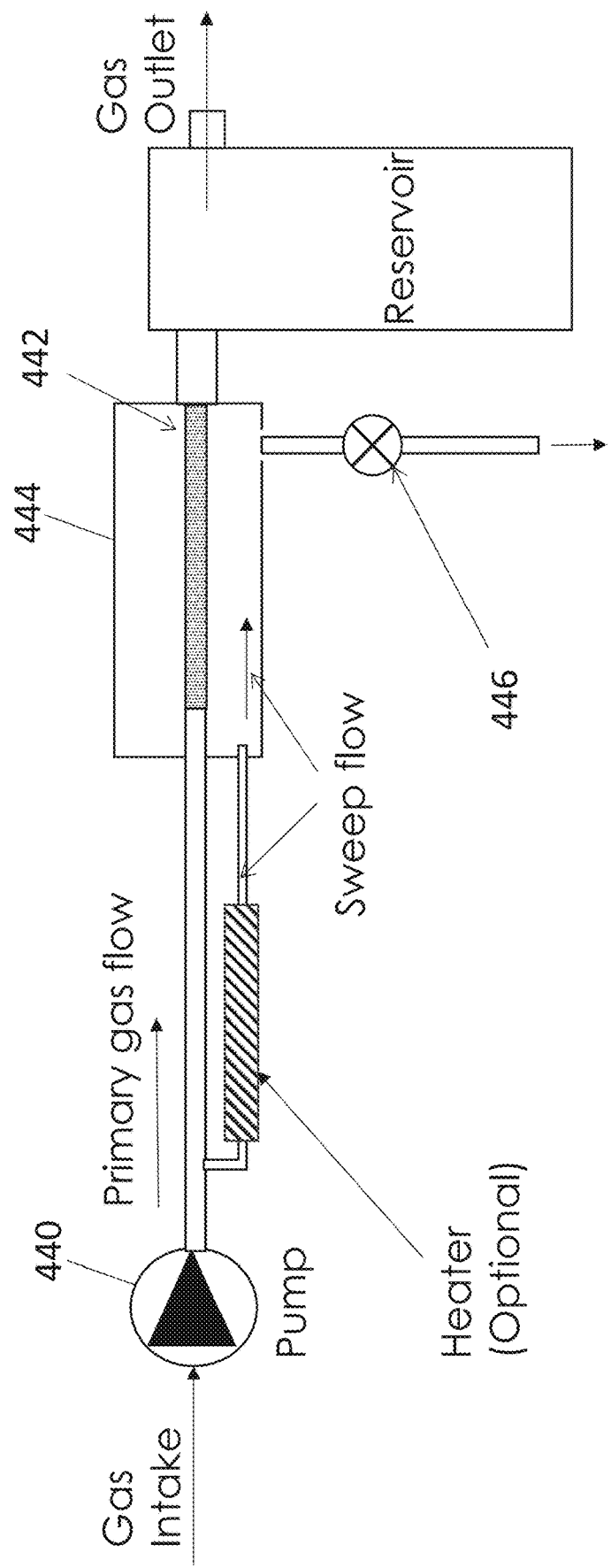
FIG. 22A and FIG. 22B show embodiments of a bifurcated gas flow from a pump that utilizes a sweep flow to remove humidity from a primary flow.
Figure 22B:
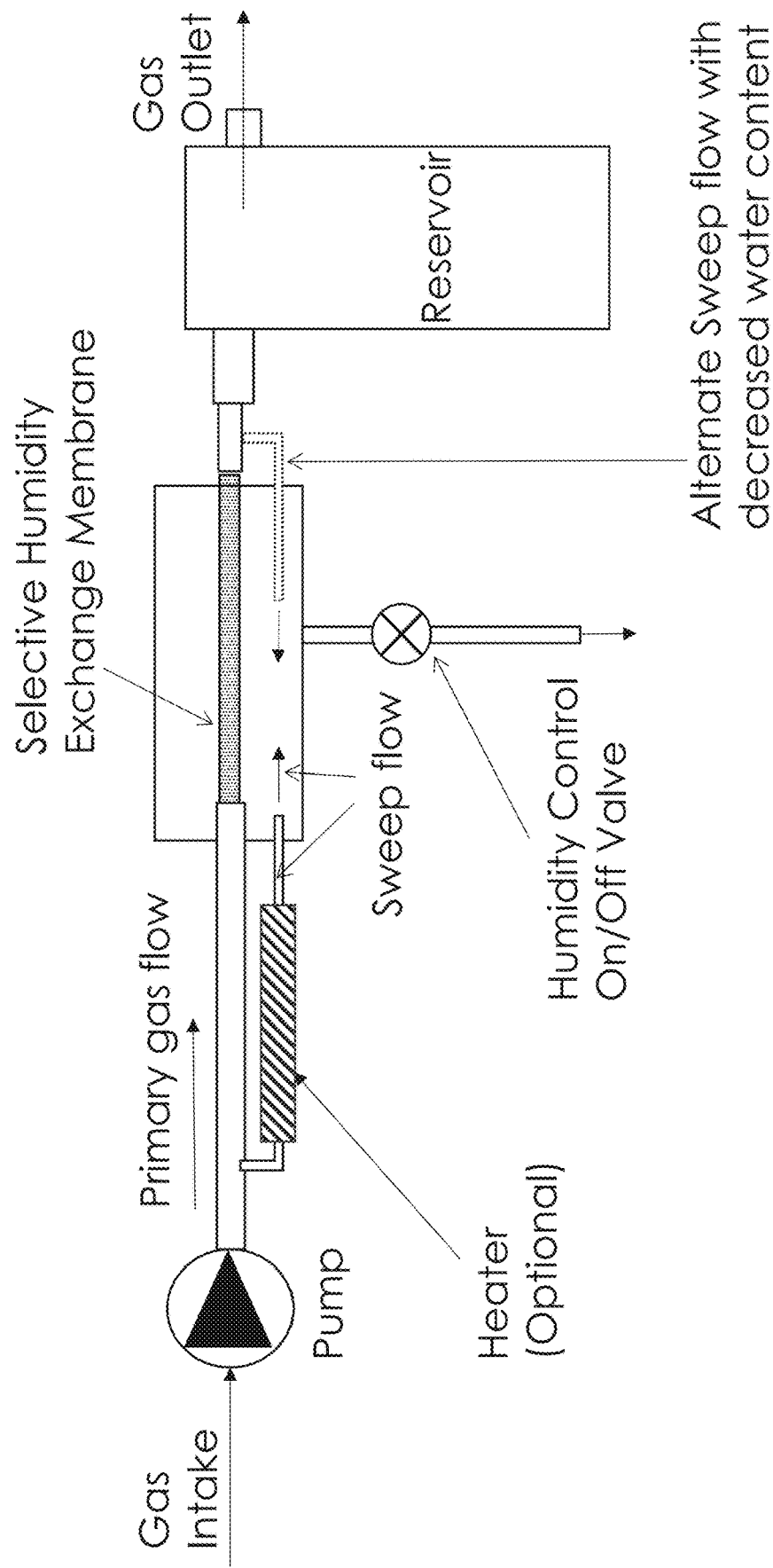

In some embodiments, as illustrated in FIG. 22A, gas flow from a pump 440 can be bifurcated into a primary flow and a sweep flow. The pressurized primary flow passes through a selective humidity exchange membrane tube 442 located within an enclosure 444. The sweep gas flow is released into the enclosure and passes through the enclosure 444, picking up water content from the surfaces of the SHEM tubing. The sweep gas exits the enclosure through a humidity control valve 446. In the event that humidity control is not required, the valve can be closed, thereby equalizing the pressure inside and outside the SHEM tubing and halting water transport. The valve type can vary. For example, the valve can be a binary valve or a proportional valve. The sweep gas flow can be controlled by modulating the flow through the enclosure exit with the valve. In some embodiments, the sweep gas flow can be diverted from the main gas flow after the SHEM (not shown), providing improved performance because the sweep gas has lower water content. FIG. 22B illustrates a system similar to the one in FIG. 22A having a primary and sweep flow, and a humidity control valve, but also includes an alternative sweep flow with a decreased water content.

Figure 23:
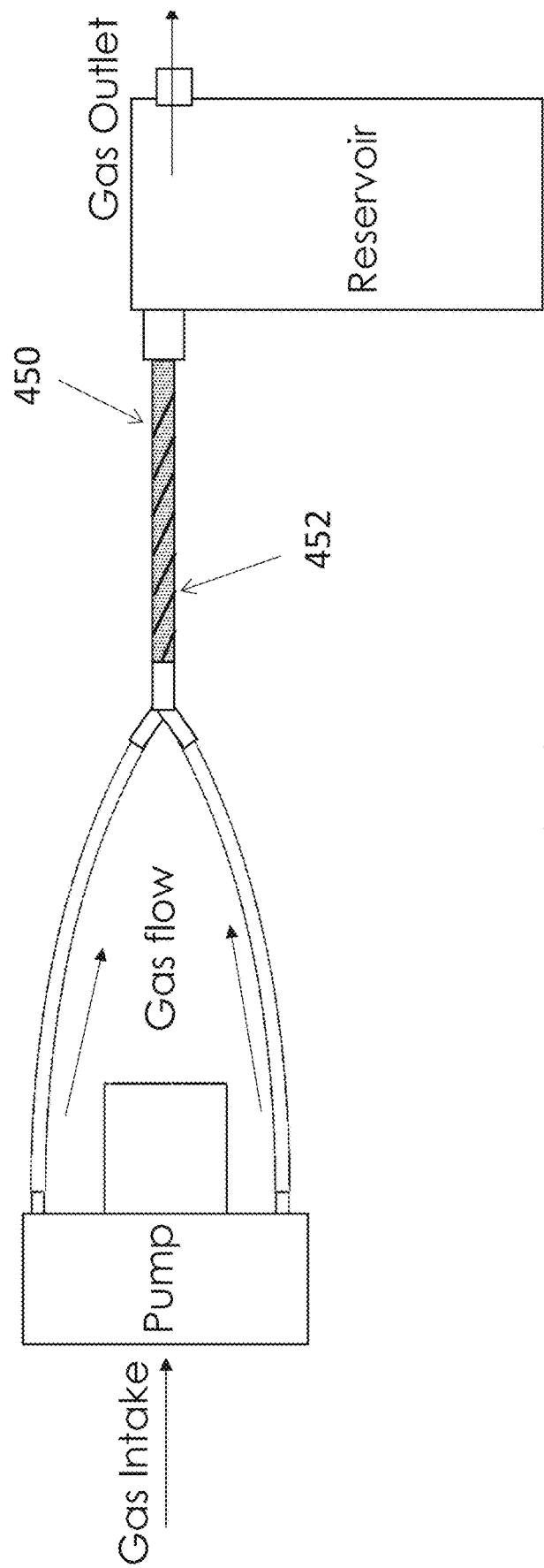
FIG. 23 shows an exemplary embodiment of a system that includes SHEM tubing with heated external surfaces.

At times, ambient conditions present dry reactant gas to a NO generation system. Dry reactant gas can shorten the life of a scrubber, such as a soda lime scrubber, which requires water as part of the $NO_2$ sequestration process. At such times, it is desirable to retain what water content there is in the reactant gas and not dry it further. In some embodiments, a pump collects ambient air, compresses it and sends it into a SHEM tubing 450. The external surfaces of the SHEM tubing are heated using a surface heater 452, as illustrated in FIG. 23, making the SHEM polymer retain more water, slowing water transport out of the reactant gas. In cases of high ambient humidity, the heater is turned off and the SHEM tubing transports water out of the reactant gas. Water vapor from the surfaces of the tubing is carried out of the NO generation device via box cooling.

Figure 24:
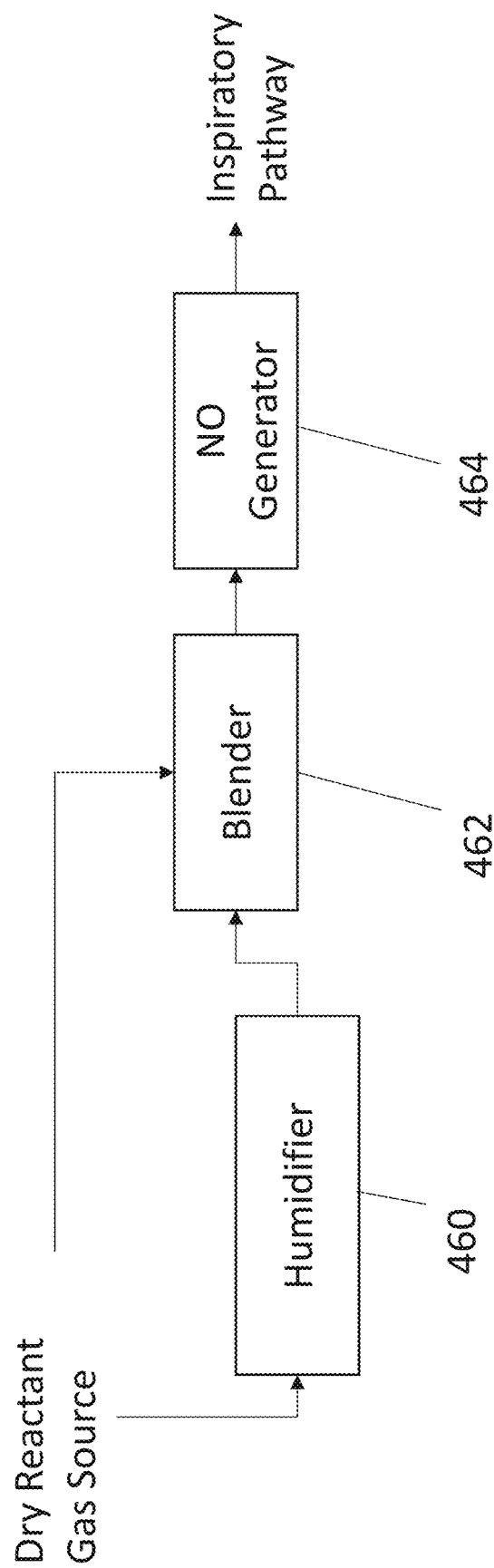
FIG. 24 depicts a system that can control the humidity of reactant gas by blending two gases with different humidity.

In some embodiments, a NO generation system can be connected to a source of dry gas containing nitrogen and oxygen. While dry gas is beneficial in providing control to NO production, it can be harmful to a scrubbing component that relies on moisture, such as a soda lime scrubber. Passing dry gas through a soda lime scrubber removes moisture, hastening the exhaustion of the scrubber. Further complexity can arise when a NO generator includes gas sensors to measure NO and/or $NO_2$ within the reactant and/or product gas. In the case of electrochemical sensors, for example, sensors often have an optimal humidity range and can prematurely dry out over time if dry gas passes over it. For example, one electrochemical sensor has a humidity range of 25-90% RH while another electrochemical sensor has a humidity range of 15-95%. Thus, in applications that utilize dry gas as a source of reactant gas, it can be beneficial to add humidity to the gas at various points in the system to safeguard against premature scrubber and/or gas sensor exhaustion. FIG. 24 depicts an embodiment where dry gas is blended using a blender 462 with humid gas from a humidifier 460 to a known humidity level before it enters a NO generator 464. In some embodiments, sufficient humidity is added so that the scrubber and gas sensors are protected while not providing enough water content to induce condensation within the system. In some embodiments, the target humidity is 20%. In some embodiments, the target humidity can range from 15% to 70% RH for example. In some embodiments, a humidity target of 15% to 95% is utilized.

Figure 25:
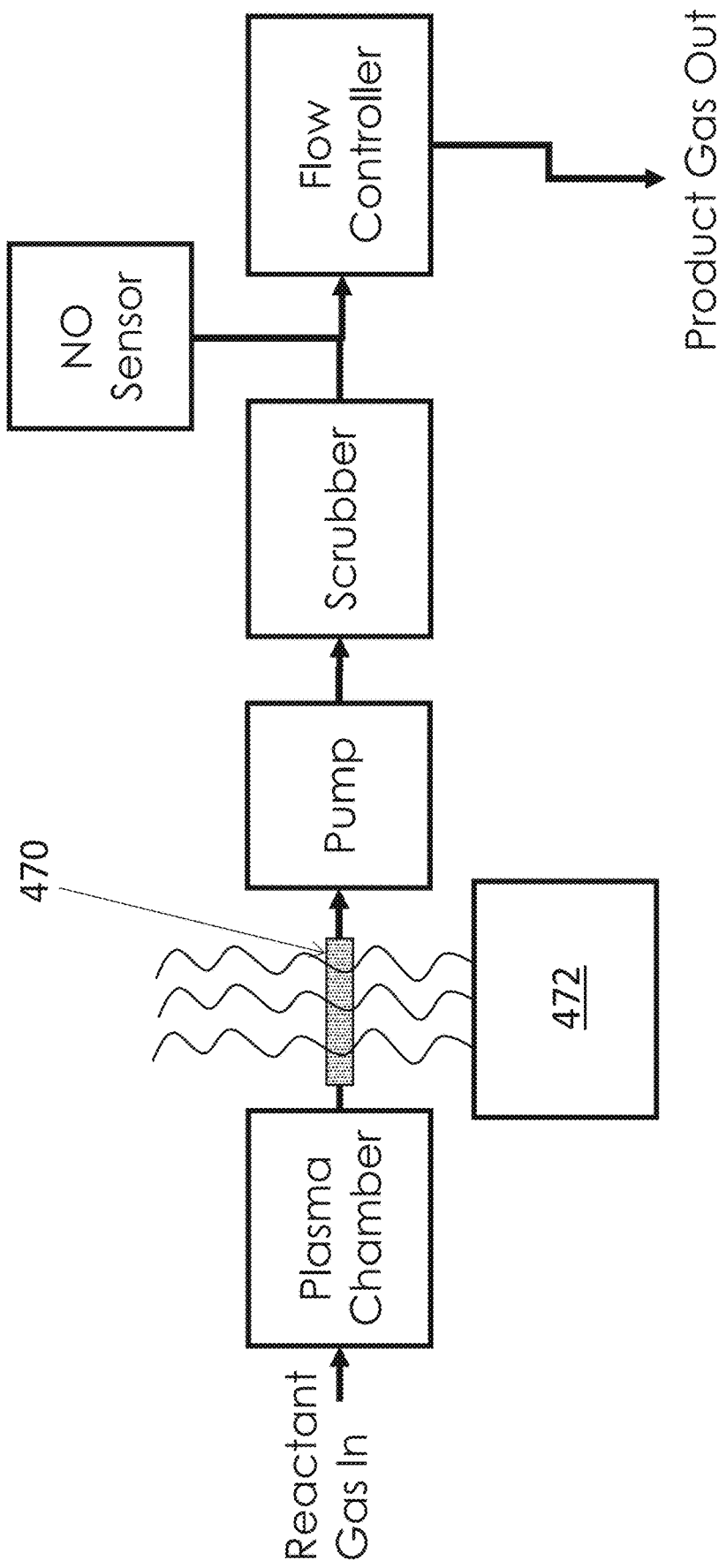
FIG. 25 depicts an embodiment that can add humidity to reactant gas of a NO generation system.

In an embodiment depicted in FIG. 25, NO is generated in dry reactant gas within one or more plasma chambers. After NO generation, product gas flows through humidity exchange tubing 470 that is exposed to humid gases from a humidifier 472. Sufficient humidity is added to the product gas to protect the NO sensor and scrubber material downstream without being enough humidity to cause condensation in the high-pressure region between the pump and scrubber.

Figure 26:
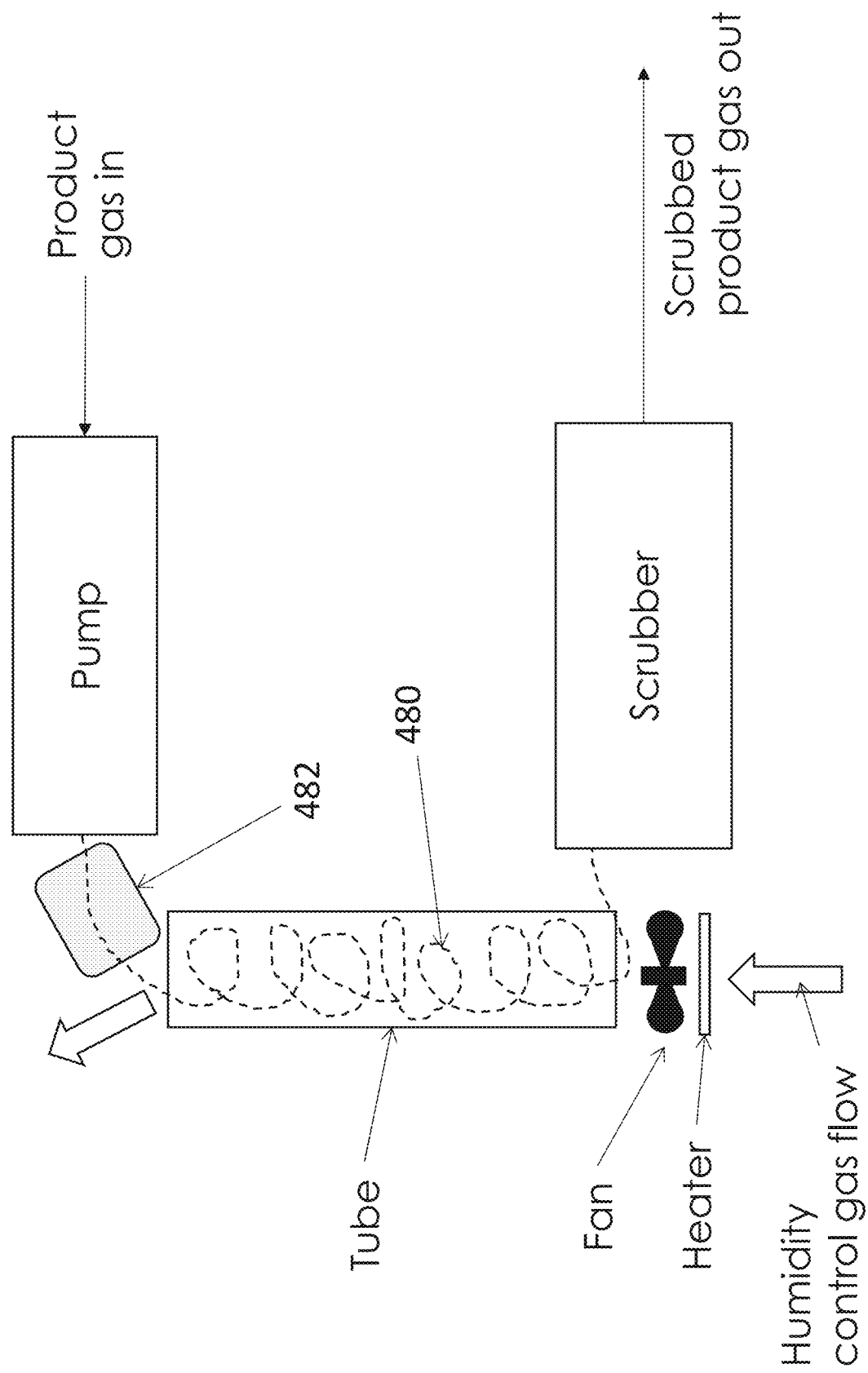
FIG. 26 depicts an embodiment that utilizes a fan, humidity exchange tubing and optional heater to modulate humidity with a product gas.

In some embodiments, gas passes through humidity exchange tubing placed within a tube. A fan blows air through the tube. An optional heater can be energized to increase water transfer from the gas within the device out to the fan gas flow. FIG. 26 depicts an embodiment where product gas is pumped through humidity exchange tubing 480. Water transfers from the product gas to convective gases due to temperature, pressure and water capacity differences. Insulation 482 after the pump keeps the gas warm until water exchange can take place. It will be noted that this approach can be utilized in other locations within the system. In some embodiments, reactant humidity is altered prior to entry into a recirculation loop and/or plasma chamber.

In some embodiments, a $NO_2$ scrubber is used to provide humidity to a NO generation device. In some embodiments, a low humidity measurement within the NO generation system is indicative of a dry scrubber. In some embodiments, the NO generation system prompts a user to replace a $NO_2$ scrubber when the humidity level within the system drops below a specific level, indicating that the scrubber is dry.

In some embodiments, the operating pressure of the system is reduced in response to elevated reactant gas humidity to decrease the saturation of the intake air with water vapor. In some embodiments, the intake air is processed by the system before it enters the pump and/or reaction chamber. In some embodiments, the intake air to the pump is heated to higher temperatures to avoid condensation. In some embodiments, the intake air is dried using desiccant.

Figure 27A:
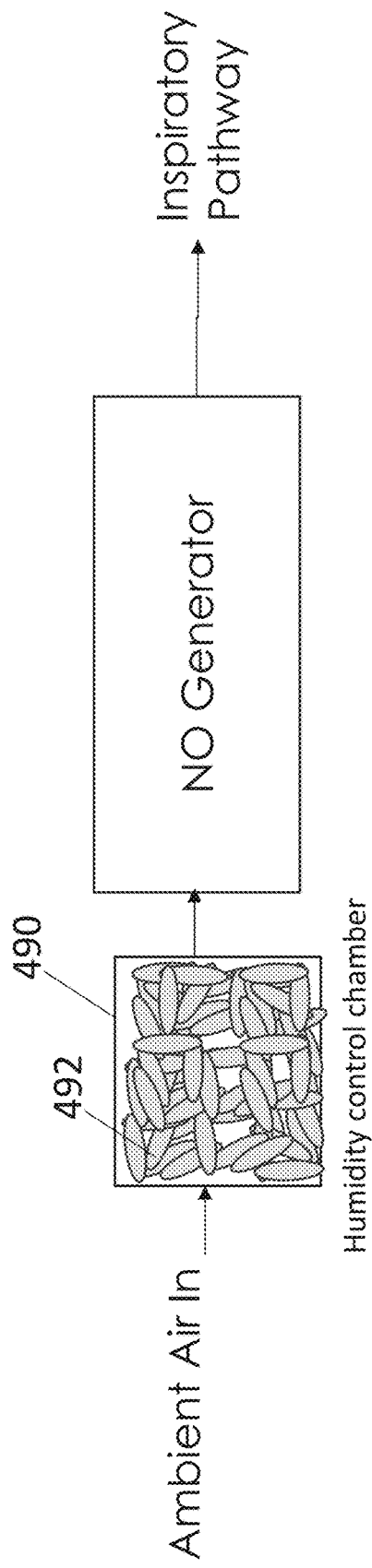
FIG. 27A depicts an embodiment that passes gas through a humidity control chamber with a humidity control media where the gas is in direct contact with the humidity control media.
Figure 27B:
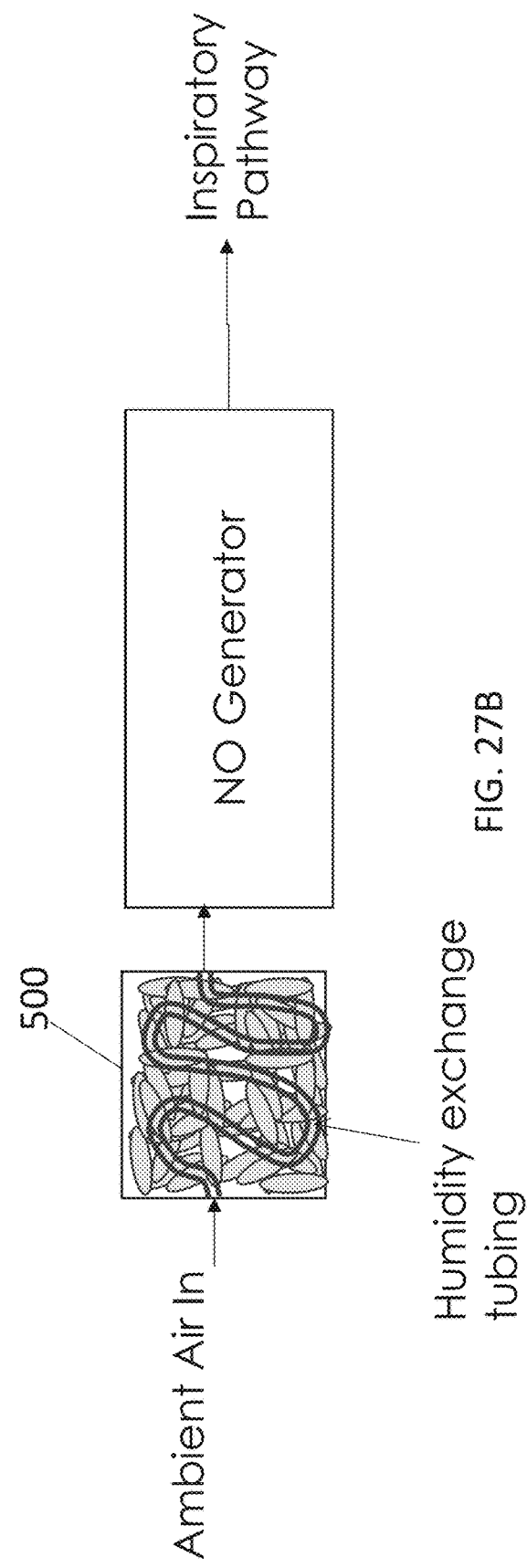
FIG. 27B depicts an embodiment with a humidity chamber with a humidity control media where the gas is in indirect contact with the media by use of a humidity exchange membrane.

Various materials can be used to manage humidity, including silica gels, clay desiccant and/or molecular sieves. For example, desiccants like silica gel, alumina and molecular sieves have high affinity towards water and can retain water either through absorption and/or adsorption on the surface or the pores. The water retention capacity of the desiccant can be controlled by changing the surface area and/or pore size. In some embodiments, desiccant material (e.g. silica) is utilized to drive the humidity of a gas to the desired range. For example, desiccant silica gel beads designed to maintain a specific humidity can be utilized to humidify overly dry reactant gas and dry overly humid reactant gas prior to entry into the NO generator. In some embodiments, humidity regulating gel designed to maintain a humidity of 50% RH is utilized, however other target humidity levels can work as well. FIG. 27A depicts a design whereby reactant gas passes through a chamber 490 filled with humidity control material in the form of beads 492 prior to entering the rest of a NO generation device. Beads are depicted but many other form factors can work, including sheets, ridged sheets, granules, hexagonal extrusions, and others. In some embodiments, the humidity control media is a desiccant. In some embodiments, the humidity control media is selected to drive the humidity within the chamber to a specific humidity (e.g. 50% RH). In some embodiments, the chamber contains a desiccant material and is a disposable component that can be separated from the NO device. In some embodiments, the desiccant chamber can be "recharged" by adding/removing water to/from the desiccant material. FIG. 27B depicts an alternative design where reactant gas is in indirect contact with the humidity management material. Gas passes through humidity exchange tubing and does not directly contact the desiccant material. In some embodiments, gas passes through one side of a chamber 500 with humidity exchange membrane separating it from a humidity management material on the other side. This can be advantageous in decreasing the potential of contaminating the reactant gas with VOCs and/or particulate. These examples demonstrate how desiccant can be used to drive gas humidity to a desired range. This principle can be utilized in other locations within a NO generation system, such as post-pump, within a recirculation loop, or near a humidity-sensitive sensor to prevent condensation and/or ensure acceptable humidity levels for system components. In some embodiments, desiccant material and the associated gas pathway are combined with another component of a NO generation system, such as a water trap or scrubber cartridge. In some embodiments, the gas path through humidity exchange material is reusable while the humidity management material (desiccant for example) is part of a disposable and/or removable component. In some embodiments, humidity exchange material can be reset and reused. For example, a chamber containing desiccant can be removed from a NO generation device, placed in a warm/dry location (e.g. oven) and dried prior to re-use. In some embodiments, a desiccant is made of a clay material, such as magnesium aluminum silicate, also known as Montmorillonite clay.

In some embodiments of a NO generation system, modules of humidity management material are designed for specific climates. For example, a module used in Antarctica where air is dry would have humidity management material that adds humidity to reactant gas and a module used in the tropics would have humidity management material that dries incoming gas. In some embodiments, humidity management modules are identified via wired or wireless means by a NO generation device prior to use. Humidity management modules may also contain as part of their labeling or within a memory device pertinent information including but not limited to date of manufacture, lot #, plant #, target humidity, capacity, expiration date, hours of use, date first used, remaining capacity, number of times it has been recharged, etc. A NO generator may read and/or write to a humidity management module.

Figure 28:
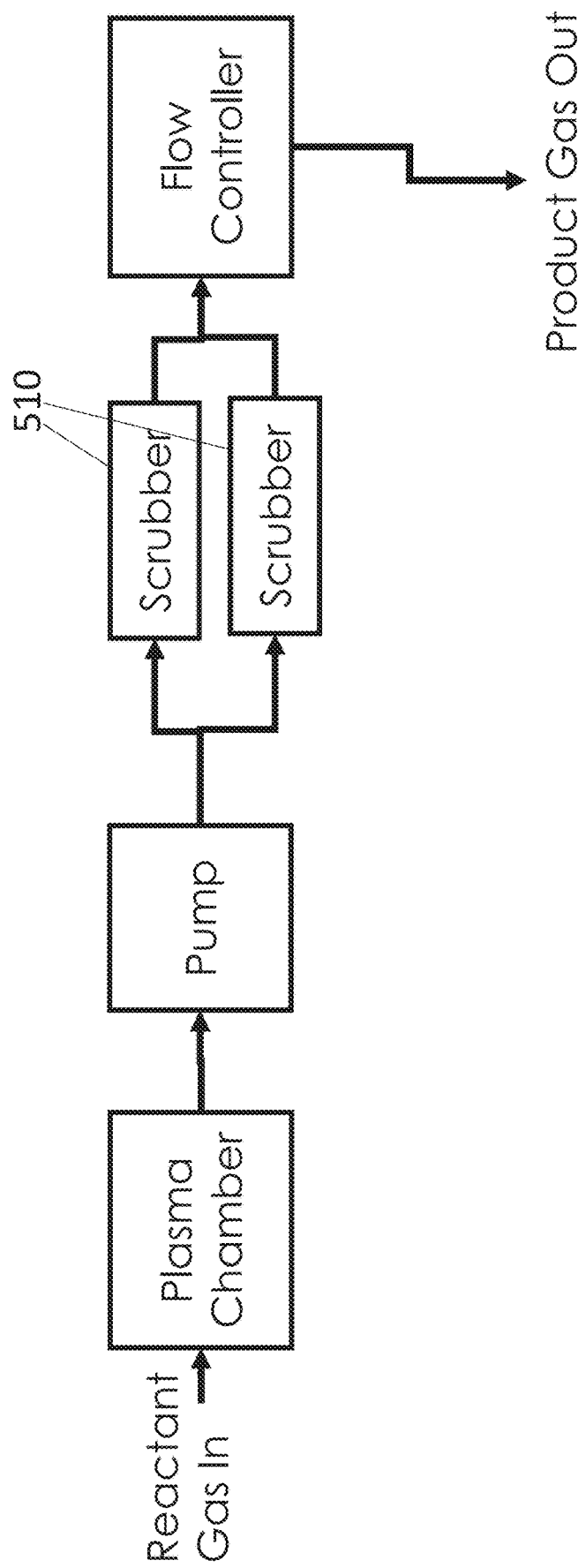
FIG. 28 depicts an embodiment where scrubbers are utilized in parallel to reduce pressure within a NO generation system.

As pressure in a gas increases, the water-carrying capacity decreases. Thus, efforts to decrease maximum pressure within a NO generation system can reduce the propensity for condensation within the system. $NO_2$ scrubbers can introduce considerable flow restriction in the gas flow path, thereby increasing pressure in the gas upstream of the scrubber. It follows that efforts to reduce the flow restriction of the scrubber can reduce the propensity for condensation and eliminate the need for humidity controls in some cases. In an embodiment depicted in FIG. 28, parallel scrubbers 510 are used to reduce flow restriction. In some embodiments, scrubbers are constructed from layered or coiled sheet material with minimally obstructive flow channels.

Figure 29:
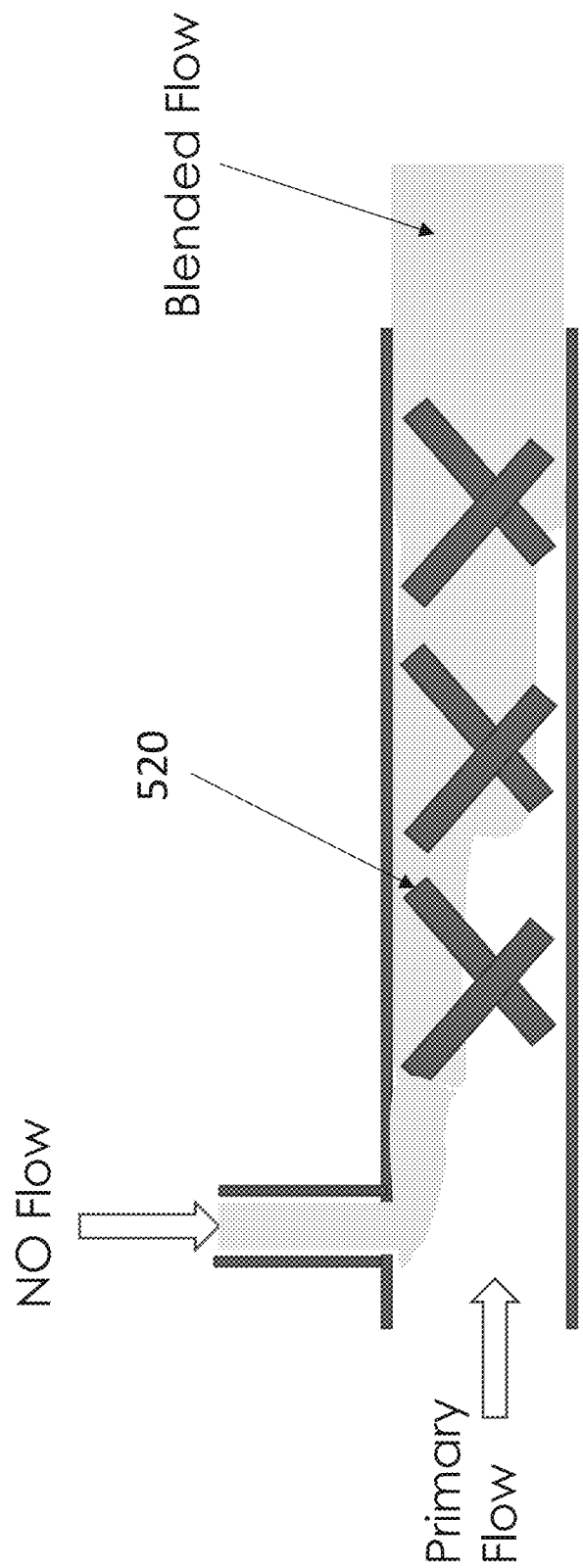
FIG. 29 depicts an embodiment of a NO generation system that utilizes static mixing elements to mix NO-containing gas into another gas flow.
Figure 30:
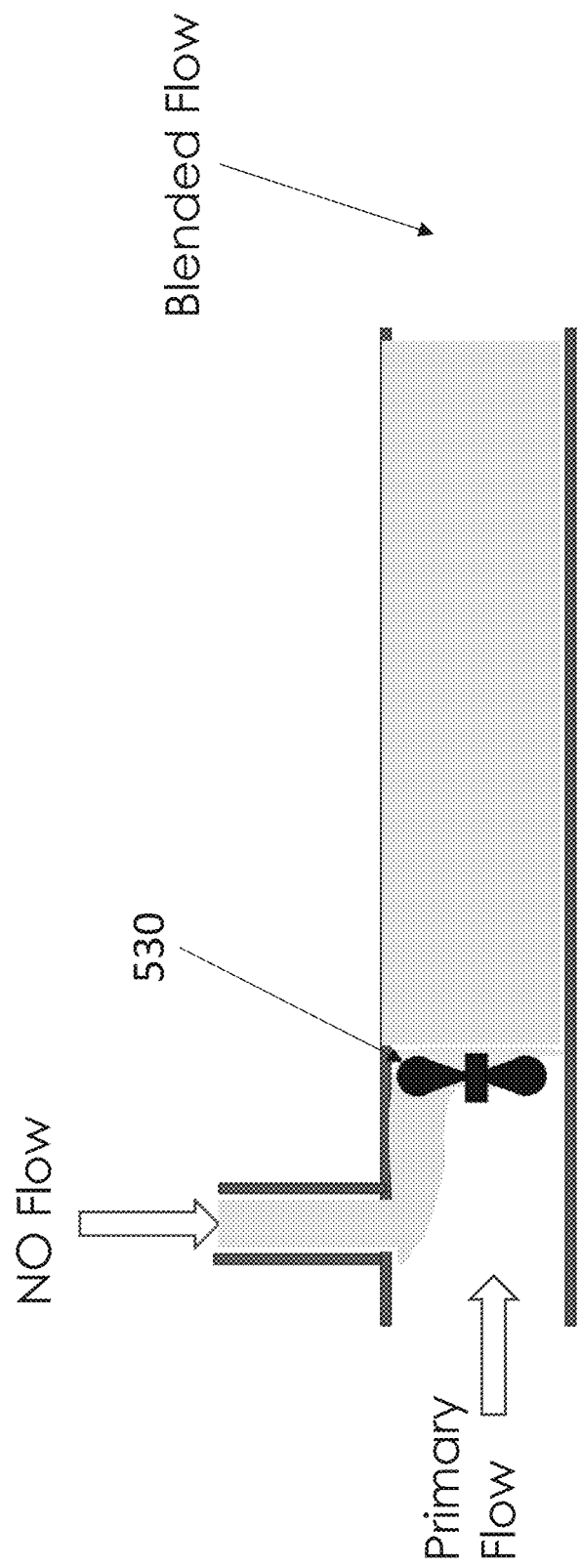
FIG. 30 depicts an embodiment of a NO generation system that utilizes a dynamic mixing element to mix NO-containing gas into another gas flow.

When NO is introduced to a gas flow, it can take considerable time and/or distance to passively blend into the flowing gas. This can present an issue when the combined gas flow bifurcates prior to complete mixing. For example, a NO sensor placed on the side of a gas flow tube may be located in a region of high NO or low NO thereby indicating an inaccurate measurement of NO concentration. Thus, it can be beneficial to mix NO with primary flow gas over a shorter period of time and/or distance. In some embodiments, static mixers are used to shear the gas flow and create turbulence to create more interaction between the two flows. FIG. 29 depicts an example of a static mixing element 520 to homogenize gas after the injection of NO. High concentration NO enters a tube from above and remains near the upper wall. Mixing elements within the tube shear the NO flow and create turbulence to homogenize the blended flow. In another embodiment shown in FIG. 30, a dynamic mixing element 530 is utilized to blend gases. Dynamic mixers can include but are not limited to fans, blowers and pumps. In some embodiments, injected NO is introduced to the primary gas flow through multiple orifices, like a shower head, to distribute NO more evenly within a gas flow. The rate of NO oxidation increases with the concentration of NO. Thus, mixing of NO has an additional benefit in reducing the concentration of NO more rapidly than would otherwise occur, thereby reducing NO oxidation to $NO_2$.

Figure 31:
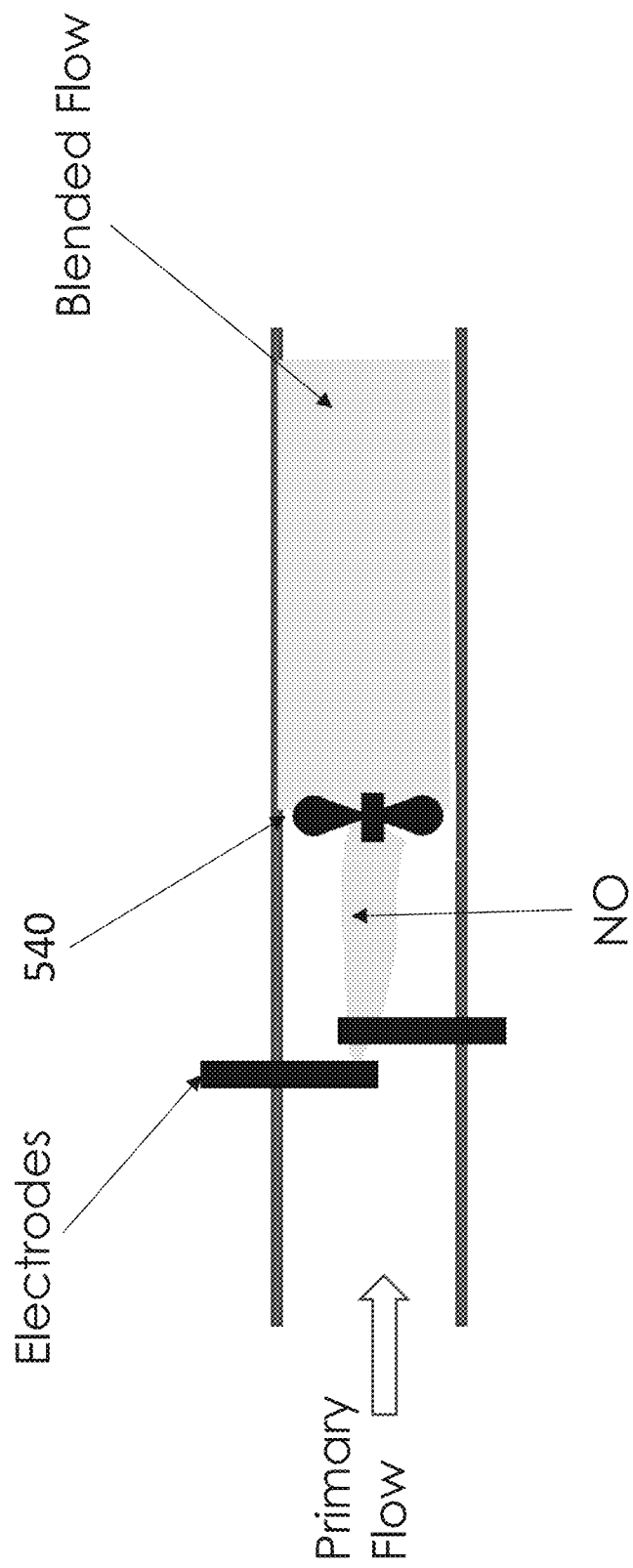
FIG. 31 depicts an embodiment of a NO generation that mixes product gas.

FIG. 31 depicts an embodiment that actively mixes NO gas after NO generation using a dynamic mixing element 540 to homogenize the gas and decrease peak concentration within the gas and slow the rate of NO oxidation. In some embodiments, features are added to a product gas flow path to induce turbulence and promote mixing or product gas. In some embodiments, a $NO_2$ scrubber acts as a static mixer to homogenize product gas.

FIG. 32A and FIG. 32B depict embodiments of low-pressure NO generation. FIG. 32A produces NO at roughly atmospheric pressure. Product gas exits a plasma chamber 550 and passes through a scrubber 552 before passing through a pump 554 and flow controller 556. In this embodiment, the pressure between plasma chamber and scrubber are below atmospheric levels with temperature typically exceeding atmospheric levels due to thermal energy from plasma generation thereby preventing water condensation. The pump elevates pressure to a sufficient level to provide flow to the flow controller and direct product gas to a patient. In this embodiment, the pump head (delta pressure) is used to pull a vacuum on one side and elevate pressure to a lower total pressure than an architecture with a pump at or near the beginning of the pneumatic pathway. FIG. 32B depicts an embodiment where a pump 560 is located after a flow controller 566 so that pressure within the entire system is below the level of the source reactant gas thereby preventing condensation of water within the reactant gas. The system depicted in FIG. 32B delivers NO to an inspiratory pathway where the product gas is diluted by the flow of a medical gas.

Recirculation Architecture

FIG. 33 depicts a recirculation architecture that utilizes the heat generated from the pump and plasma chamber to dry incoming reactant gas. Reactant gas enters a humidity transfer tube 570 and passes through a heated chamber 572 that houses the plasma chamber 574, a pump 576, and/or other heat generation components. A fan 578 blows gas through the chamber to provide a supply of fresh gas to absorb humidity from the reactant gas. In some embodiments (not shown), the fan draws air out of the heated zone thereby reducing the pressure within the chamber and increases water removal from the reactant gas pathway.

Figure 34:
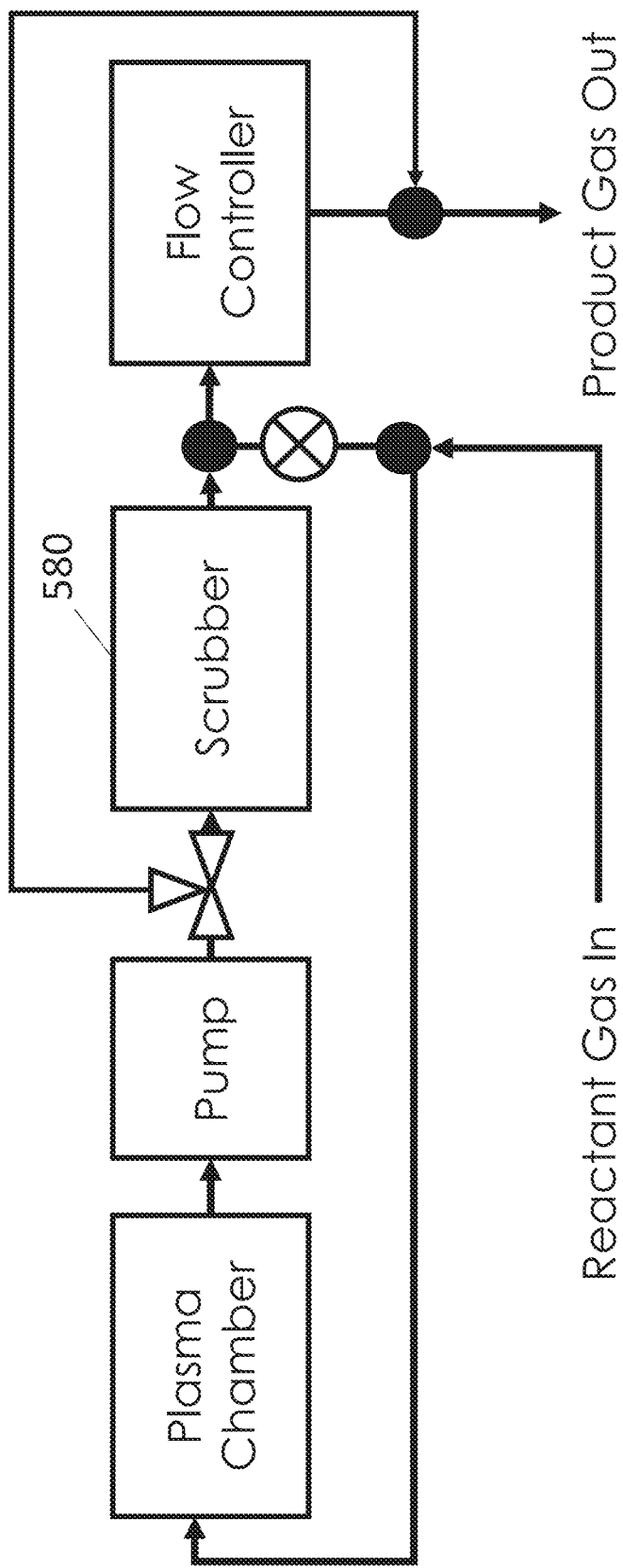
FIG. 34 depicts a NO generation system with recirculation loop architecture that can purge a NO path at a low pressure by bypassing the scrubber and flow controller.

FIG. 34 depicts a NO generator that bypasses a scrubber 580 for purging the system. NO product gas passes through the scrubber for removal of $NO_2$. When NO generation ends, the system passes reactant gas (e.g. air) through the pneumatic pathway to purge the system of NO. A scrubber presents a flow restriction to a gas flow path. As gas passes through the scrubber, there is a corresponding pressure drop. The drop in pressure can drop the temperature of the gas and cause condensation to occur when the gas has a high water content. Bypassing the scrubber reduces the pressure of gas during purging, thereby reducing the propensity for water to condense within the system to reduce system humidity.

Figure 35A:
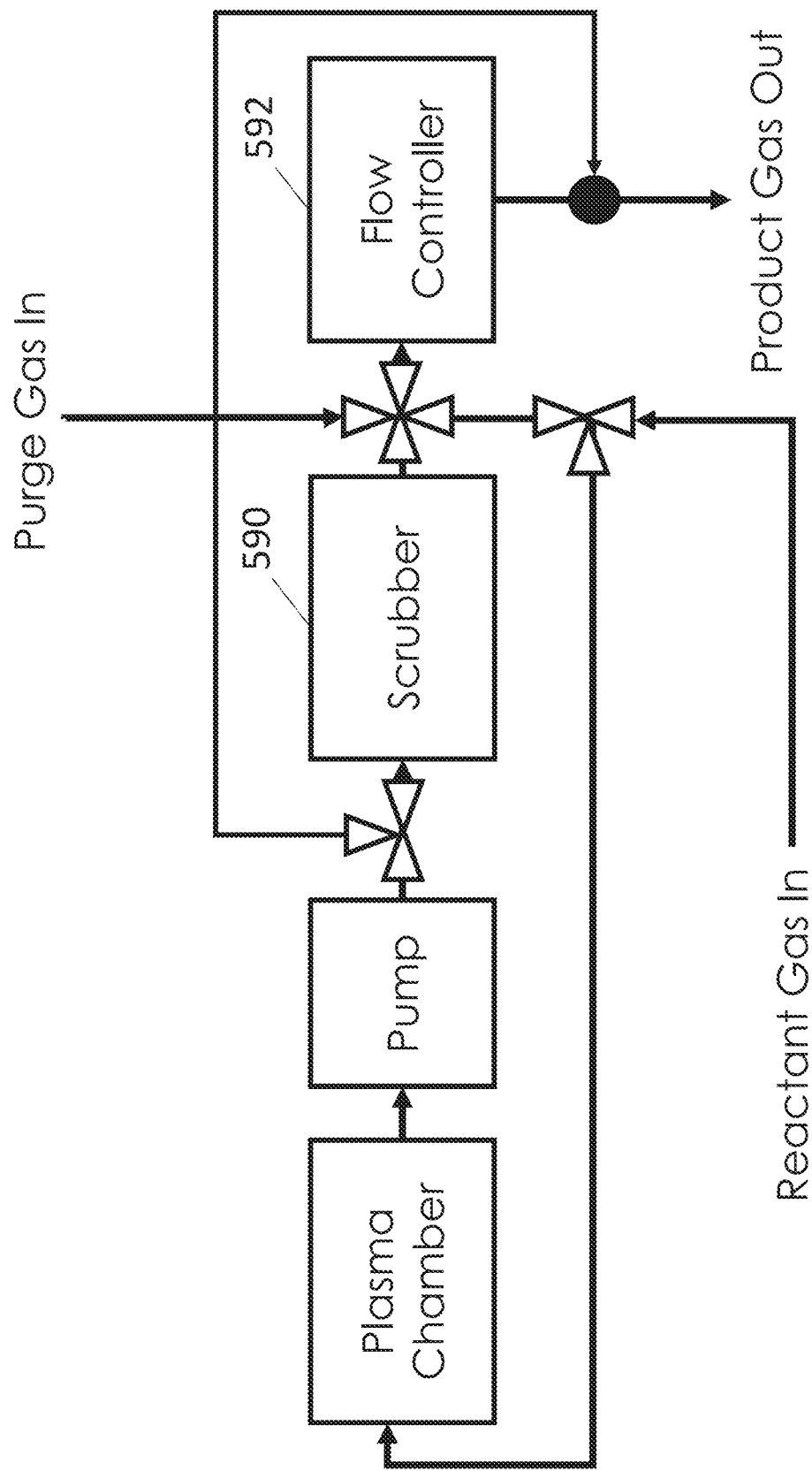
FIG. 35A, FIG. 35B, FIG. 35C, and FIG. 35D depict an embodiment of a NO generation system with recirculation architecture and an ability to purge the high-pressure region of the system between NO generation events
Figure 35B:
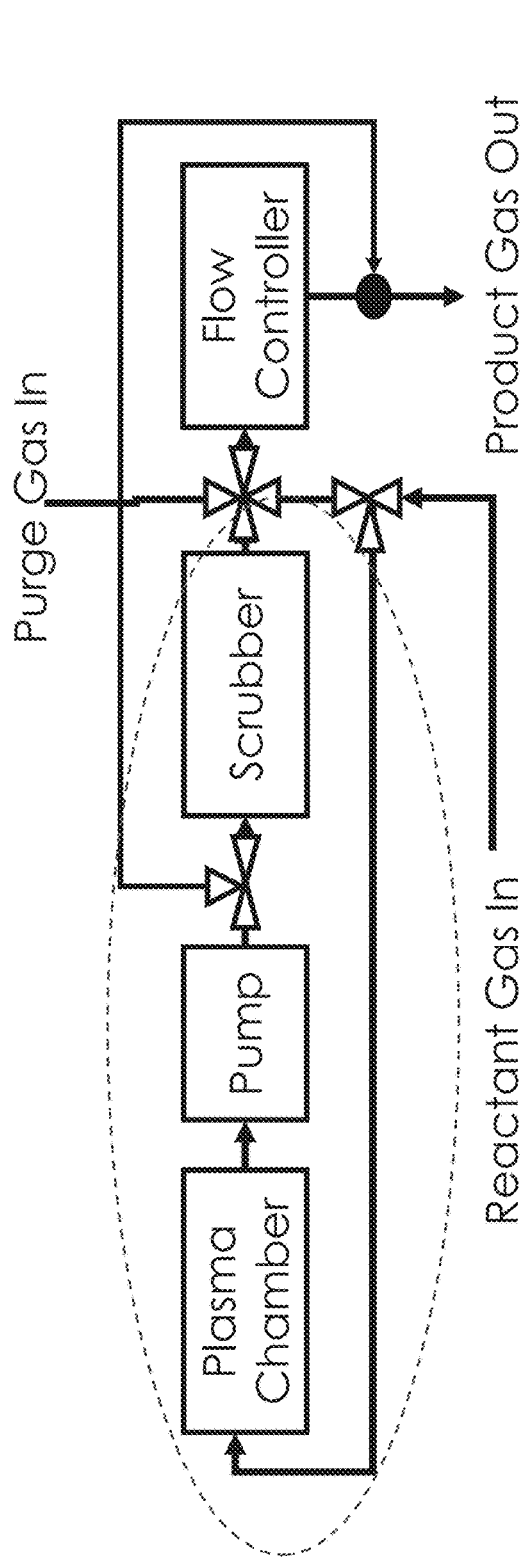
Figure 35C:
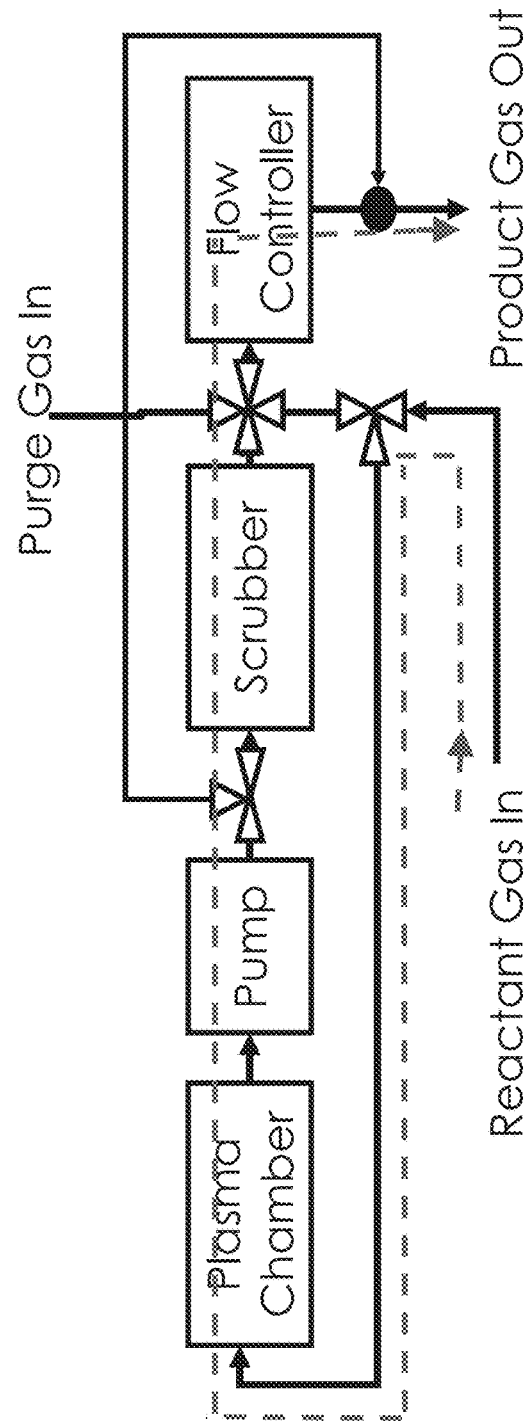
Figure 35D:
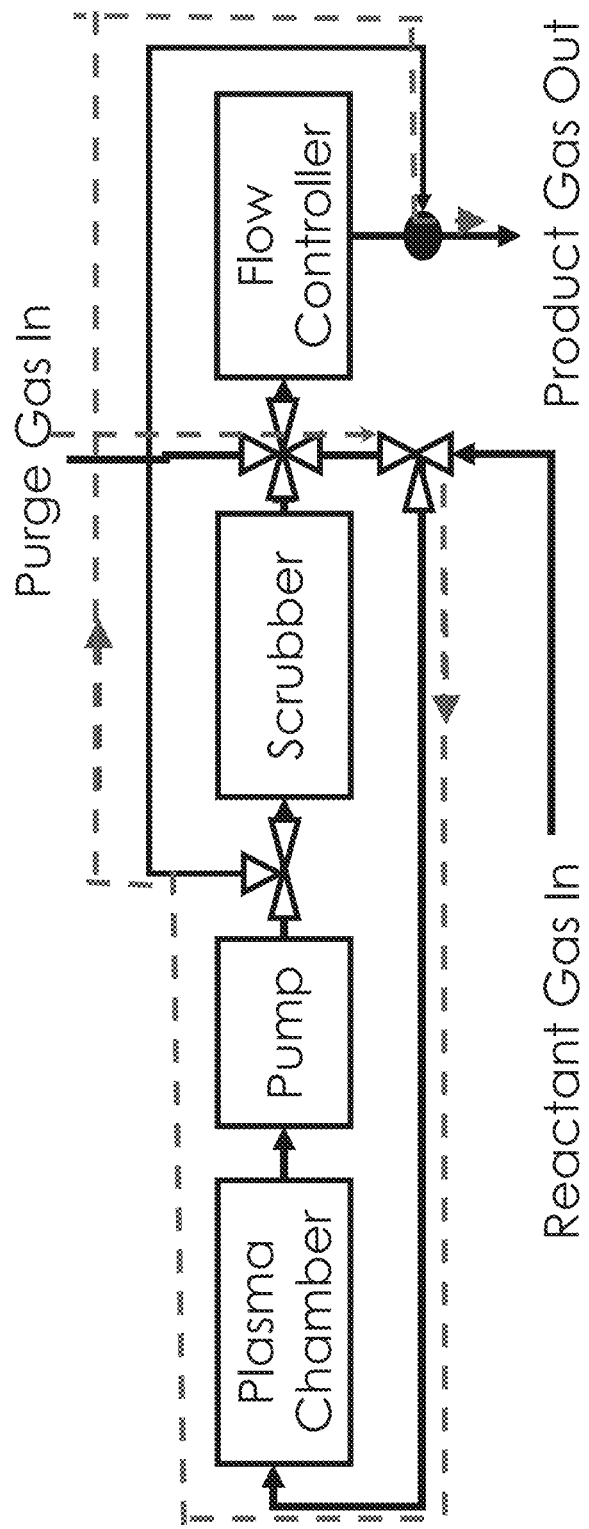

FIG. 35A depicts a NO generation system with an ability to source gas either directly from an external gas source or by passing externally-sourced gas through a zone between a scrubber 590 and a flow controller 592. Similar to the arrangement shown in FIG. 34, there is less flow through the scrubber, and the purge gas is at low pressure to keep the humidity in the system low. An initial NO bolus can be generated within a recirculation loop, as shown in FIG. 35B with a dashed arrow. When the device is ready to begin NO delivery, the system configures valves in the system to convert to an open pneumatic pathway where reactant gas is sourced from an external source, passes through the plasma chamber, pump and scrubber before being delivered through a flow controller, as shown in FIG. 35C. The reactant gas inlet is very close to the space between scrubber and flow controller to minimize the amount of NO that could reside within that space during NO generation and delivery. The system can utilize the plasma chamber to produce additional NO with this open pneumatic pathway. When sufficient NO has been generated, the system configures valves in the system to pass incoming gas through the space between scrubber and flow controller as shown in FIG. 35D. This incoming purge gas collects any water that condensed downstream of the scrubber as it passes through the system. Pressure in the purge gas is kept low because it does not pass through the scrubber flow restriction.

Figure 36:
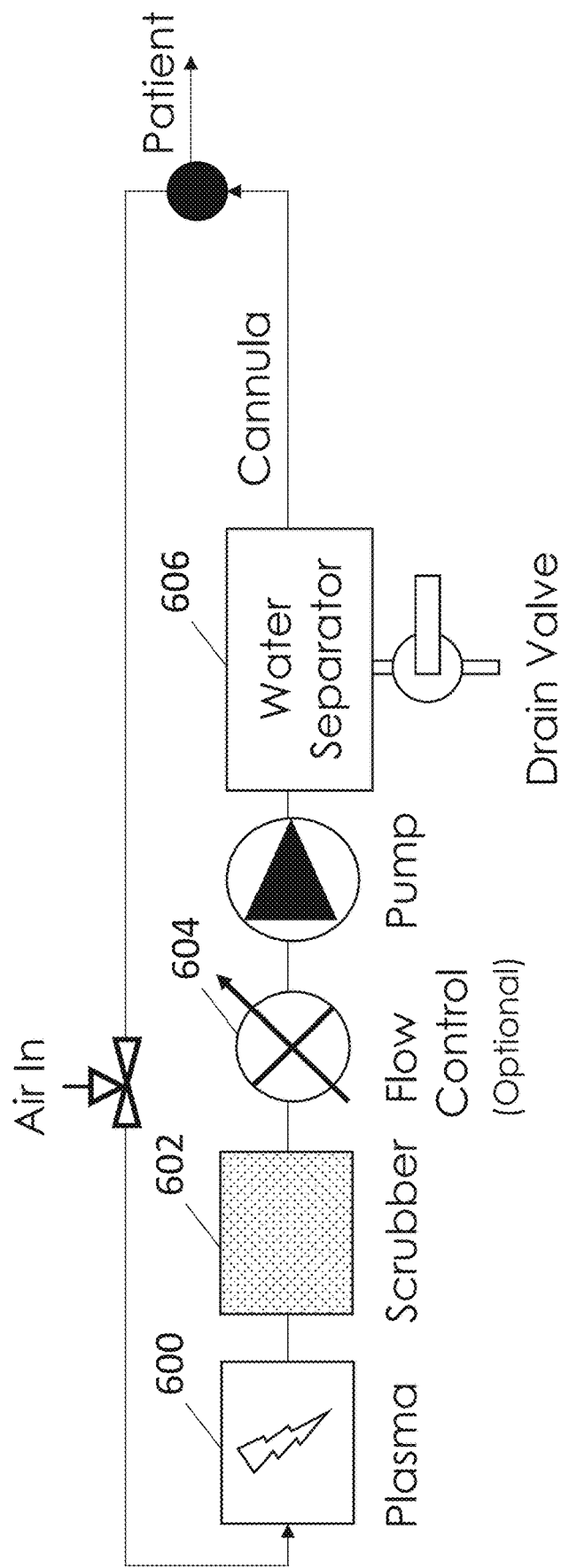
FIG. 36 is an exemplary embodiment of a humidity management recirculation loop.

FIG. 36 depicts a recirculation loop that includes an NO delivery cannula. This approach can locate the NO closer to the patient at the time of inhalation. As presented, a plasma chamber 600, scrubber 602 and optional flow controller 604 are at pressures below atmospheric which prevents condensation within the system. There is a potential for condensation after the pump as the pressure in the product gas increases. Thus, any water separator 606, including but not limited to a water trap, water separator, humidity management material, or other stage described herein can be located to manage water prior to the cannula. In some embodiments, the pump can be run to circulate air through an external loop. Optionally, breath can be detected. NO is generated by the plasma chamber, and NO travels to the cannula, being pushed and pulled by the pump. When NO reaches the junction, the 3-way valve can be toggled to source air from outside. The plasma can be turned off at end of NO pulse, the pump can be turned off after cannula has been purged, and 3-way valve can be toggled back to a closed loop setting.

Figure 37:
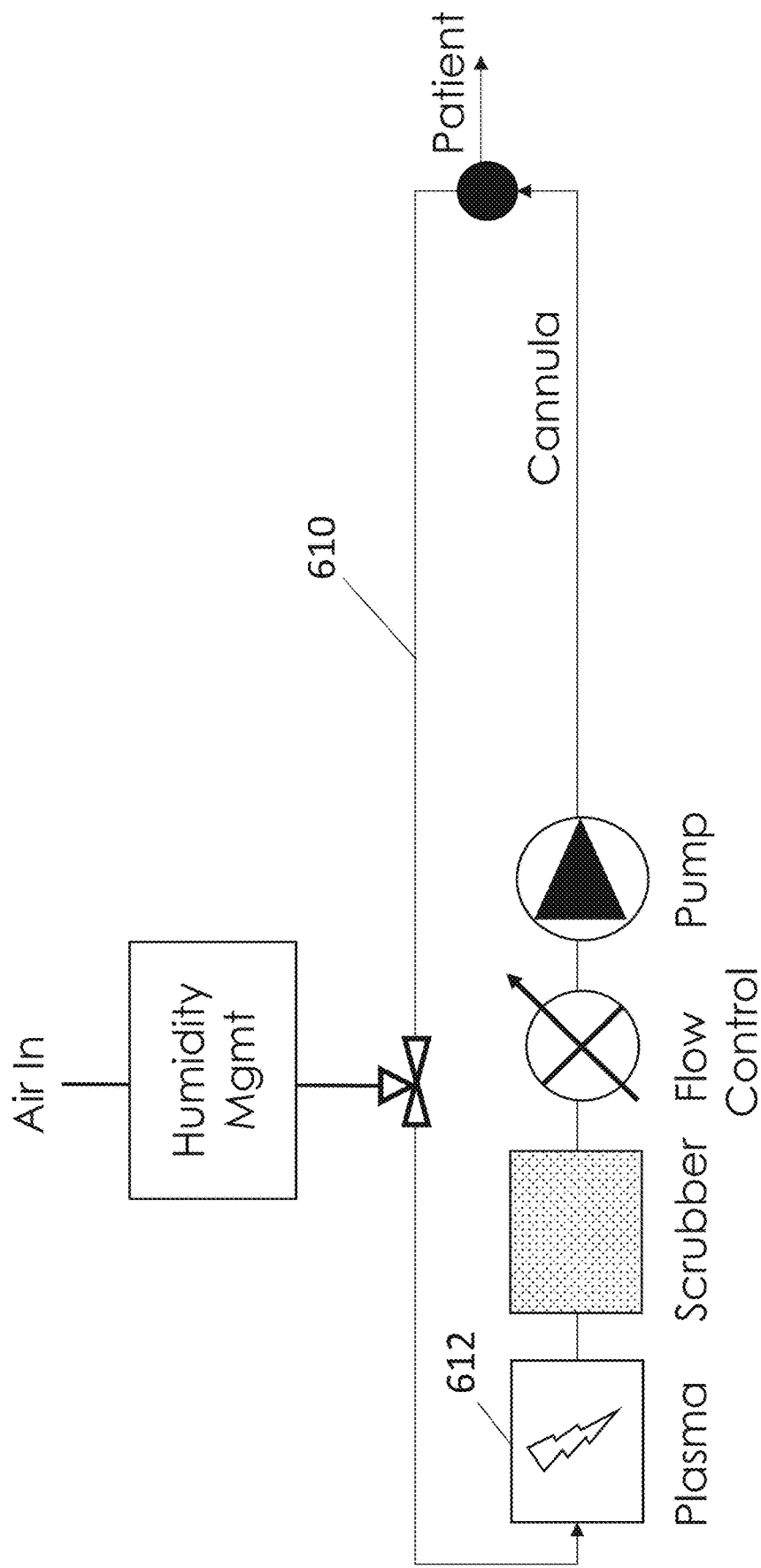
FIG. 37 is an exemplary embodiment of a humidity management recirculation loop.

FIG. 37 depicts a NO generation system where humidity management is performed on the incoming reactant prior to entering a recirculation loop 610, entering the plasma chamber 612, and/or getting pressurized. This approach removes water from the reactant gas to a level that prevents condensation elsewhere in the system. To be clear, the amount water removal does not need to be 100%, only enough to prevent condensation within the system. Any of the moisture removal concepts presented herein can be applied including but not limited to: desiccant materials, humidity exchange tubing, water traps, water separators, etc.

Humidity Compensation

Water content within the reactant gas can affect NO production and the ratio of NO to $NO_2$. In a system with humidity controls, a measurement of ambient humidity or water content may not be sufficient as an input into the NO generation controller. In some embodiments, the NO generation system can measure humidity after the de-humidification process to have an accurate measurement of water content in the reactant gas that enters the plasma chamber. In some embodiments, the sensor can be in the high-pressure side. Since the propensity for condensation of water vapor in reactant gas is greater on the high-pressure side, placing the humidity sensor in the high pressure gas path helps in detection of condensation faster. However, the risk of sensor saturation due to condensed water also increases. In some high pressure plasma embodiments, the sensor can be at the low-pressure side, after the flow controller, but before the plasma chamber. By measuring the pre-plasma chamber humidity, the changes in NO generation due to reactant gas humidity can be calculated and compensated for. Also, special controls for operation in highly corrosive NO gas pathway is not necessary. In some embodiments, the humidity is measured post-plasma chamber and used to calculate the pre-plasma chamber humidity. This would help the sensor to avoid damage due to the higher temperatures of the plasma chamber and the potential saturation due to condensation on the high pressure side.

There are many types of humidity sensors including capacitive, resistive, and thermally conductive. Capacitive sensors are the most common types of humidity sensors. They consist of two electrodes whose capacitance is determined by the amount of water vapor between them (our water trap sensor works in a similar way). A thin dielectric layer between them absorbs water vapor from the surrounding air. This changes the dielectric constant and thus, the capacitance. There is a direct relationship between the relative humidity in the air, the amount of moisture contained in the dielectric material, and the capacitance of the sensor. Capacitive humidity sensors provide stable readings over time and are capable of detecting a wide range in relative humidity. They also provide near linearity with signal amplitude over the range of humidity. They are limited by the distance between the sensor and the signaling circuit.

Resistive sensors also consist of two electrodes. The device consists of a hygroscopic conductive layer in the form of a polymer humidity sensing film that is mounted on a substrate. The conductive film contains a set of comb-like electrodes, usually deposited from a noble metal like gold, silver, or platinum that are laid out in an interdigitated pattern to increase the amount of contact area between the electrodes and the conductive material. The resistivity of the conductive material will vary inversely with the amount of moisture that is absorbed. As more water vapor is absorbed, the non-metallic conductive material increases in conductivity hence decreases in resistivity. Resistive humidity sensors are low-cost devices with a small footprint and are readily interchangeable. Unlike capacitive humidity sensors, resistive humidity sensors can function in remote monitoring applications where the distance between the sensor element and the signaling circuit is large.

Thermal conductivity sensors are used to measure absolute humidity (as opposed to relative humidity). They calculate the difference in thermal conductivity between dry air and humid air.

In some embodiments, a NO generation system actively manages humidity levels at one or more locations within the system. Data from one or more temperature, pressure and humidity sensors provide inputs to a gas humidity management control algorithm. A NO generation system can measure humidity directly by use of one or more humidity sensors at one or more of the following locations: An ambient air location, a reactant gas location, a product gas location, a pre-scrubber location, a post-scrubber location, a pre-injector location, a recirculation loop location, a pre-gas sensor location. In some embodiments, ambient humidity is measured, and a control algorithm determines the temperature and flow rate of a humidity removal component to remove enough water to prevent condensation at known pressures within a system. In some embodiments, humidity of reactant gas is measured as it enters a NO generation system. A NO generation system looks up the amount of water that needs to be removed to ensure that a electrochemical gas sensor is not exposed to excessively humid gas and modulates the reactant gas drying feature accordingly. In some embodiments, humidity of pressurized gas within a NO generation system is measured. The controller modulates water addition/removal from reactant gas to maintain humidity of the pressurized gas below condensing levels in a closed-loop fashion. For example, as the humidity of the pressurized gas exceeds 80% RH, the reactant gas humidity removal system is activated to ensure that relative humidity will not reach 100%. In some embodiments, a NO generation system receives a humidity measurement from an external device or web interface.

Figure 38:
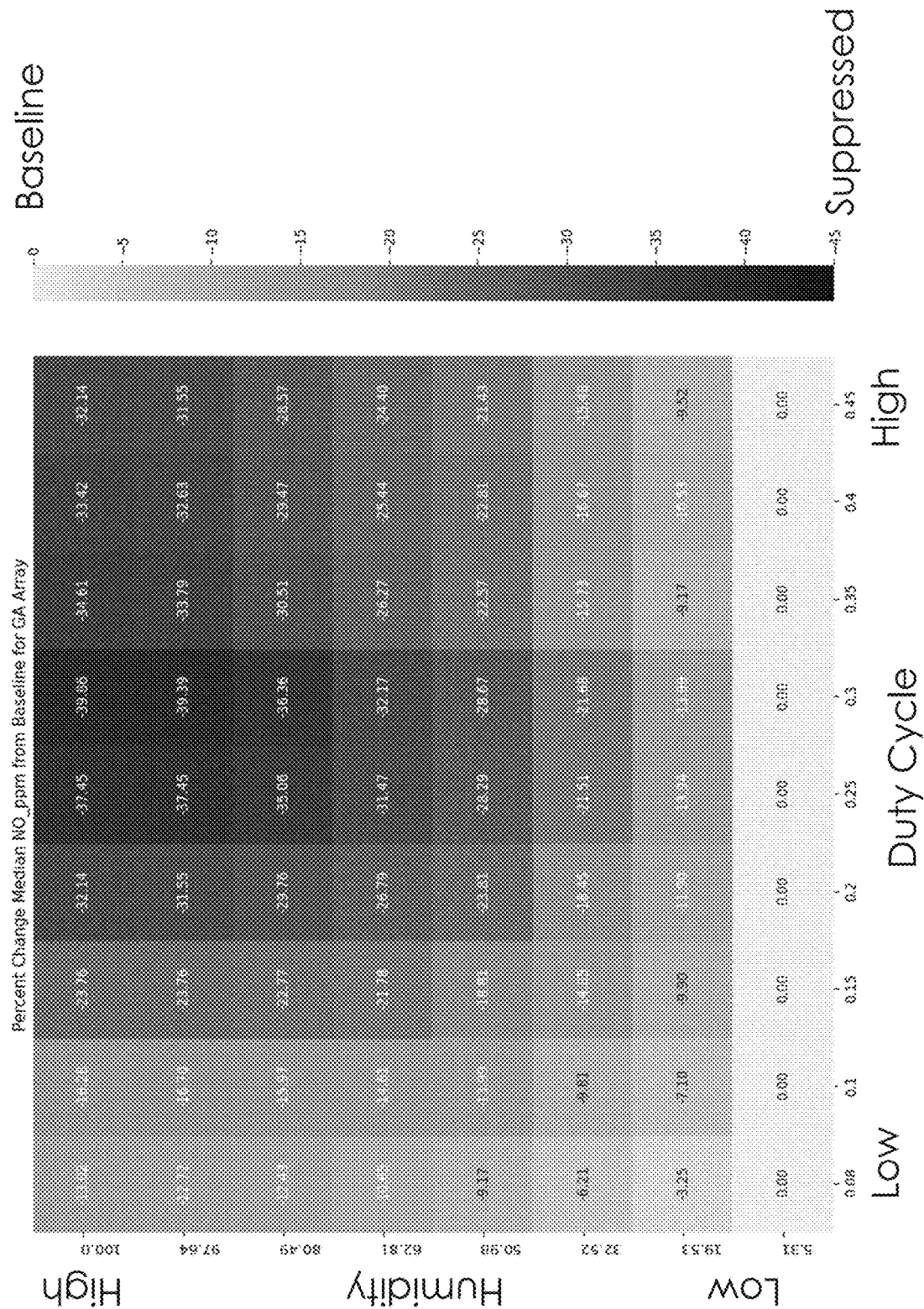
FIG. 38 depicts representative data of NO production suppression due to elevated humidity.

FIG. 38 depicts an example of a humidity compensation look-up table with duty cycle along the X axis and humidity along the Y axis. Darker shades of coloring indicate higher levels of NO production loss due to elevated humidity. Depending on the application, the look-up table may require additional dimensions, such one or more pressures or temperatures within the system. Conditions in between the discrete measurements presented in the table can be interpolated by the NO generation controller. This same information can also be captured in a mathematical equation to determine lost NO production due to reactant gas humidity at various duty cycles. Similar charts could be made for other production control parameters, such as pulse energy, pulse frequency, etc., depending on the control scheme of the NO generation device. The controller within the NO generation device can make up for NO production loss due to humidity by altering the properties within the plasma chamber. These properties include but are not limited to reactant gas flow rate, plasma discharge energy, plasma discharge duty cycle, reactant gas pressure, and plasma discharge frequency.

The water saturation capacity of air is dependent on pressure and temperature. By measuring the pressure, temperature, and relative humidity of gas, using sensors, the water content of the gas can be calculated using standard psychrometric look-up tables. In some embodiments, a NO generation system measures ambient air pressure, temperature and relative humidity and calculates the water content of the reactant gas. It then determines whether or not there is a risk of condensation after the gas is compressed within the system. If there is a risk of condensation, a humidity management system is activated, otherwise the humidity management system is not activated. In some embodiments, a humidity management system is active during all operation, eliminating the needs for a NO generation controller to actively control a humidity management method. Modulation of a humidity management system is also possible in order to minimize energy expenditure and not over-dry the gas. In some embodiments, the humidity management system is modulated in a pulse-width modulation approach. In some embodiments, the humidity management system is varied in an analog way.

Figure 39:
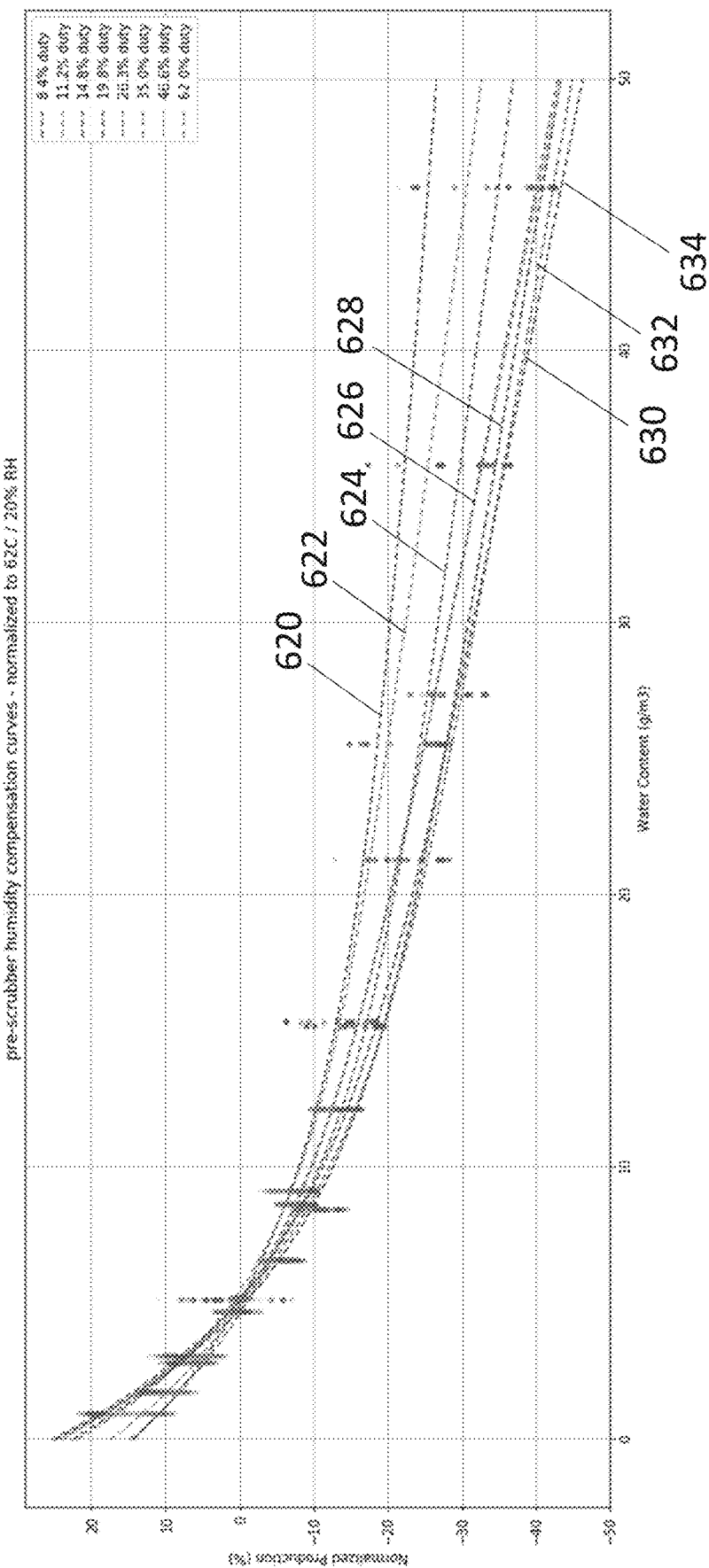
FIG. 39 illustrates an exemplary graph of water content of a gas as it relates to NO production.

Humidity compensation can rely on the observed tight correlation between production rate and the absolute water content of the air (g/m^3), as shown in FIG. 39. Humidity sensitivity can be characterized and compensation curves for a plurality of plasma duty cycles can be fitted to an exponential curve $a*\exp(-b*x)+c*x+d$, where x is the water content of the reactant gas in g/m^3. FIG. 39 illustrates a curve 620 for an 8.4% duty cycle, a curve 622 for 11.2% duty cycle, a curve 624 for 14.8% duty cycle, a curve 626 for 19.8% duty cycle, a curve 628 for 26.3% duty cycle, a curve 630 for 35% duty cycle, a curve 632 for 46.6% duty cycle, and a curve 634 for 62% duty cycle. In some embodiments, this compensation may be performed pre-scrubber; in others it may be performed post-scrubber.

In some embodiments, when the system is calibrated, the standard calibration curves (production vs. duty and flow) can be normalized to a standard humidity and temperature (e.g. 30% RH and 20 degrees Celsius) or, the calibration can be performed in a controlled environment. During operation, the system determines the correct, humidity-compensated duty cycle to achieve its target production rate as follows:

1. Determine the desired production rate
2. Determine the water content of the reactant gas 3. Use the humidity compensation curves to determine the normalized production rate at each duty cycle 4. Multiply the raw production rate values in the calibration table (production vs. duty, flow) with the normalized production rate to produce a humidity-compensated calibration table 5. The humidity-compensated calibration table is used to determine which duty cycle will produce the desired production rate.

Low NO generation can often present a challenge due to limitations in plasma energy and duration. Adding humidity to reactant gas (or not removing as much) can have an effect of suppressing NO production. This approach can be useful so long as condensation within the NO system is still prevented.

Other embodiments can also achieve the same effect (e.g. using a regression function or 3-dimensional table to directly calculate production rate as a function of duty, flow, humidity). However, the above approach can be less memory-intensive, easy to add to the algorithm, and can work without calibrating each system in an environmental chamber.

Figure 40:
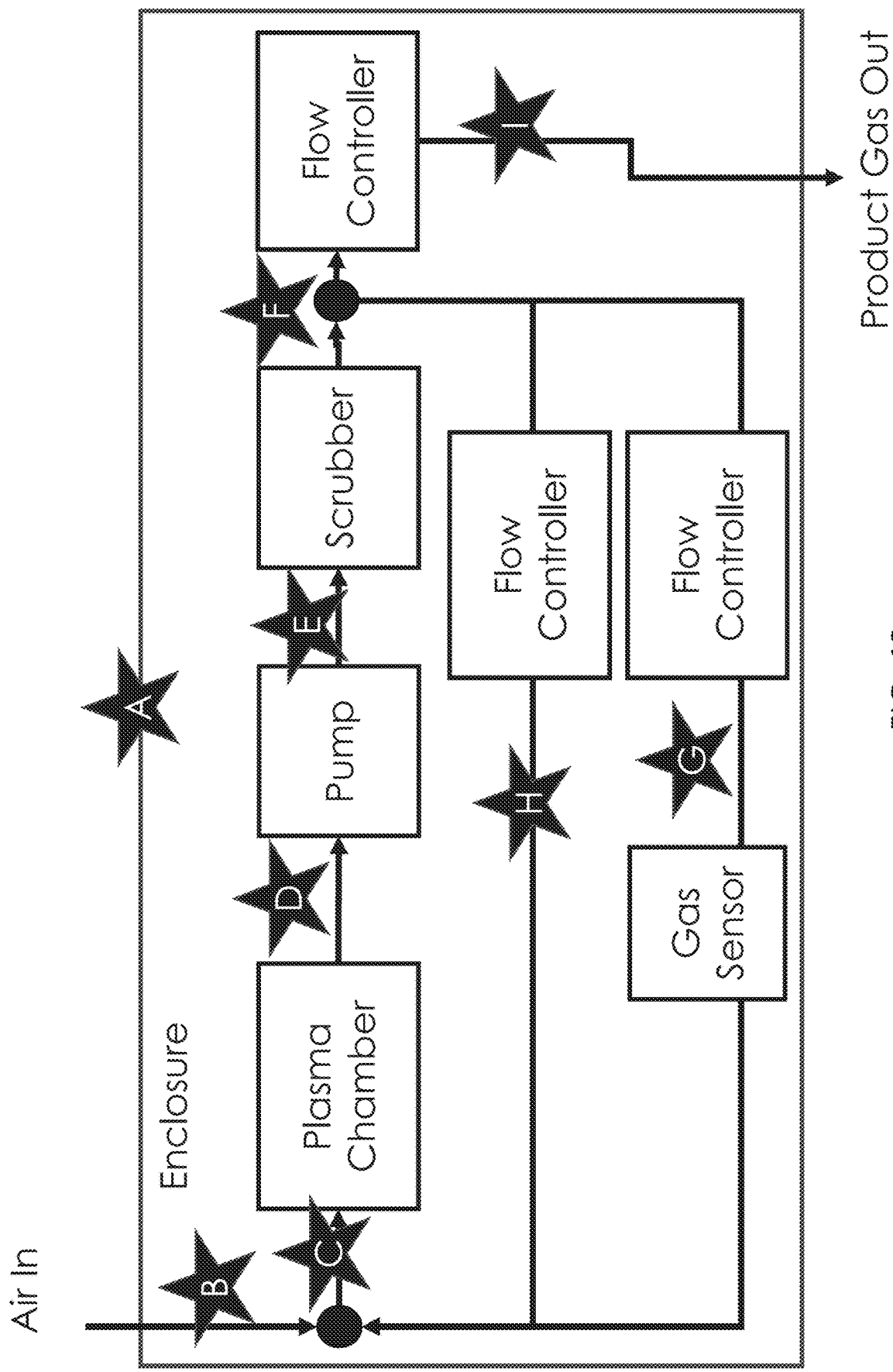
FIG. 40 illustrates exemplary location options for measurements related to gas humidity in a recirculation architecture.

FIG. 40 depicts an embodiment of a NO generation system with recirculation architecture. As shown in FIG. 40, there are various locations within a NO generation system that can be used for humidity-related measurements. At each location, one or more of humidity, temperature, and pressure can be measured. In some instances, if the downstream flow restriction is well-understood, a flow rate measurement can serve as a proxy for a pressure measurement. Location A measures ambient air conditions. Location B measures gas properties between the inlet and the recirculation loop. Location C measures gas properties within the recirculation loop after incoming air and recirculated gas mix. Measurements at this location benefit from being able to sense the variance in gas humidity attributed to the variable mixing of ambient air and recirculated air. It also can account for the variable amount water absorbed/added by the scrubber as gas circulates through the loop. Location D measures gas properties post plasma chamber. Location E measures gas properties between the pump and scrubber. This location tends to be the highest pressure with the most likely chance of water condensation. Location F measures gas properties downstream of the scrubber, before the flow controller. This location is above atmospheric pressure and can have elevated humidity from water release from the scrubber. Location G measures gas properties near the gas sensor to aid in maintaining humidity levels commensurate with gas sensor requirements. The gas sensor typically measures NO and/or $NO_2$. Location H measures the humidity of recirculated gas as it returns to the beginning of the loop. Sensor location I measures the humidity of gas prior to exiting the system. Each of these locations can be used to infer humidity levels at other locations within the system. A humidity level control algorithm deployed by the controller can use one or more gas property measurements at these locations as inputs to control a subsystem that does one or more of add water to a gas, remove water from a gas, or adjust the gas temperature and pressure properties to prevent condensation.

All publications, patent applications and patents mentioned herein are hereby incorporated by reference in their entirety as if each individual publication or patent was specifically and individually indicated to be incorporated by reference. Reference is made to U.S. application Ser. No. 15/907,241, filed Feb. 27, 2018, U.S. application Ser. No. 16/388,464, filed Apr. 18, 2019, U.S. application Ser. No. 16/697,498, filed Nov. 27, 2019, U.S. application Ser. No. 15/907,258, filed on Feb. 27, 2018, U.S. application Ser. No. 16/363,505, filed Mar. 25, 2019 and U.S. application Ser. No. 16/724,233, filed Dec. 21, 2019 which are all hereby incorporated by reference in their entireties.

It will be appreciated that several of the above-disclosed and other features and functions, or alternatives thereof, may be desirably combined into many other different systems or application. Various alternatives, modifications, variations, or improvements therein may be subsequently made by those skilled in the art.

What is claimed is:

1. A system for generating nitric oxide comprising:
at least one plasma generator configured to generate a product gas containing nitric oxide from a reactant gas;
at least one controller configured to regulate the amount of nitric oxide in the product gas generated by the plasma generator using one or more parameters as an input to the at least one controller;
a scrubber configured to remove nitrogen dioxide ($NO_2$) from the product gas;
a humidity control device configured to alter a water content of the reactant gas to control humidity within the system; and
one or more humidity sensors configured to communicate humidity information with the at least one controller.

2. The system of claim 1, wherein the one or more parameters relate to at least one of the reactant gas, the product gas, and an inspiratory gas into which at least a portion of the product gas flows.

3. The system of claim 2, wherein the controller is configured to communicate with the humidity control device to control the amount of water the humidity control device removes from the reactant gas.

4. The system of claim 2, wherein the one or more humidity sensors configured to communicate with at least one of the controller and the humidity control device.

5. The system of claim 1, wherein the one or more humidity sensors are configured to communicate the humidity information with the humidity control device, the humidity control device being configured to adjust the humidity in the system.

6. The system of claim 1, wherein the humidity control device is in the form of a water trap.

7. The system of claim 1, wherein the humidity control device is in the form of a humidity exchange material.

8. The system of claim 1, wherein the humidity control device is in the form of a humidity management material.

9. The system of claim 8, wherein the humidity management material is a desiccant.

10. The system of claim 1, wherein the humidity control device is in the form of a molecular sieve.

11. The system of claim 1, wherein the humidity control device is configured to titrate humid and dry gas to achieve a target gas humidity level.

12. The system of claim 1, wherein the humidity control device is in the form of at least one of an active heater and a passive heater.

13. The system of claim 1, wherein the humidity control device is configured to prevent drying out of the scrubber.

14. The system of claim 1, further comprising one or more sensors configured to sense information relating to at least one of the reactant gas, product gas, and inspiratory gas to be used as the parameters to the controller, and wherein the humidity control device is configured to prevent drying out of the one or more sensors.

15. A system for generating nitric oxide comprising:
- at least one plasma generator configured to generate a product gas containing nitric oxide from a reactant gas; and
- at least one controller configured to regulate the amount of nitric oxide in the product gas using one or more parameters as an input to the controller, the one or more parameters relating to at least one of the reactant gas, the product gas, and an inspiratory gas into which at least a portion of the product gas flows;
- a humidity control device configured to communicate with the at least one controller such that the controller can use the humidity control device to alter the humidity within at least one of the reactant gas and the product gas,
- wherein at least one parameter is humidity information in at least one of the reactant gas and the product gas to achieve a target nitric oxide production level.

16. The system of claim 15, wherein the system utilizes feedback to alter humidity as needed.

17. The system of claim 15, further comprising a scrubber configured to remove nitrogen dioxide ($NO_2$) from the product gas, and wherein the a humidity control device is configured to prevent drying out of the scrubber.

18. The system of claim 15, further comprising one or more sensors configured to sense information relating to at least one of the reactant gas, product gas, and inspiratory gas to be used as the parameters to the controller, and wherein the a-humidity control device is configured to prevent drying out of the one or more sensors.

19. The system of claim 15, further comprising a humidity sensor configured to communicate the humidity information to the controller.

20. The system of claim 15, wherein one or more parameters include at least one of geographic location, elevation, and atmospheric pressure information to control nitric oxide production.

21. A system for generating nitric oxide comprising:
- at least one plasma generator configured to generate a product gas containing nitric oxide from a reactant gas;
- at least one controller configured to regulate the amount of nitric oxide in the product gas using one or more parameters as an input to the at least one controller;
- a scrubber configured to remove nitric dioxide ($NO_2$) from the product gas;
- a humidity control device configured to alter a water content of at least one of the reactant gas and the product gas to control humidity within the system; and
- one or more humidity sensors configured to communicate humidity information with the at least one controller.

* * * * *